US006031133A

United States Patent [19]
Smith, III et al.

[11] Patent Number: 6,031,133
[45] Date of Patent: Feb. 29, 2000

[54] SYNTHETIC TECHNIQUES AND INTERMEDIATES FOR POLYHYDROXY, DIENYL LACTONES AND MIMICS THEREOF

[75] Inventors: Amos B. Smith, III, Merion; Yuping Qiu; Michael Kaufman, both of Philadelphia; Hirokaza Arimoto, Drexel Hill, all of Pa.; David R. Jones, Milford, Ohio; Kaoru Kobayashi, Osaka, Japan

[73] Assignee: The Trustees of the University of Pennsylvania, Philadelphia, Pa.

[21] Appl. No.: 09/021,878

[22] Filed: Feb. 11, 1998

Related U.S. Application Data

[62] Division of application No. 08/759,817, Dec. 3, 1996, Pat. No. 5,789,605.

[51] Int. Cl.[7] .................................................. C07C 233/04
[52] U.S. Cl. ......................................................... 564/170
[58] Field of Search ............................................. 564/170

[56] References Cited

U.S. PATENT DOCUMENTS

| 4,939,168 | 7/1990 | Gunasekera et al. | 514/459 |
| 5,010,099 | 4/1991 | Gunasekera et al. | 514/459 |
| 5,681,847 | 10/1997 | Longley et al. | 514/459 |

FOREIGN PATENT DOCUMENTS

| 2280677 | 2/1995 | United Kingdom . |

OTHER PUBLICATIONS

Clark, D.L. et al., "Studies on the Alkylation of Chiral Enolates: Application toward the Total Synthesis of Discodermolide", *J. Org. Chem.*, 1993, 58, 5878–5879.

Evans, P.L. et al., "The Synthesis of a $C_9$–$C_{17}$ Lactone Fragment of Discodermolide", *Tetra. Lett.*, 1993, 34(50), 8163–8166.

Golec, J.M.C. et al., "The Synthesis of a $C_1$–$C_8$ Lactone Fragment of Discodermolide", *Tetra. Lett.*, 1993, 34(50), 8159–8162.

Golec, J.M.C. et al., "An Approach to the Synthesis of a $C_9$–$C_{15}$ Fragment of Discodermolide", *Tetra. Lett.*, 1993, 34(50), 8167–8168.

Golec, J.M.C. et al., "Total synthesis of discodermolide", *Chemical Abstracts*, 1995, 123, 831, Abstract No. 32864j.

Green and Wuts, Protective Groups in Organic Synthesis, 2d Edition, John Wiley & Sons, New York, 1991.

Gunasekera et al., "Discodermolide: A New Bioactive Polyhydroxylated Lactone from the Marine Sponge *Discodermia dissoluta*", *J. Org. Chem.*, 1990, 55, 4912–4915.

Gunasekera et al., "Discodermolide: A New Bioactive Polyhydroxylated Lactone from the Marine Sponge *Discodermia dissoluta*: Additions and Corrections", *J. Org. Chem.*, 1991, 56(3), 1346.

Hodges et al., "Reactions to Lithiooxazole", *J. Org. Chem.*, 1991, 56, 449–452.

Hung et al., "Distinct binding and cellular properties of synthetic (+)– and (–)–discodermolides", *Chem. & Biol.*, 1994, 1(1), 67–71.

Hung et al., "(+)–Discodermolide binds to microtubules in stoichiometric ratio to tubulin dimers, blocks taxol binding and results in mitotic arrest", *Chem. & Biol.*, 1996, 3(4), 287–293.

Hung, D.T. et al., "Syntheses of Discodermolides Useful for Investigating Microtubule Binding and Stabilization", *J. Am. Chem. Soc.*, 1996, 118, 11054–11080.

Jacquesy et al., "Metabromation Du Dimethyl–2,6 Phenol Et De Son Ether Methylique En Milieu Superacide", *Tetrahedron*, 1981, 37, 747–751.

Kim et al., "Conversion of Acetals into Monothioacetals, α–Alkoxyazides and α–Alkoxyalkyl Thioacetates with Magnesium Bromide", *Tetra. lett.*, 1989, 30(48), 6697–6700.

Longley et al., "Discodermolide—A New, Marine–Derived Immunosuppressive Compound", *Transplantation*, 1991, 52(4), 650–661.

Longley et al., "Immunosuppression by Discodermolide", *Ann. N.Y. Acad. Sci.*, 1993, 696, 94–107.

Nerenberg et al., "Total Synthesis of the Immunosuppressive Agent (–)–Discodermolide", *J. Am. Chem. Soc.*, 1993, 115, 12621–12622.

Paterson, I. et al., "Studies Towards the Total Synthesis of the Marine–derived Immunosuppressant Discodermolide; Asymmetric Synthesis of a $C_1$–$C_8$ δ–lactone Subunit", *J. Chem. Soc. Chem. Commun.*, 1993, 1790–1792.

Paterson, I. et al., "Studies Towards the Total Synthesis of the Marine–derived Immunosuppressant Discodermolide; Asymmetric Synthesis of a $C_9$–$C_{24}$ Subunit", *Synlett*, 1995, 498–500.

Remington's Pharmaceutical Sciences, Mack Publishing Company, Easton, PA, 1980.

Roush et al., "Acyclic Diastereoselective Synthesis Using Tartrate Ester Modified Crotylboronates. Double Asymmetric Reactions with α–Methyl Chiral Aldehydes and Synthesis of the C(19)–C(29) Segment of Rifamycin S", *J. Am. Chem. Soc.*, 1990, 112, 6348–6359.

Smith et al., "Total Synthesis of (–)–Discodermolide", *J. Am. Chem. Soc.*, 1995, 117, 12011–12012.

Solladie et al., "Asymmetric Synthesis of Polyhydroxylated Natural Products II. The C–1/C–12 Unit of Amphotericin B", *Tetra. Lett.*, 1987, 28(7), 797–800.

ter Haar et al., "Discodermolide, A Cytotoxic Marine Agent that Stabilizes Microtubules More Potently than Taxol", *Biochem.*, 1996, 35, 243–250.

Yang, G. et al., "The Synthesis of the C–9 to C–21 Sector of Discodermolide: An Efficient Route to the C13–14 Z–Trisubstituted Alkene", *Tetra. Lett.*, 1994, 35(16), 2503–2504.

(List continued on next page.)

*Primary Examiner*—John Kight
*Assistant Examiner*—Charanejit S. Aulakh
*Attorney, Agent, or Firm*—Woodcock Washburn Kurtz Maciewicz & Norris LLP

[57] ABSTRACT

Synthetic methods for lactone-containing compounds such as the discodermolides are provided, as are compounds which mimic the chemical and/or biological activity thereof, and methods and intermediates useful in their preparation.

5 Claims, 31 Drawing Sheets

OTHER PUBLICATIONS

Yang, G. et al., "An Alkylative Strategy to the C–13 to C–21 Sector of Discodermolide", *Tetra. Lett.*, 1994, 35(9), 1313–1316.

Evans, D.A. et al., "Enantioselective Synthesis of Altohyrtin C (Spongistatin 2): Synthesis of the AB– and CD–Spiroketal Subunits", *Angew. Chem. Int. Ed. Engl.*, 1997, 36(24), 2738–2740.

Evans, D.A. et al., "Enantioselective Synthesis of Altohyrtin C (Spongistatin 2): Synthesis of the EF–Bis(pyran) Subunit", *Angew. Chem. Int. Ed. Engl.*, 1997, 36(24), 2741–2743.

Evans, D.A. et al., "Enantioselective Synthesis of Altohyrtin C (Spongistatin 2): Fragment Assembly and Revision of the Spongistatin 2 Stereochemical Assignment", *Agnew. Chem. Int. Ed. Engl.*, 1997, 36(24), 2744–2747.

Guo, J. et al., "Total Synthesis of Altohytrin A (Spongistatin 1): Part 1", *Angew. Chem. Int. Ed. Engl.*, 1998, 37(1/2), 157–191.

Hayward, M.M. et al., "Total Synthesis of Altohyrtin A (Spongistatin 1): Part 2", *Angew. Chem. Int. Ed. Engl.*, 1998, 37(1/2), 192–196.

Paterson, I. et al., "Studies in Marine Macrolide Synthesis: Synthesis of the $C_1$–$C_{15}$ Subunit of Spongistatin 1 (Altohytrin A) and 15,16–Anti Aldol Coupling Reactions", *Tetra. Lett.*, 1997, 38(47), 8241–8244.

Paterson, I. et al., "Studies in Marine Macrolide Synthesis: Synthesis of a $C_{16}$–$C_{28}$ Subunit of Spongistatin 1 (Altohytrin A) Incorporating the CD–Spiroacetal Moiety", *Tetra. Lett.*, 1997, 38(51), 89811–8914.

Balachandran, R. et al., "The potent microtubule–stabilizing agent (+)–discodermolide induces apoptosis in human breast carcinoma cells—preliminary comparisons to paclitaxel", *Anti–Cancer Drugs*, 1998, 9, 67–76.

Gunasekera et al., "Discodermolide: A New Bioactive Polyhydroxylated Lactone from the Marine Sponge *Discodermia dissoluta*", *J. Org. Chem.*, 1991, 56(3), 1346 (Additions and Corrections to p. 4912 of article found in *J. Org. Chem.*, 1990, 55, 4912–4915).

Harried, S.S. et al., "Total Synthesis of ( – )–Discodermolide: An Application of an Chelation–COntrolled Alkylation Reaction", *J. Org. Chem.*, 1997, 62, 6098–6099.

Kowalski, R.J. et al., "The Microtubule–Stabilizing Agent Discodermolide Competitively Inhibits the Binding of Paclitaxel (Taxol) to Tubulin Polymers, Enhances Tubulin Nucleation Reactions More Potently than Paclitaxel, and Inhibits the Growth of Paclitaxel–Resistant Cells", *Mol. Pharmacology*, 1997, 52, 613–622.

Marshall, J.A. et al., "Synthesis of Discodermolide Subunites by $S_E2'$ Addition of Nonracemic Allensylstannanes to Aldehydes", *J. Org. Chem.*, 1998, 63, 817–823.

Miyazawa, M. et al., "Stereoselective Synthesis of the $C_1$–$C_7$ Segment of (+)–Discodermolide", *Chem. Letts.*, 1997, 1191–1192.

Miyazawa, M. et al., "Synthesis of the $C_8$–$C_{15}$ Segment of (+)–Discodermolide", *Chem. Letts.*, 1997, 1193–1194.

Smith, III et al., "Synthesis and in Vitro Cancer Cell Growth Inhibitory Activity of Monocyclic Model Compounds Containing Spongistatin Triene Side–Chains", *Bioorg. Med. Chem. Letts.*, 1998, 8, 567–568.

Walkup, R.D. et al., "Expeditious Synthesis of a Key $C_9$–$C_{21}$ Subunit of the Aplysiatoxins and Oscillatoxins", *Tetra. Lett.*, 1990, 31(52), 7587–7590.

Shimizu, S. et al.: Total synthesis of (+)–Tautomycin. Tetrahedron, vol. 52, pp. 13363–13408, Oct. 14, 1996.

(-)-Discodermolide (1)

• Denote the repeating stereochemical triad

SYNTHETIC TECHNIQUES AND INTERMEDIATES FOR POLYHYDROXY, DIENYL LACTONES AND MIMICS THEREOF

This application is a Div. of Ser. No. 08/759,817 filed Dec. 3, 1996, now U.S. Pat. No. 5,789,605.

GOVERNMENT SUPPORT

Certain of the inventors were supported by National Institutes of Health Grant GM-29028.

FIELD OF THE INVENTION

This invention relates to lactone-containing compounds such as discodermolide, to compounds which mimic the chemical and/or biological activity thereof, and to methods and intermediates useful in their preparation.

BACKGROUND OF THE INVENTION

In 1990, Gunasekera and co-workers at the Harbor Branch Oceanographic Institute reported the isolation of (+)-discodermolide (1), an architecturally novel metabolite of the marine sponge *Discodermia dissoluta* (0.002% w/w). (See, Gunasekera, et al., *J. Org. Chem.* 1990, 55, 4912. Correction: *J. Org. Chem.* 1991, 56, 1346).

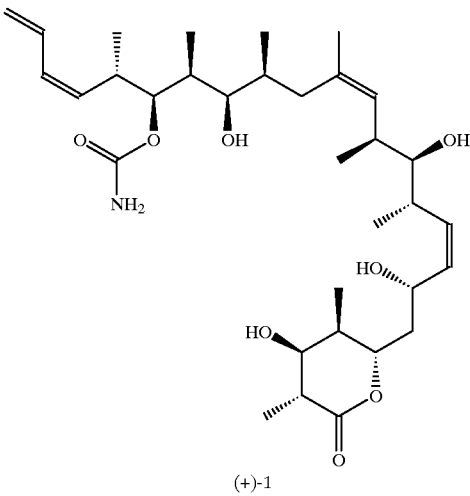

(+)-1

Initial studies revealed that (+)-discodermolide suppresses both the two-way mixed-lymphocyte reaction and the concanavalin A-induced mitogenesis of murine splenocytes in vitro with no associated cytotoxicity. Moreover, (+)-1 suppresses the in vivo graft-vs.-host splenomegaly response induced by injection of parental splenocytes into F1 recipient mice, with potency intermediate between those of cyclosporin A and FK506. (Longley, et al., *Transplantation* 1991, 52, 650; Longley, et al., *Transplantation* 1991, 52, 656; Longley, et al. *Ann. N.Y. Acad. Sci.* 1993, 696, 94). These findings stimulated the recent discovery that (+)-1 arrests cell development at the M phase by binding and stabilizing mitotic spindle microtubules; thus discodermolide resembles taxol in its mode of action, but the microtubule binding affinity of 1 is much higher. (ter Haar, et al., *Biochemistry* 1996, 35, 243; Hung, et al., *Chemi.& Biol.* 1996, 3, 287). These and other results suggest that (+)-discodermolide holds considerable promise as an anticancer agent. The scarcity of natural material however has precluded a complete evaluation of its biological profile.

The absolute configuration of discodermolide remained undefined until Schreiber et al. synthesized both antipodes of 1. (Nerenberg, et al. *J. Am. Chem. Soc.* 1993, 115, 12621; Hung, et al., *Chem. & Biol.* 1994, 1, 67). Interestingly, the unnatural (−) antipode also displays significant immunosuppressant activity.

There is, therefore, a need for improved synthetic methods for the preparation of polyhydroxy, dienyl lactones such as the discodermolides, as well as a need for compounds having similar chemical and/or biological activity.

OBJECTS OF THE INVENTION

It is one object of the present invention to provide polyhydroxy, dienyl lactones and mimics thereof.

It is a further object to provide processes for the preparation of such compounds and their mimics.

It is another object of this invention to provide intermediates useful in such processes.

SUMMARY OF THE INVENTION

These and other objects are satisfied by the present invention, which, in one aspect, provides synthetic methods for the discodermolides and other polyhydroxylactones. In preferred embodiments, such methods involve contacting a phosphonium salt of formula I:

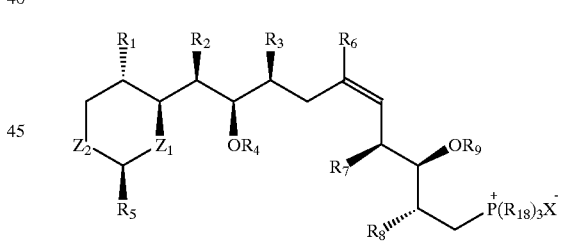

with base and an alkylthiol of formula II:

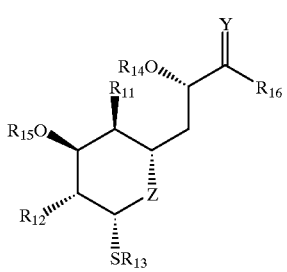

to form a diene of formula III:

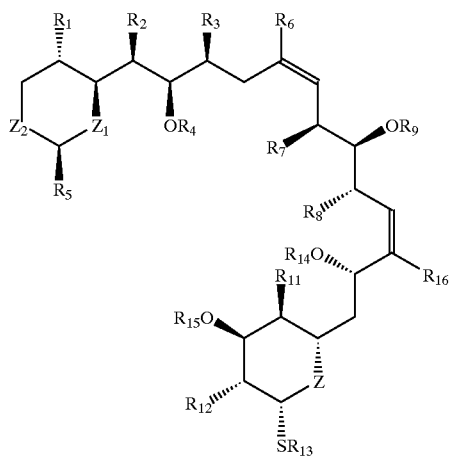

III wherein $R_1$, $R_2$, $R_3$, $R_6$, $R_7$, $R_8$, $R_{11}$, $R_{12}$ and $R_{13}$ are, independently, $C_1$–$C_{10}$ alkyl;

X is a halogen;

Z, $Z_1$, and $Z_2$ are, independently, O, S or NR';

$R_4$, $R_9$, $R_{14}$, and $R_{15}$ are, independently, acid labile hydroxyl protecting groups;

$R_5$ is $C_6$–$C_{14}$ aryl;

Y is O, S or NR';

R' and $R_{16}$ are, independently, hydrogen or $C_1$–$C_6$ alkyl; and $R_{18}$ is $C_6$–$C_{14}$ aryl.

In another aspect, the methods of the invention involve producing an alkene of formula IV.

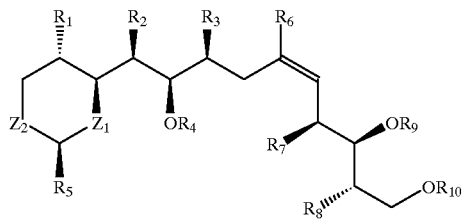

IV

This can be accomplished by contacting an organometallic reagent of formula Va:

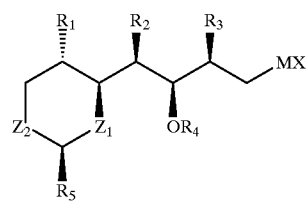

Va with a vinyl halide of formula VIa:

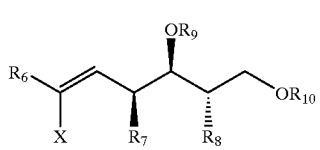

VIa

Wherein M is Li, Cu, Mg, or Zn and $R_{10}$ is an acid stable hydroxyl protecting group and all other variables are as defined above. Alternatively, a vinyl halide of formula Vb:

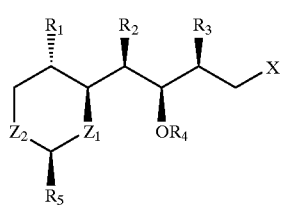

Vb can be contacted with an organometallic compound of formula VIb:

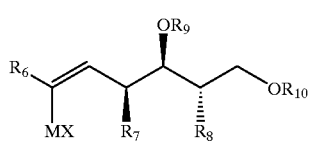

VIb

In yet another aspect, the methods of the invention involve lactones having formula VII.

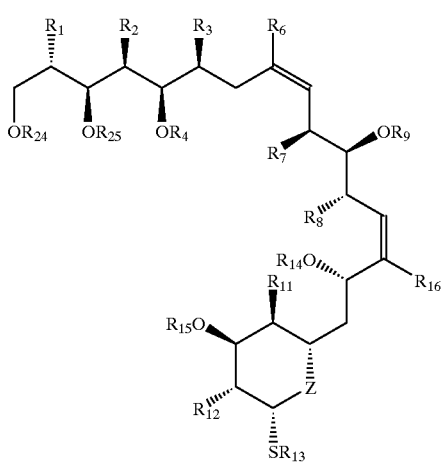

VII by contacting a diene of formula VIIIa:

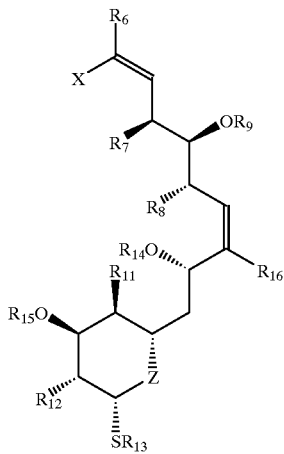

VIIIa with an organometallic compound having formula Va wherein $R_{24}$ is hydrogen and $R_{25}$ is hydrogen or an acid stable hydroxyl protecting group. Alternatively, an organometallic compound having formula VIIIb can be contacted with a vinyl halide having formula Vb.

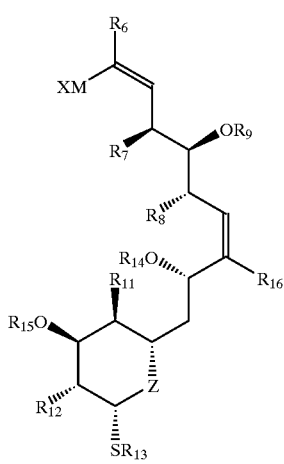

VIIIb

The methods of the invention also involve producing dienes having formula VIIIa by contacting phosphonium salts having formula IX:

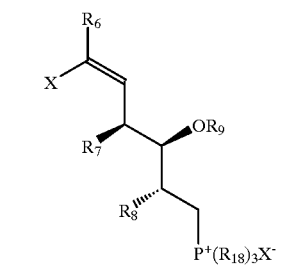

IX with base and alkylthiol compounds having formula II.

The present invention also provides synthetic intermediates which are useful in the preparation of polyhydroxylactones, including the compounds having formulas I–IX and X:

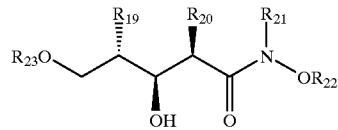

X wherein:
$R_{19}$, $R_{20}$, $R_{21}$ and $R_{22}$ are, independently, $C_1$–$C_{10}$ alkyl; and
$R_{23}$ is $C_7$–$C_{15}$ aralkyl.

The present invention also provides compounds which mimic the chemical and/or biological activity of the discodermolides. In preferred embodiments, such compounds have formula XI:

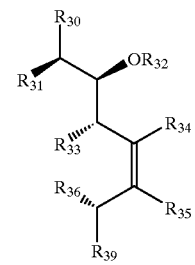

XI where
$R_{30}$ is substituted or unsubstituted $C_1$–$C_{10}$ alkyl or a moiety formula XII or XIII:

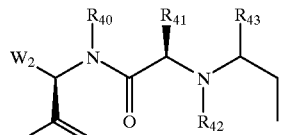

XII

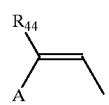

XIII where
A is $C_1$–$C_{20}$ alkyl, —$CH_2NH(T)$ or a moiety of formula XIV:

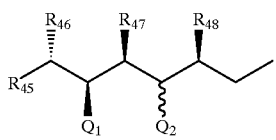

XIV wherein
T is peptide having 1 to about 10 amino acids;
$R_{32}$, $R_{40}$, $R_{42}$, $R_{43}$, $R_{46}$, $R_{47}$, and $R_{48}$ are, independently, hydrogen or $C_1$–$C_6$ alkyl;
$R_{41}$ is a side chain of an amino acid;
$W_1$ and $W_2$ are, independently, —$OR_{49}$ or —$NHP_1$;

$P_1$ is hydrogen or an amine protecting group;

$R_{33}$ and $R_{36}$ are, independently, hydrogen, $C_1-C_{10}$ alkyl, $-OR_{50}$, $=O$ or together form $-CH_2-CH_2-$;

$R_{34}$ and $R_{35}$ are, independently, hydrogen or together form $-C(H)=C(H)-C(H)=C(H)-$;

$R_{39}$ is $-OR_{51}$ or $-CH_2-R_{51}$;

$R_{31}$ and $R_{44}$ are, independently, $C_1-C_{10}$ alkyl;

$Q_1$ and $Q_2$ are, independently, hydrogen, $-OR_Q$, $-NHR_{52}$, $-OC(=O)NH_2$ or together form $-O-C(O)-NH-$;

$R_Q$ is hydrogen or a hydroxyl protecting group;

$R_{51}$ is substituted or unsubstituted $C_6-C_{14}$ aryl, tetrahydropyranyl, furanosyl, pyranosyl (e.g., tetramethylfucosyl, tetramethylmannosyl, tetramethylgaractosyl and tetramethylglucosyl), $C_3-C_{10}$ lactonyl or 2-pyranonyl;

$R_{45}$ is $C_1-C_6$ alkenyl, $C_1-C_6$ alkyl, $C_6-C_{14}$ aryl, $C_2-C_{10}$ heterocycloalkyl, $C_3-C_{10}$ cycloalkyl, or $C_7-C_{15}$ aralkyl; and $R_{49}$, $R_{50}$, and $R_{52}$ are, independently, hydrogen or $C_1-C_6$ alkyl.

The present invention also provides methods for inhibiting mammalian cell proliferation by contacting mammalian cells with a compound according to the invention or by administering a compound according to the invention (or a pharmaceutical composition comprising such a compound) to a mammal suffering from undesired cell proliferation. Also provided are methods for inhibiting rejection of a transplanted organ in a mammal comprising administering a compound or composition according to the invention to a mammalian organ recipient.

BRIEF DESCRIPTION OF THE DRAWINGS

The numerous objects and advantages of the present invention may be better understood by those skilled in the art by reference to the accompanying figures, in which.

DETAILED DESCRIPTION OF THE PREFERRED EMBODIMENTS

It has been found in accordance with the present invention that the synthesis of polyhydroxy, dienyl lactones such as the discodermolides can be achieved by highly convergent and stereocontrolled synthetic procedures.

Figure 1:
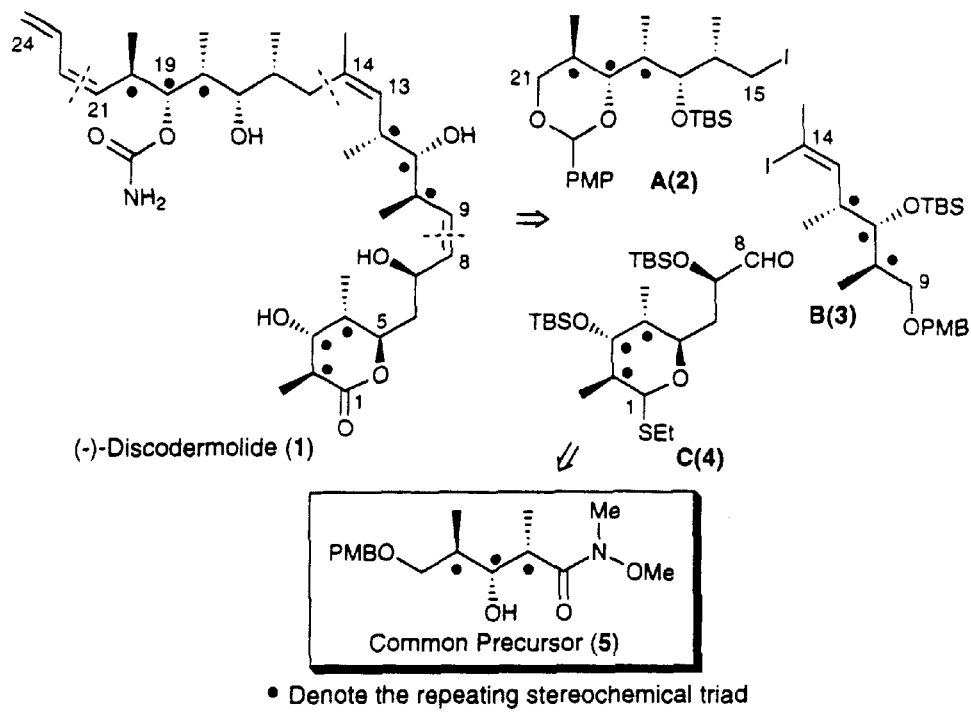
FIG. 1 shows a retrosynthetic analysis for (−)-discodermolide 1.

As shown in FIG. 1 for the (−)-discodermolide antipode, our analysis revealed a repeating triad of contiguous stereocenters, separated by Z-olefinic linkages at C(8,9) and C(13,14). Disconnections at C(8,9), C(14,15) and C(21,22) generated fragments A, B and C, each deriving in turn from a common precursor (5) containing the recurring stereochemical triad.

Figure 2:
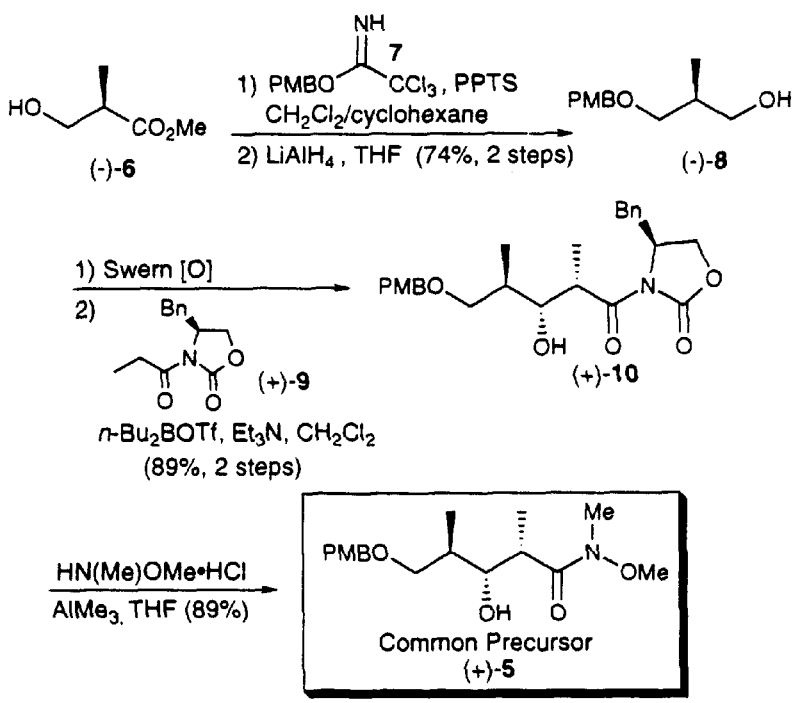
FIG. 2 shows a synthetic scheme for compound 5.

As shown in FIG. 2, precursor 5 was prepared by a synthetic procedure whereby hydroxy ester (−)-6 was protected as the p-methoxybenzyl (PMB) ether by treatment with the Bundle trichloroimidate reagent 7 under acidic conditions. Reduction with LiAlH$_4$ provided the alcohol (−)-8 after distillation. Swern oxidation, Evans aldol condensation, and Weinreb amide formation completed the construction of common precursor (+)-5. This concise five-step synthesis could be routinely carried out on a 50-g scale in 59% overall yield.

Figure 3:
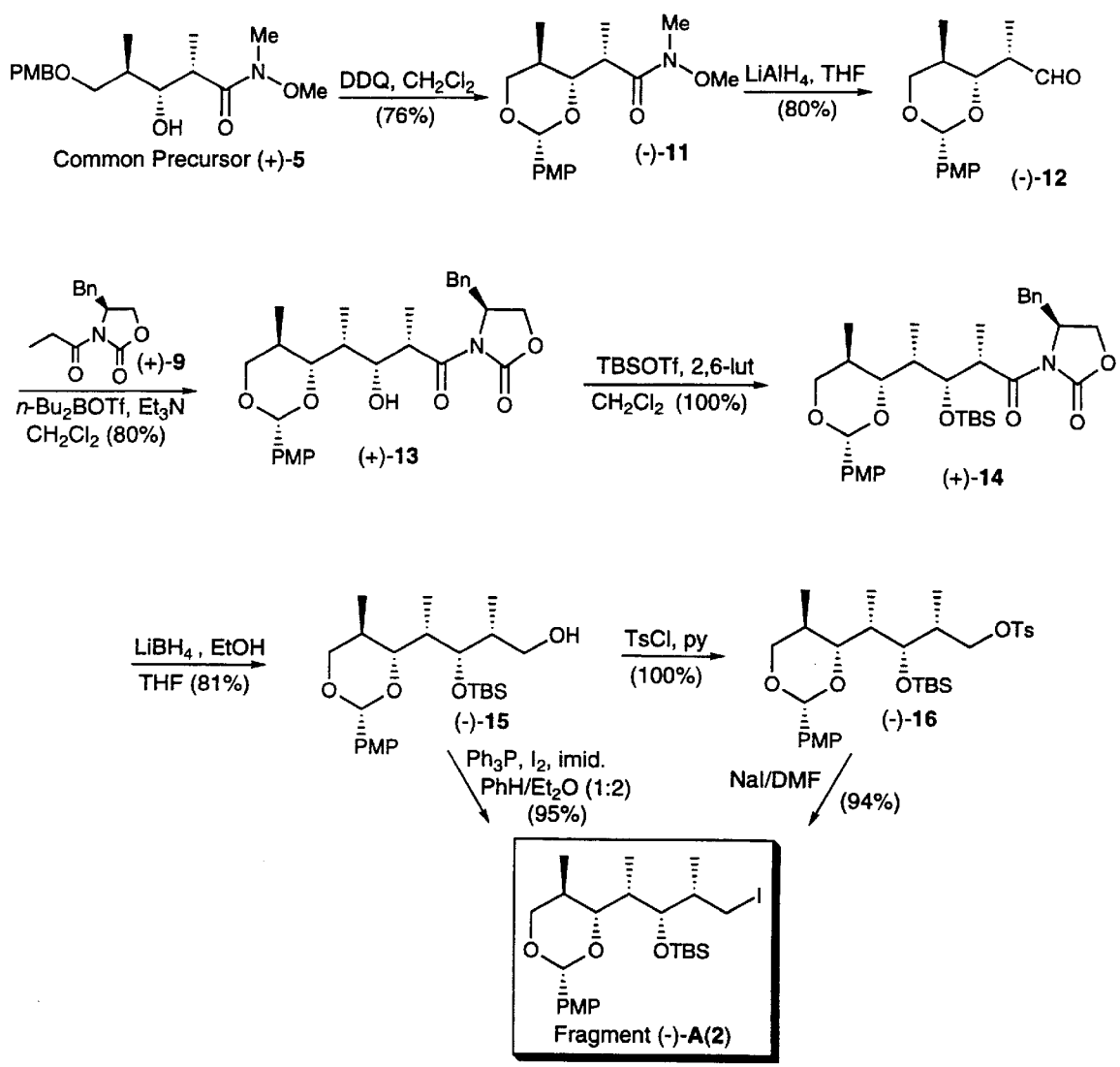
FIG. 3 shows a synthetic scheme for fragment A.

In view of the polypropionate structure of the A fragment, we performed a second asymmetric aldol reaction, as shown in FIG. 3. Initial formation of the p-methoxybenzylidene acetal (−)-11 from common precursor (+)-5 (78% yield) was designed to allow selective deprotection of C(21) and C(19) hydroxyls for introduction of the terminal diene and carbamate moieties. Following reduction of amide (−)-11 to the aldehyde (80% yield), (aldol reaction with oxazolidinone (+)-9 (80% yield) provided alcohol (+)-13 which incorporated the five stereocenters of subunit A. The structure of (+)-13 was confirmed by single-crystal X-ray analysis. Protection of the secondary alcohol as the TBS ether and removal of the chiral auxiliary (LiBH$_4$,EtOH,THF) afforded primary alcohol (−)-15 (81% yield, two steps), which could be efficiently converted either to tosylate (−)-16 or iodide (−)-A.

Figure 4:
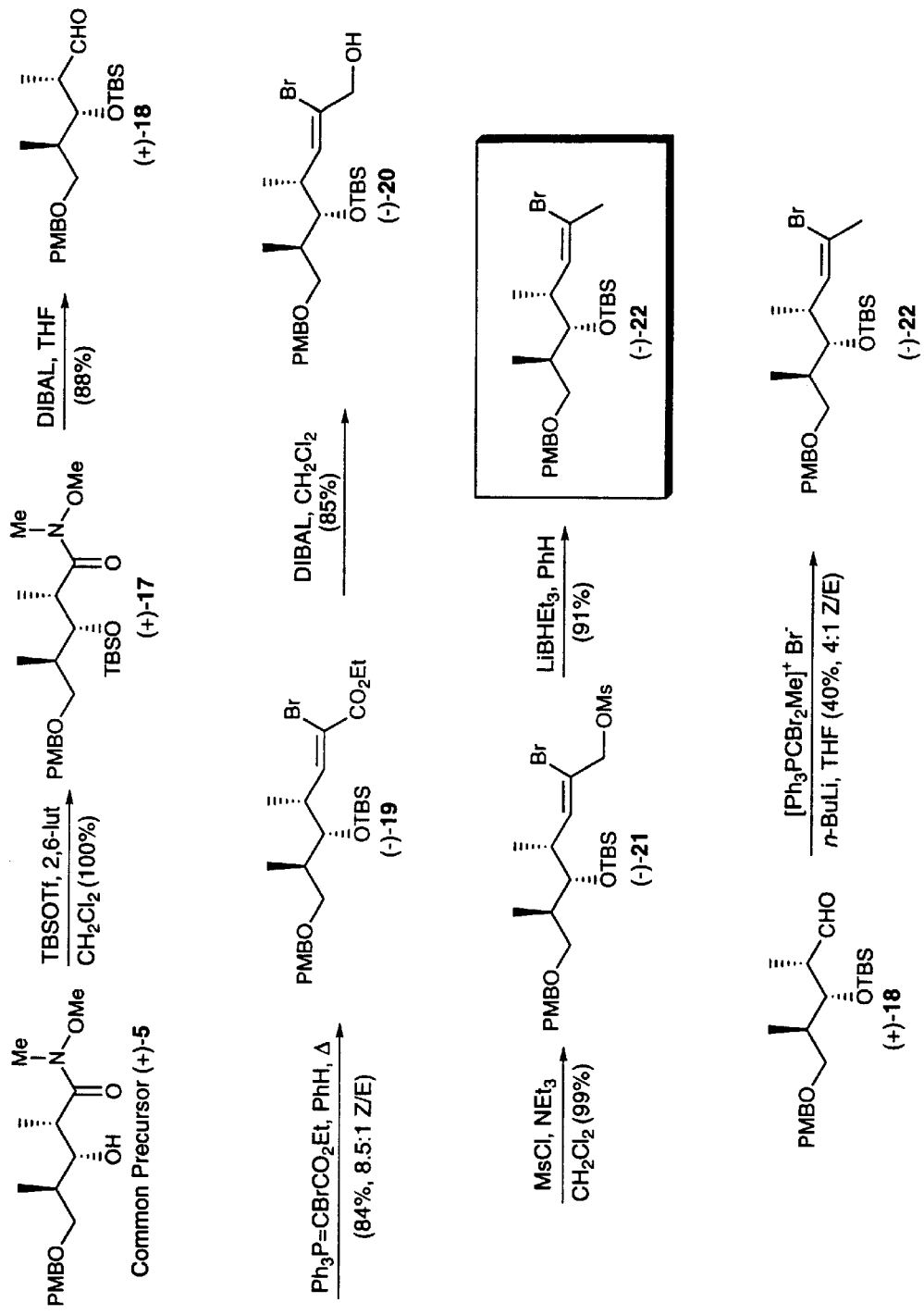
FIG. 4 shows a synthetic scheme for compound 22.

As outlined in FIG. 1, our strategy required a Z vinylic halide B for coupling with fragment A. Beginning again with the common precursor (+)-5, TBS protection (FIG. 4) followed by reduction of the Weinreb amide [DIBAL (2 equiv), THF, −78° C.] (Kim, et al., *Tetrahedron Lett.* 1989, 30, 6697)[16] afforded aldehyde (+)-18 in 88% yield for the two steps. We adopted a stepwise approach to introduction of the vinyl halide, whereby (+)-18 was converted to the Z α-bromo unsaturated ester (−)-19 (Ph$_3$PCBrCO$_2$Et, PhH, reflux; 75% yield after chromatography). Reduction to allylic alcohol (−)-20 followed by mesylation and displacement with LiBHEt$_3$ then furnished Z vinyl bromide (−)-22 in 77% overall yield from 19.

Figure 5:
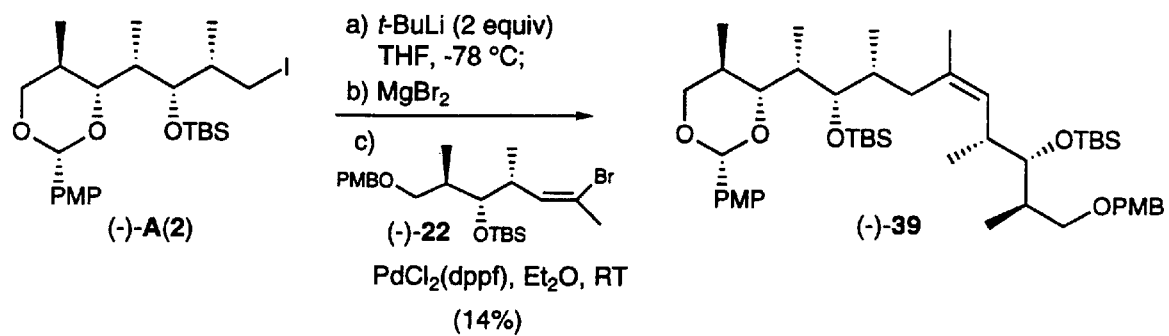
FIG. 5 shows a synthetic scheme for compound 39.
Figure 6:
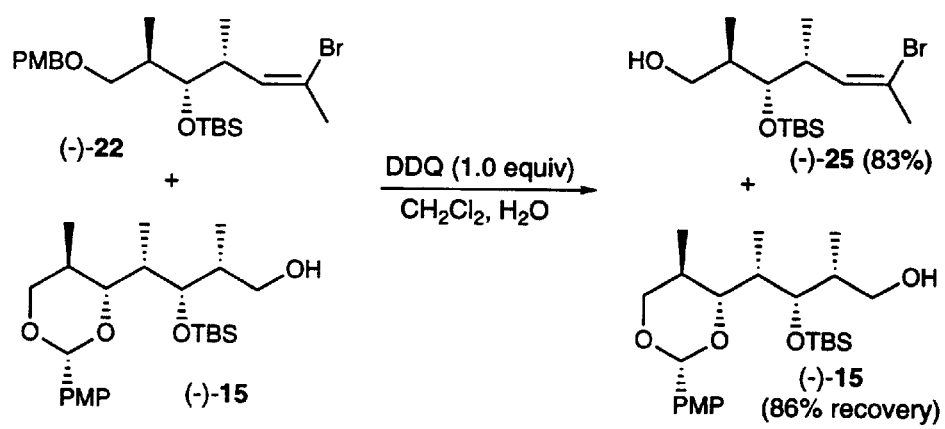
FIG. 6 shows a synthetic scheme for compounds 15 and 25.

Our preferred synthetic strategy involves selective removal of a primary PMB ether in the presence of a PMP acetal in the AB coupling product ((−)-39, FIG. 5). A 1:1 mixture of PMB ether (−)-22 and PMP acetal (−)-15 was exposed to DDQ (1.1 equiv) in CH$_2$Cl$_2$/H$_2$O (FIG. 6). The acetal (−)-15 largely remained intact while the debenzylated alcohol (−)-25 was formed in 83% yield.

Figure 7:
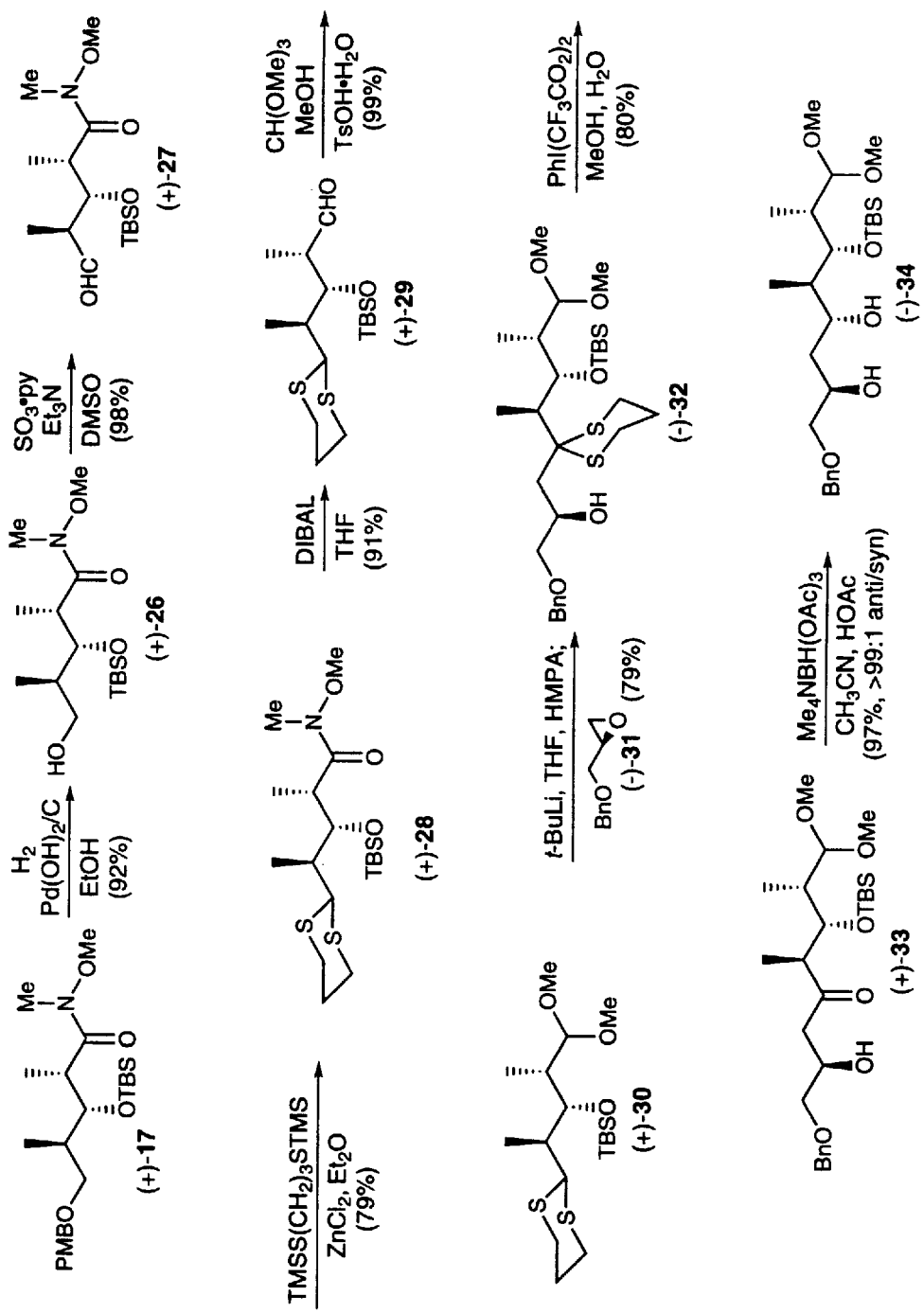
FIG. 7 shows a synthetic scheme for compound 34.

As shown in FIG. 7, we again utilized the TBS ether (+)-17 for the preparation of C from common precursor (+)-5. Oxidative cleavage of the PMB group (DDQ, CH$_2$Cl$_2$, H$_2$O) provided alcohol 26 in variable (60–86%) yields, accompanied by the corresponding lactone. Debenzylation with Pearlman's catalyst afforded (+)-26 in 92% yield. Exposure of the alcohol to SO$_3$.pyr furnished aldehyde (+)-27 (98% yield), which in turn was converted to dithiane (+)-28 (79%). In the latter step, our modification of the Evans protocol for dithiane generation [(TMSSCH$_2$)$_2$CH$_2$, ZnCl$_2$, Et$_2$O] minimized elimination of the TBS ether to form the α,β-unsaturated amide. Following reduction to aldehyde (+)-29 with DIBAL (91% yield), dimethyl acetal formation gave (+)-30 (99%). The coupling of dithiane 30 with R-(−)-glycidyl benzyl ether [(−)-31] then afforded alcohol (−)-32 in 79% yield. Unmasking of the ketone moiety [(CF$_3$CO$_2$)$_2$IPh, 80%] and Evans stereocontrolled reduction (97%) provided the anti diol (−)-34, which embodied all of the stereocenters in fragment C.

Figure 8:
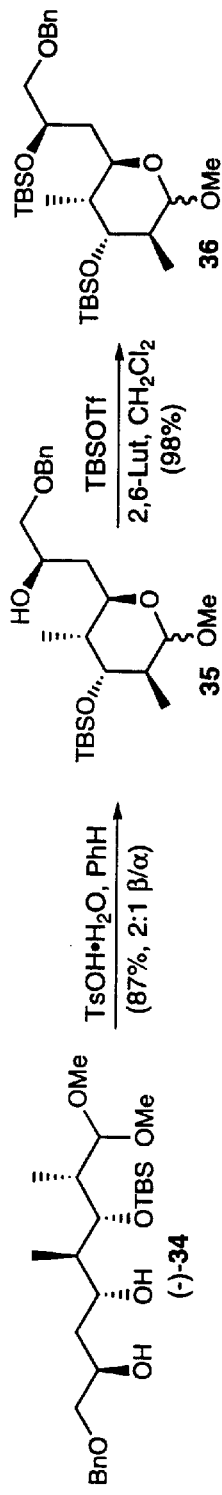
FIG. 8 shows a synthetic scheme for fragment C.
Figure 8:
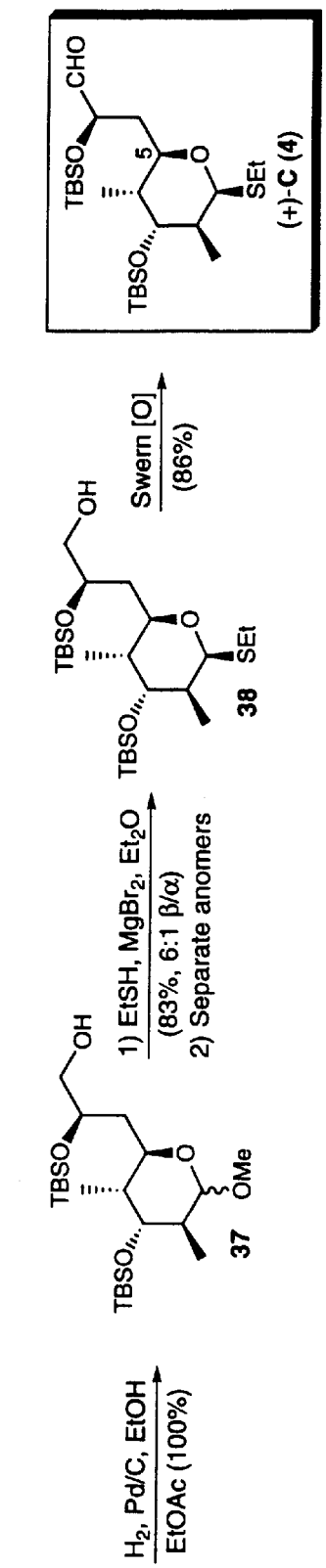

Acid-catalyzed cyclization of (−)-34 (TsOH, room temperature) provided methoxy pyran 35 in 87% yield as a 1:2 mixture of and β anomers (FIG. 8). Debenzylation (H$_2$, Pd/C) of 36 afforded alcohol 37 quantitatively. Exposure to EtSH and MgBr$_2$ in Et$_2$O then gave a separable 6:1 mixture of β ethyl hemithioacetal (+)-38 and its a anomer in 83% yield. Swern oxidation of (+)-38 furnished the final fragment (+)-C in 86% yield.

Figure 9:
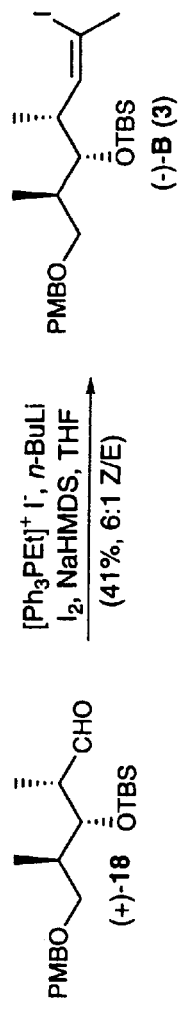
FIG. 9 shows a synthetic scheme for fragment B.
Figure 10:
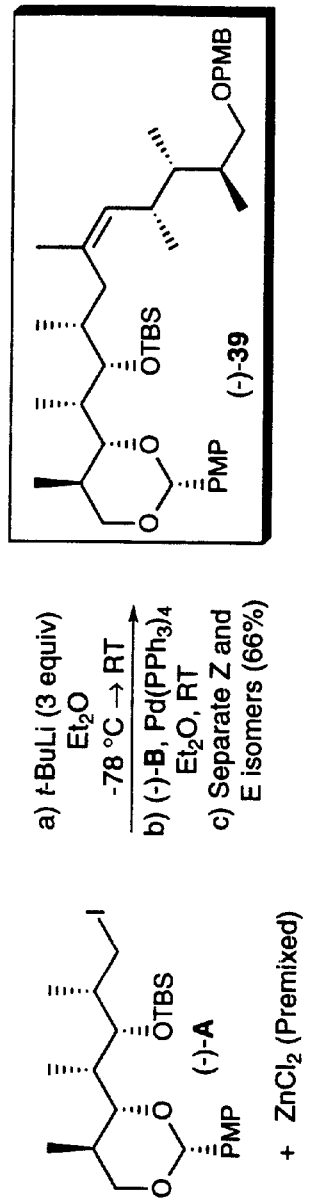
FIG. 10 shows a synthetic scheme for compound 39.

Synthesis of the desired B segment (−)-B preferably was achieved by direct olefination of aldehyde (+)-18 (41%, 6:1 Z/E) (FIG. 9), followed by chromatographic removal of the undesired E cross coupling product. Reaction of (−)-B with the organozinc derivative of (−)-A (FIG. 10) was achieved by premixing iodide A with dried solid ZnCl$_2$ (ether, −78° C.) before addition of t-BuLi. It is believed that three equivalents of t-BuLi are required for complete consumption of (−)-A, probably because the first equivalent reacts with ZnCl$_2$. This modification increased the yield to 66% after flash chromatography.

Figure 11:
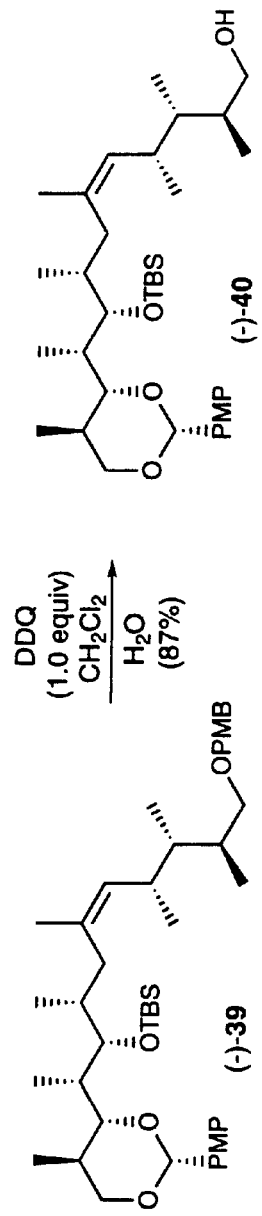
FIG. 11 shows a synthetic scheme for compound 40.
Figure 12:
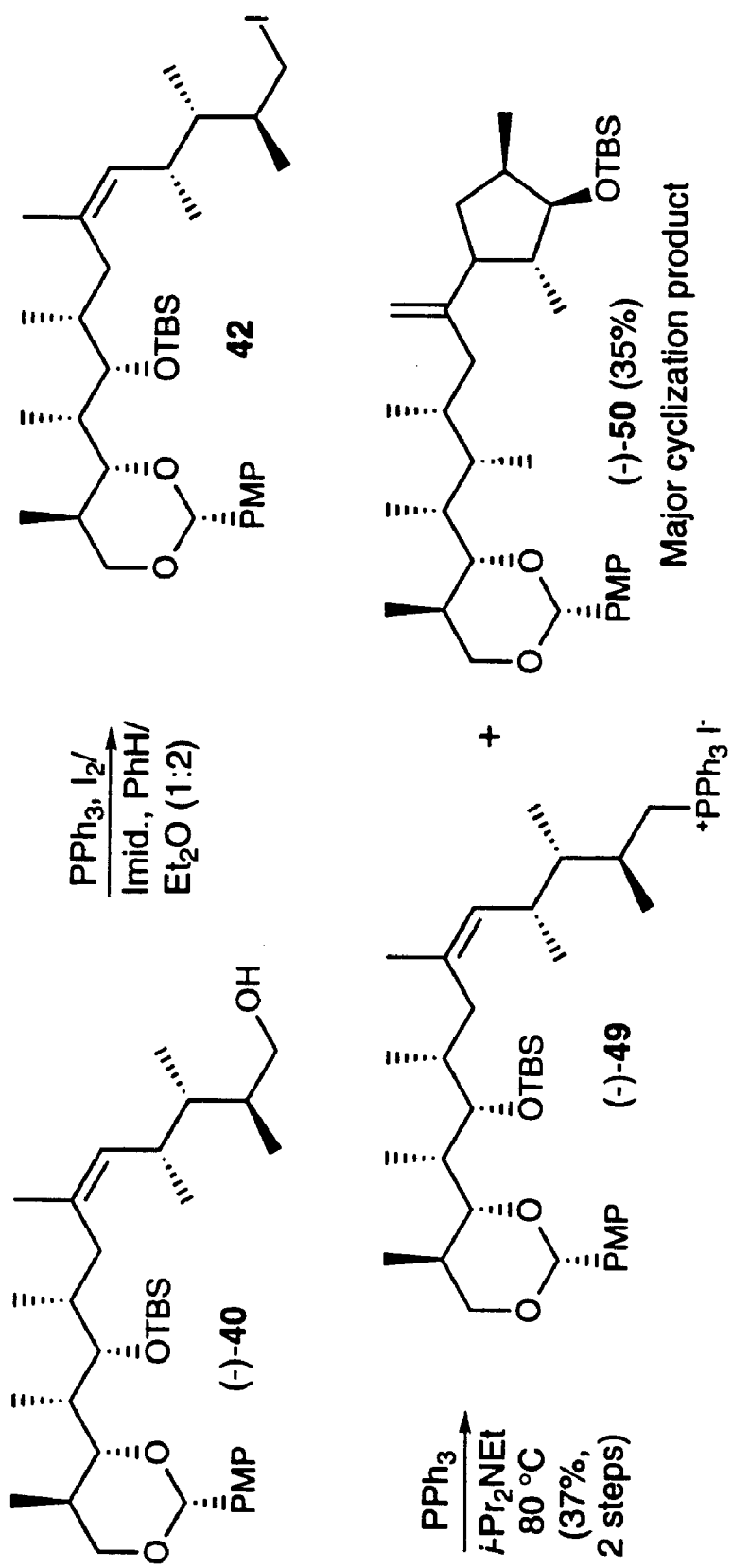
FIG. 12 shows a synthetic scheme for compound 49.
Figure 13:
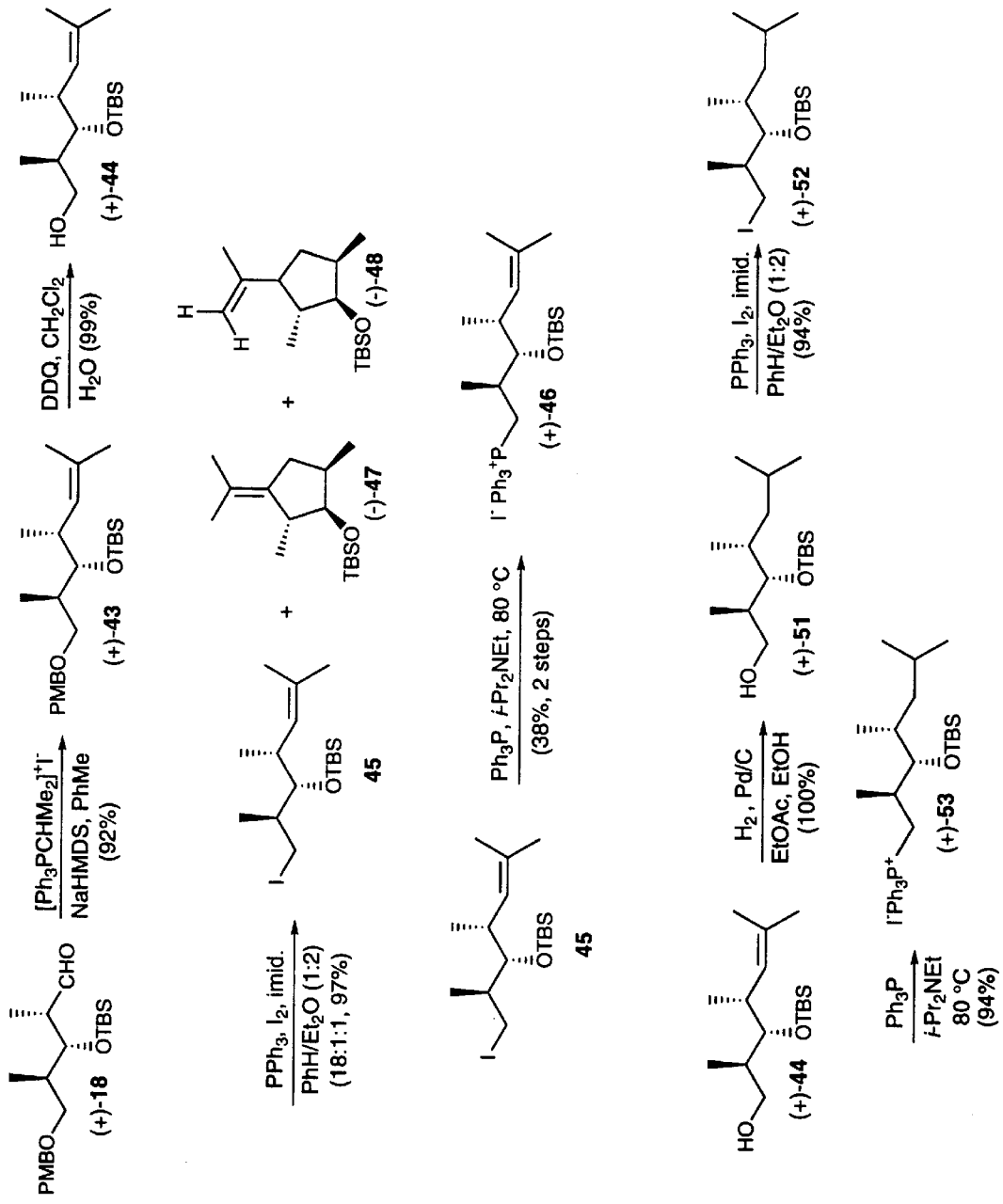
FIG. 13 shows a synthetic scheme for compounds 53 and 46.

Conversion of the Z trisubstituted olefin (−)-39 to the phosphonium iodide (−)-49 began with selective removal of the PMB group, as in our model study (DDQ, CH$_2$Cl$_2$, H$_2$O), furnishing (−)-40 in 87% yield (FIG. 11). As shown in FIG. 12, alcohol (−)-40 furnished the requisite iodide 42 almost exclusively, as indicated by NMR examination of the crude material. The very sensitive iodide was used without purification. Thorough mixing of iodide 42 with i-Pr$_2$NEt (3 equiv) followed by exposure to excess PPh$_3$ (15 equiv) without solvent at 80° C. generated (−)-49 in 37% yield for the two steps. The major by-product was characterized as (−)-50 (35% yield). The unsaturated model alcohol (+)-44 similarly afforded the Wittig salt (+)-46 in low yield (FIG. 13), whereas the saturated derivative (+)-51 gave phosphonium iodide (+)-53 almost quantitatively.

Figure 14:
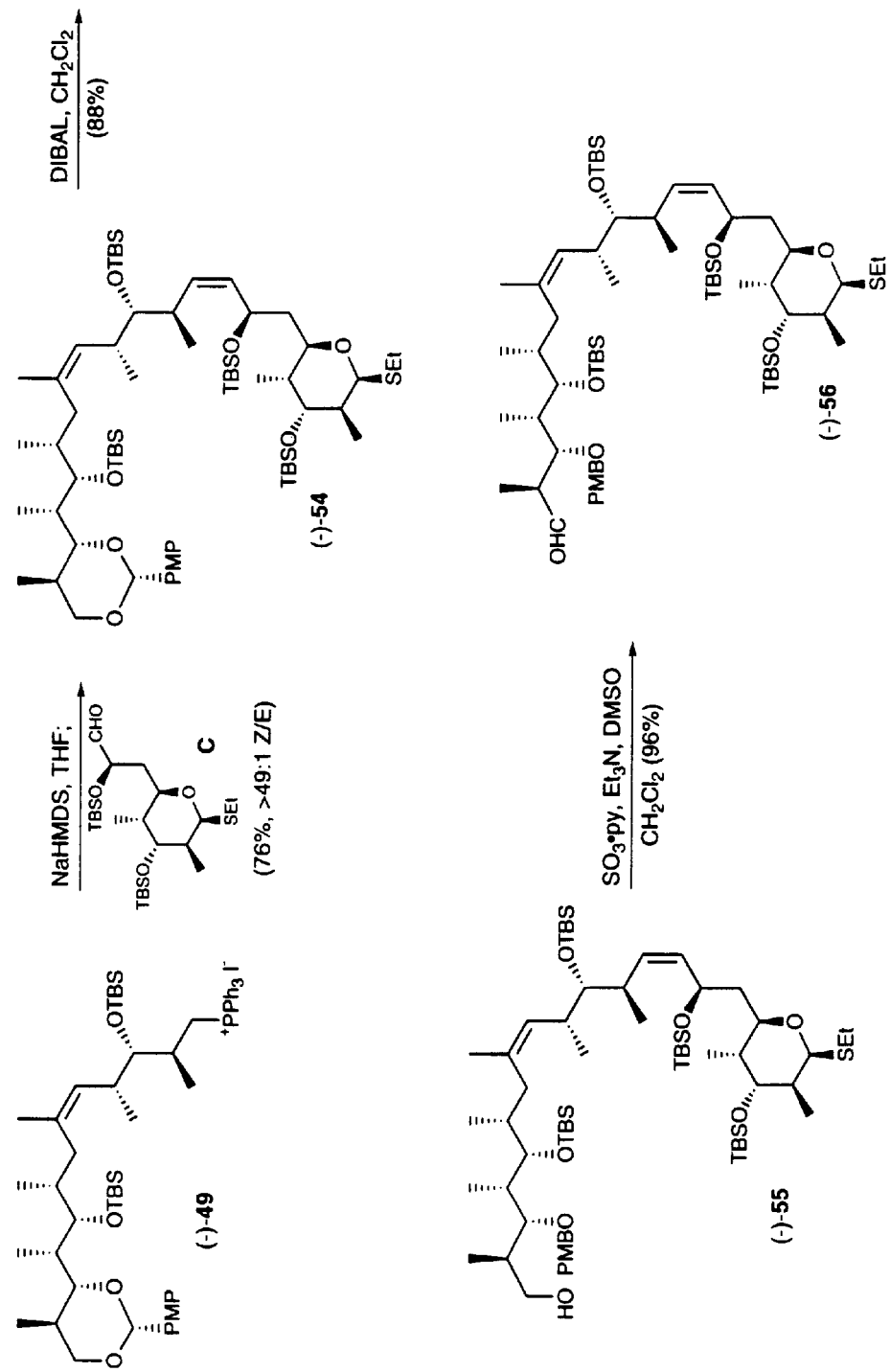
FIG. 14 shows a synthetic scheme for compound 56.
Figure 15:
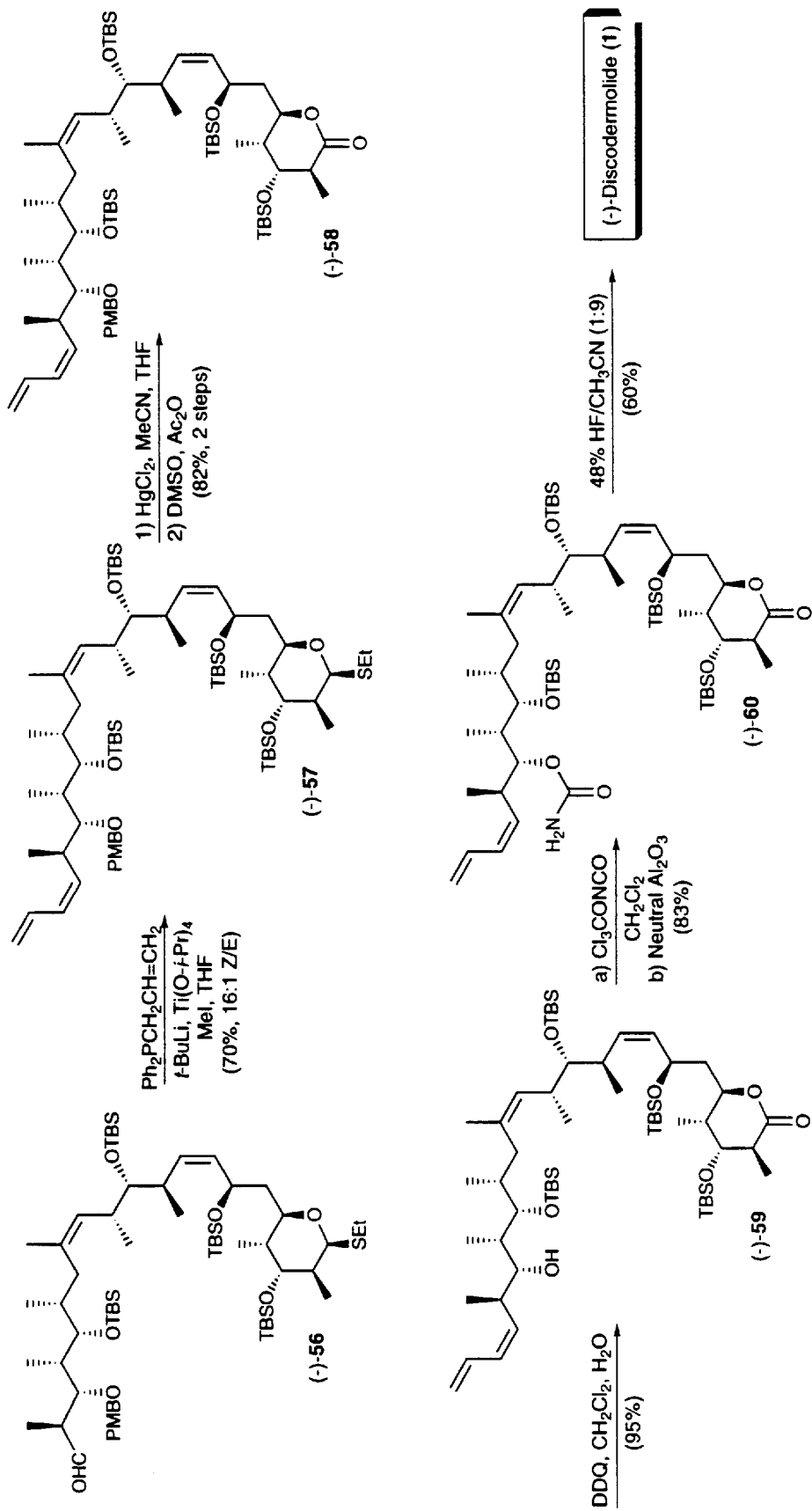
FIG. 15 shows a synthetic scheme for compound 1.

As shown in FIG. 14, assembly of the discodermolide backbone entailed Wittig coupling of aldehyde C with the ylide derived from AB phosphonium salt (−)-49 to install the C(8,9) Z alkene in (−)-54 (>49:1 Z/E, 76% yield). DIBAL reduction (88% yield) followed by oxidation of the resultant primary alcohol (−)-55 then produced aldehyde (−)-56 (96%). The terminal Z diene (−)-57 was elaborated via the Yamamoto protocol in 70% yield with excellent selectivity (16:1 Z/E). After flash chromatography, hydrolysis of the hemithio acetal and mild DMSO/Ac$_2$O oxidation provided lactone (−)-58 in 82% yield for the two steps. Removal of the PMB group (DDQ, CH$_2$Cl$_2$, H$_2$O, 95% yield) and carbamate formation (Cl$_3$CONCO, CH$_2$Cl$_2$, neutral Al$_2$O$_3$, 83%) afforded tris(TBS ether) (−)-60. Final deprotection with 48% HF/CH$_3$CN (1:9) furnished (−)-discodermolide, identical with an authentic sample (FIG. 15).

Preferred processes according to the invention involve contacting a phosphonium salt of formula I with base and an alkylthiol of formula II:

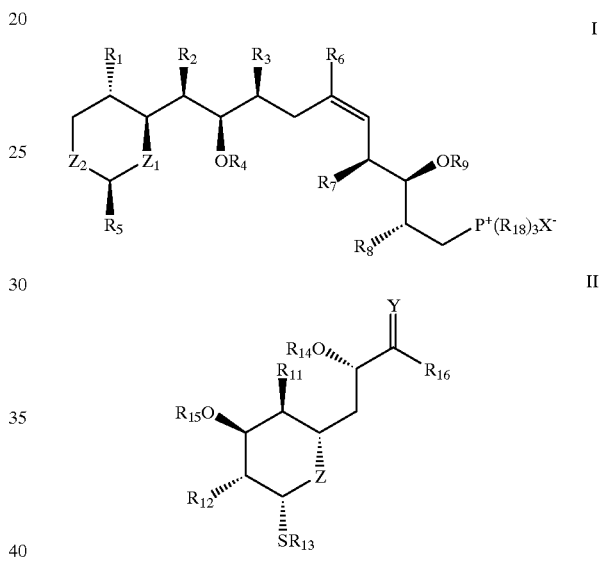

to form a diene of formula III:

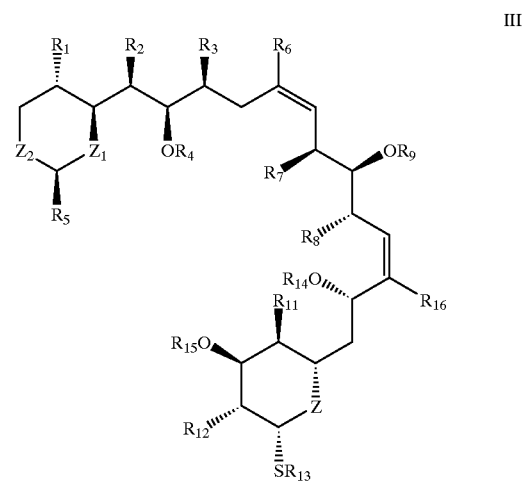

wherein:

R$_1$, R$_2$, R$_3$, R$_6$, R$_7$, R$_8$, R$_{11}$, R$_{12}$ and R$_{13}$ are, independently, C$_1$–C$_{10}$ alkyl;

X is a halogen;

Z, $Z_1$, and $Z_2$ are, independently, O, S or NR';

$R_4$, $R_9$, $R_{14}$, and $R_{15}$ are, independently, acid labile hydroxyl protecting groups;

$R_5$ is $C_6$–$C_{14}$ aryl;

Y is O, S or NR';

R' and $R_{16}$ are, independently, hydrogen or $C_1$–$C_6$ alkyl; and $R_{18}$ is $C_6$–$C_{14}$ aryl.

Such procedures preferably are run in solvents such as tetrahydrofuran at −78° C.–0° C. Suitable bases for such procedures include sodium hexamethyldisilazide, potassium hexamethyldisilazide, and n-butyllithium with hexamethylphosphoramide.

Alkyl groups according to the invention include but are not limited to straight chain and branched chain hydrocarbons such as methyl, ethyl, propyl, pentyl, isopropyl, 2-butyl, isobutyl, 2-methylbutyl, and isopentyl moieties having 1 to about 10 carbon atoms, preferably 1 to about 6 carbon atoms. Cycloalkyl groups are cyclic hydrocarbons having 3 to about 10 carbon atoms such as cyclopentyl and cyclohexyl groups. Heterocycloalkyl groups are cycloalkyl groups which include at least one heteroatom (i.e., an atom which is not carbon, such as O, S, or N) in their cyclic backbone. Alkenyl groups according to the invention are straight chain or branched chain hydrocarbons that include one or more carbon-carbon double bonds. Preferred alkenyl groups are those having 2 to about 10 carbon atoms. Alkyl, cycloalkyl, heterocycloalkyl, and alkenyl groups according to the invention optionally can be unsubtituted or can bear one or more substituents such as, for example, halogen hydroxyl, amine, and epoxy groups.

Aryl groups according to the invention are aromatic and heteroaromatic groups having 6 to about 14 carbon atoms, preferably from 6 to about 10 carbon atoms, including, for example, naphthyl, phenyl, indolyl, and xylyl groups and substituted derivatives thereof, particularly those substituted with amino, nitro, hydroxy, methyl, methoxy, thiomethyl, trifluoromethyl, mercaptyl, and carboxy groups. Alkaryl groups are groups that contain alkyl and aryl portions and are covalently bound to other groups through the alkyl portion, as in a benzyl group.

Protecting groups are known per se as chemical functional groups that can be selectively appended to and removed from functionality, such as hydroxyl and amine groups, present in a chemical compound to render such functionality inert to certain chemical reaction conditions to which the compound is exposed. See, e.g., Greene and Wuts, Protective Groups in Organic Synthesis, 2d edition, John Wiley & Sons, New York, 1991. Numerous hyroxyl protecting groups are known in the art, including the acid-labile t-butyldimethylsilyl, diethylisopropylsilyl, and triethylsilyl groups and the acid-stable aralkyl (e.g., benzyl), triisopropylsilyl, and t-butyldiphenylsilyl groups. Useful amine protecting groups include the allyloxycarbonyl (Alloc), benzyloxycarbonyl (CBz), chlorobenzyloxycarbonyl, t-butyloxycarbonyl (Boc), fluorenylmethoxycarbonyl (Fmoc), isonicotinyloxycarbonyl (i-Noc) groups.

The methods of the invention involve also are directed to the synthesis of alkenes of formula IV:

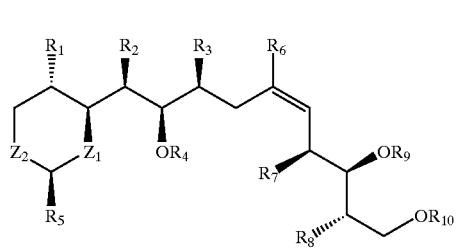

IV by contacting organometallic reagents of formula Va:

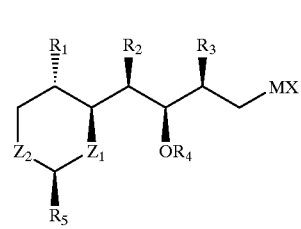

Va with vinyl halides of formula VIa:

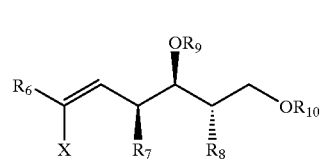

VIa wherein
M is Li, Cu, Mg, or Zn, and
$R_{10}$ is an acid stable hydroxyl protecting group. Alternatively, a vinyl halide of formula Vb:

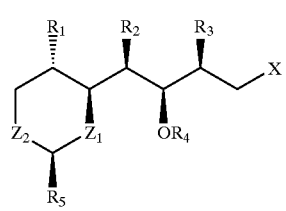

Vb is contacted with an organometallic compound of formula VIb:

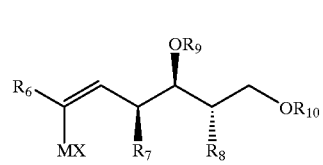

VIb

Such reactions preferably are performed in the presence of a palladium-containing catalyst such as $Pd(PPh_3)_4$, $Pd(Cl_2)$ $(PPh_3)_2$, $Pd(Cl_2)$ $(dppf)_2$.

In yet another aspect, the synthetic methods of the invention are directed to the preparation of lactones having formula VII:

13

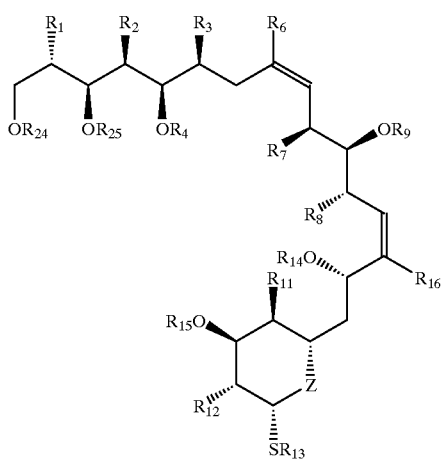

VII by contacting a diene of formula VIIIa:

VIIIa

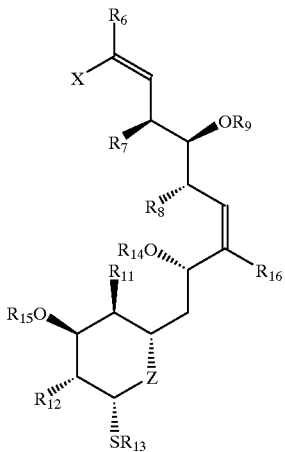

with an organometallic compound having formula Va wherein $R_{24}$ is hydrogen and $R_{25}$ is hydrogen or an acid stable hydroxyl protecting group. Alternatively, an organometallic compound having formula VIIIb is contacted with a vinyl halide having formula Vb.

VIIIb

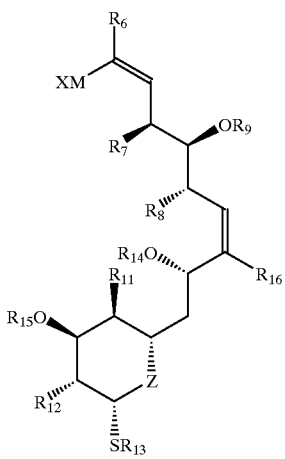

The reaction of compounds having formulas V and VIII preferably is performed in ether in the presence of a palladium- or nickel-containing catalyst.

14

The methods of the invention also involve producing dienes having formula VIIIa by contacting phosphonium salts having formula IX:

IX

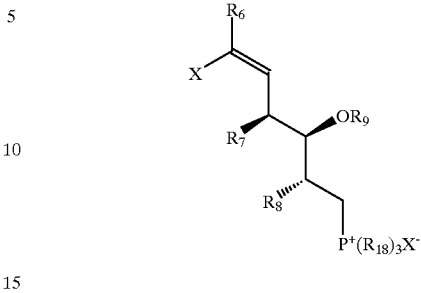

with a base such as sodium hexamethyl disilazide and an alkylthiol compound having formula II. Such procedures preferably are run in solvents such as tetrahydrofuran at −78° C.–0° C. Suitable bases for such procedures include sodium hexamethyldisilazide, potassium hexamethyldisilazide, and n-butyllithium with hexamethylphosphoramide.

Although preferred synthetic methods are those directed to (+)-discodermolide and compounds having like stereochemistry, those skilled in the art will recognize that the methods disclosed herein can be readily adapted to the synthesis of antipodal compounds such as, for example, (−)-discodermolide, and vice versa. All such synthetic methods are within the scope of the present invention.

The present invention provides compounds which mimic the chemical and/or biological activity of the discodermolides. In preferred embodiments, such compounds have formula XI:

XI

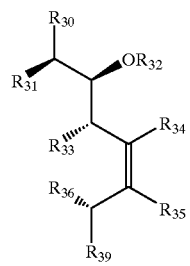

where $R_{30}$ is substituted or unsubstituted $C_1$–$C_{10}$ alkyl or a moiety formula XII or XIII:

XII

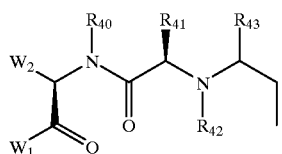

XIII

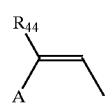

where

A is $C_1$–$C_{20}$ alkyl, —$CH_2NH(T)$ or a moiety of formula XIV:

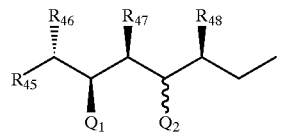

XIV wherein

T is peptide having 1 to about 10 amino acids;

$R_{45}$ is $C_1$–$C_6$ alkenyl, $C_1$–$C_6$ alkyl, $C_6$–$C_{14}$ aryl, $C_2$–$C_{10}$ heterocycloalkyl, $C_3$–$C_{10}$ cycloalkyl, or $C_7$–$C_{15}$ aralkyl; and $R_{49}$, $R_{50}$, and $R_{52}$ are, independently, hydrogen or $C_1$–$C_6$ alkyl.

Some preferred compounds having formula XI are shown in FIGS. 33–36.

The term amino acid as used herein is intended to include all naturally-occurring and synthetic amino acids known in the art. In general, amino acids have structure $H_2N$—$CH$($R_c$)—$C(O)OH$ where $R_c$ is the amino acid side chain. Representative, naturally-occurring side chains are shown in Table 1.

TABLE 1

| | |
|---|---|
| $CH_3$— | $CH_3$—$CH_2$—S—$CH_2$—$CH_2$— |
| HO—$CH_2$— | HO—$CH_2$—$CH_2$— |
| $C_6H_5$—$CH_2$— | $CH_3$—$CH_2(OH)$— |
| HO—$C_6H_5$—$CH_2$— | $HO_2C$—$CH_2$—$NH_2C(O)$—$CH_2$— |
| HO—(phenyl with OH)—$CH_2$— | (azetidine)—H |
| (indole)—$CH_2$— | $HCO_2$—$CH_2$—$CH_2$—<br>$NH_2C(O)$—$CH_2$—$CH_2$—<br>$(CH_3)_2$—CH—<br>$(CH_3)_2$—CH—$CH_2$—<br>$CH_3$—$CH_2$—$CH_2$— |
| (imidazole)—$CH_2$— | $H_2N$—$CH_2$—$CH_2$—$CH_2$—<br>$H_2N$—C(NH)—NH—$CH_2$—$CH_2$—$CH_2$—<br>$H_2N$—C(O)—NH—$CH_2$—$CH_2$—$CH_2$—<br>$CH_3$—$CH_2$—$CH(CH_3)$— |
| HS—$CH_2$—<br>$HO_2C$—$CH(NH_2)$—$CH_2$—S—S—$CH_2$—<br>$CH_3$—$CH_2$—<br>$CH_3$—S—$CH_2$—$CH_2$— | $CH_3$—$CH_2$—$CH_2$—$CH_2$—<br>$H_2N$—$CH_2$—$CH_2$—$CH_2$—$CH_2$— |

$R_{32}$, $R_{40}$, $R_{42}$, $R_{43}$, $R_{46}$, $R_{47}$, and $R_{48}$ are, independently, hydrogen or $C_1$–$C_6$ alkyl;

$R_{41}$ is a side chain of an amino acid;

$W_1$ and $W_2$ are, independently, —$OR_{49}$ or —$NHP_1$;

$P_1$ is hydrogen or an amine protecting group;

$R_{33}$ and $R_{36}$ are, independently, hydrogen, $C_1$–$C_{10}$ alkyl, —$OR_{50}$, =O or together form —$CH_2$—$CH_2$—;

$R_{34}$ and $R_{34}$ are, independently, hydrogen or together form —C(H)=C(H)—C(H)=C(H)—;

$R_{39}$ is —$OR_{51}$ or —$CH_2$—$R_{51}$;

$R_{31}$ and $R_{44}$ are, independently, $C_1$–$C_{10}$ alkyl;

$Q_1$ and $Q_2$ are, independently, hydrogen, —$OR_Q$, —$NHR_{52}$, —OC(=O)$NH_2$ or together form —O—C(O)—NH—;

$R_Q$ is hydrogen or a hydroxyl protecting group;

$R_{51}$ is substituted or unsubstituted $C_6$–$C_{14}$ aryl, tetrahydropyranyl, furanosyl, pyranosyl, $C_3$–$C_{10}$ lactonyl or 2-pyranonyl;

Hydrophobic amino acid side chains are preferred, including the $CH_3$—, $C_6H_5$—$CH_2$—, $CH_3$—$CH_2$—, $CH_3$—S—$CH_2$—$CH_2$—, $(CH_3)_2$—CH—, $(CH_3)_2$—CH—$CH_2$—, $CH_3$—$CH_2$—$CH(CH_3)$—, and $CH_3$—$CH_2$—$CH_2$—$CH_2$— side chains. Peptides according to the invention are linear, branched, or cyclic chemical structures containing at least 2 covalently bound amino acids.

Certain compounds of the invention contain amino groups and, therefore, are capable of forming salts with various inorganic and organic acids. Such salts are also within the scope of this invention. Representative salts include acetate, adipate, benzoate, benzenesulfonate, bisulfate, butyrate, citrate, camphorate, camphorsulfonate, ethanesulfonate, fumarate, hemisulfate, heptanoate, hexanoate, hydrochloride, hydrobromide, hydroiodide, methanesulfonate, lactate, maleate, methanesulfonate, 2-naphthalenesulfonate, nitrate, oxalate, pamoate, persulfate, picrate, pivalate, propionate, succinate, sulfate, tartrate, tosylate, and undecanoate. The salts can be formed by conventional means, such as by reacting the free base form of the product with one or more equivalents of the appropriate acid in a solvent or medium in which the salt is insoluble, or in a solvent such as water which is later removed in vacuo or by freeze drying. The salts also can be formed by exchanging the anions of an existing salt for another anion on a suitable ion exchange resin.

The compounds of the invention can be admixed with carriers, excipients, and/or diluents to form novel compositions. Such compositions can be used in prophylactic, diagnostic, and/or therapeutic techniques. By administering an effective amount of such a composition, prophylactic or therapeutic responses can be produced in a human or some other type mammal. It will be appreciated that the production of prophylactic or therapeutic responses includes the initiation or enhancement of desirable responses, as well as the mitigation, cessation, or suppression of undesirable responses. The compositions of the invention are expected to find use, for example, in the inhibition of undesired cell proliferation (e.g., cancer) and in the inhibition of rejection in organ transplantation procedures. (See, e.g., Longley, et al., *Transplantation* 1991, 52, 650 and 656).

Compositions of the invention can be prepared by any of the methods well known in the pharmaceutical art, for example, as described in *Remington's Pharmaceutical Sciences* (Mack Pub. Co., Easton, Pa., 1980). The compositions can include a compound of the invention as an active ingredient in admixture with an organic or inorganic carrier or excipient suitable, for example, for oral administration. Other suitable modes of administration will be apparent to those skilled in the art. The compound of the invention can be compounded, for example, with the usual non-toxic, pharmaceutically acceptable carriers for tablets, pellets, capsules, solutions, suppositories, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The compound of the invention is included in the pharmaceutical composition in an amount sufficient to produce the desired effect upon the process or condition of diseases.

For oral administration, tablets containing various excipients such as microcrystalline cellulose, sodium citrate, calcium carbonate, dicalcium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tableting purposes. Solid compositions of a similar type may also be employed as fillers in appropriately soluble (e.g., gelatin) capsules; preferred materials in this connection also include lactose or milk sugar as well as high molecular weight polyethylene glycols.

When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, glycerin and various like combinations thereof.

For parenteral administration, suspensions containing a compound of the invention in, for example, aqueous propylene glycol can be employed. The suspensions should be suitably buffered (preferably pH>8) if necessary and the liquid diluent first rendered isotonic. The aqueous suspensions are suitable for intravenous injection purposes. The preparation of such suspensions under sterile conditions is readily accomplished by standard pharmaceutical techniques well-known to those skilled in the art. Additionally, it is possible to administer the compounds of the invention topically and this may preferably be done by way of creams, jellies, gels, pastes, ointments and the like, in accordance with standard pharmaceutical practice.

The compounds of the invention can be employed as the sole active agent in a pharmaceutical composition or can be used in combination with other active ingredients, e.g., other agents useful in diseases or disorders.

The amount of active ingredient that is to be combined with the carrier materials to produce a single dosage form will vary depending upon the host treated and the particular mode of administration. The specific dose level for any particular patient will depend on a variety of factors including the activity of the specific compound employed, the age, body weight, general health, sex, diet, time of administration, route of administration, rate of excretion, drug combination, and the severity of the particular disease undergoing therapy. In some instances, dosage levels below the lower limit of the aforesaid range may be more than adequate, while in other cases still larger doses may be employed without causing any harmful side effects provided that such higher dose levels are first divided into several small doses for administration throughout the day. The concentrations of the active ingredient in therapeutic compositions will vary depending upon a number of factors, including the dosage of the drug to be administered, the chemical characteristics (e.g., hydrophobicity) of the active ingredient, and the route of administration. Typical dose ranges are from about 285 $\mu$g/kg of body weight per day in three divided doses; a preferred dose range is from about 42 $\mu$g/kg to about 171 $\mu$g/kg of body weight per day. The preferred dosage to be administered is likely to depend on such variables as the type and extent of progression of the disease or disorder, the overall health status of the particular patient, the relative biological efficacy of the compound selected, and formulation of the compound excipient, and its route of administration, as well as other factors, including bioavailability, which is in turn influenced by several factors well known to those skilled in the art.

Additional objects, advantages, and novel features of this invention will become apparent to those skilled in the art upon examination of the following examples thereof, which are not intended to be limiting.

All reactions were carried out in oven-dried or flame-dried glassware under an argon atmosphere, unless otherwise noted. All solvents were reagent grade. Diethyl ether and tetrahydrofuran (THF) were freshly distilled from sodium/benzophenone under argon before use. Dichloromethane, benzene and diisopropyl amine were freshly distilled from calcium hydride before use. Triethylamine and diisopropylethylamine were distilled from calcium hydride and stored over potassium hydroxide. Hexamethylphosphoramide was freshly distilled from calcium hydride. Anhydrous pyridine, dimethylformamide and dimethyl sulfoxide were purchased from Aldrich and used without purification. n-Butyllithium and t-butyllithium were purchased from Aldrich and standardized by titration with diphenylacetic acid.

Unless stated otherwise all reactions were magnetically stirred and monitored by thin layer chromatography using 0.25 mm E. Merck pre-coated silica gel plates. Flash column chromatography was performed with the indicated solvents using silica gel-60 (particle size 0.040–0.062 mm) supplied by E. Merck. Yields refer to chromatographically and spectroscopically pure compounds, unless otherwise stated.

All melting points were determined on a Bristoline heated-stage microscope or a Thomas-Hoover apparatus and are corrected. The IR and NMR were obtained for $CHCl_3$ and $CDCl_3$ solutions respectively unless otherwise noted. Infrared spectra were recorded with a Perkin-Elmer Model 283B spectrometer using polystyrene as an external standard. Proton NMR spectra were recorded on a Bruker AM-500 spectrometer. Carbon-13 NMR spectra were recorded on a Bruker AM-500 or AM-250 spectrometer. Chemical shifts are reported relative to internal tetramethylsilane (d 0.00) for proton and chloroform δ 77.0) or benzene (δ 128.0) for carbon-13. Optical rotations were obtained with a Perkin-Elmer model 241 polarimeter in the solvent indicated. High-resolution mass spectra were obtained at the University of Pennsylvania Mass Spectrometry Service Center on either a VG micromass 70/70H high resolution double-focusing electron impact/chemical ionization spectrometer or a VG ZAB-E spectrometer. Microanalyses were performed by Robertson Laboratories, Madison, N.J. Single-crystal X-ray diffraction structure determination were performed at the University of Pennsylvania using an Enraf Nonius CAD-4 automated diffractometer. High performance liquid chromatography (HPLC) was performed using a Ranin component analytical/semi-prep system.

EXAMPLE 1

Alcohol (−)-8 p-Methoxybenzyl alcohol (200 g, 1.45 mol) was added to a suspension of NaH (60% in mineral oil; 5.82 g, 0.146 mol) in anhydrous ether (450 mL) over 1 h at room temperature. The mixture was stirred for 1 h and cooled to 0° C. Trichloroacetonitrile (158 mL, 1.58 mol) was then introduced over 80 min. After 1.5 h the solution was concentrated with the water bath temperature maintained below 40° C. The residue was treated with a mixture of pentane (1.5 L) and MeOH (5.6 mL), stirred at room temperature for 30 min, and filtered through a short Celite column. Concentration gave the trichloroimidate (394.3 g) as a red oil which was used without further purification.

A solution of (R)-(−)-Roche ester (124.7 g, 1.06 mol) in $CH_2Cl_2$/cyclohexane (1:2, 1.5 L) was cooled to 0° C. and treated with trichloroimidate (364.3 g) and PPTS (13.3 g, 52.9 mmol). After 3 h, the mixture was warmed to room temperature, stirred for 40 h, and concentrated. Filtration through a short silica column (20% ethyl acetate/hexane) afforded the ester (303.5 g) as a slight yellow oil.

The ester (303.5 g) was divided into three portions for the next reaction. In each preparation, solution of crude ester (112.8 g) in anhydrous THF (1.0 L) was cooled to 0° C. and $LiAlH_4$ (1.0 M in THF, 560 mL, 0.560 mol) was added over 1 h. The mixture was warmed gradually to room temperature and stirred for 24 h. After dilution with ether (1.0 L) the mixture was cooled to 0° C. and quenched carefully with saturated aqueous Rochelle's salt (20 mL). The resultant mixture was then transferred to a 4-L flask, diluted with ether (1.0 L), and treated with additional Rochelle's solution (ca. 300 mL) with shaking until a solid precipitated. The solution was filtered, concentrated, and the residue (including the aqueous layer) was diluted with ether (700 mL), dried over $Na_2SO_4$, filtered and concentrated. The crude products of the three reactions were combined and distilled under vacuum, furnishing (−)-8 (142.7 g, 740% yield for two steps) as a colorless oil: $[\alpha]^{23}_D$ −16.9° (c 1.28, $CHCl_3$); IR ($CHCl_3$) 3510 (m), 3015 (s), 2965 (s), 2940 (s), 2920 (s), 2870 (s), 2840 (m), 1618 (s), 1590 (m), 1517 (s), 1470 (s), 1445 (m), 1423 (m), 1365 (m), 1305 (s), 1250 (s), 1178 (s), 1092 (s), 1037 (s), 826 (m), 814 (m), 718 (w), 710 (w) $cm^{-1}$; $^1H$ NMR (500 MHZ, $CDCl_3$) d 7.23 (d, J=8.6 Hz, 2H), 6.86 (d, J=8.6 Hz, 2H), 4.43 (ABq, $J_{AB}$=11.7 Hz, $\Delta\delta_{AB}$=13.2 Hz, 2H), 3.78 (s, 3H), 3.61–3.54 (m, 2H), 3.53 (ddd, J=9.1, 4.7, 0.8 Hz, 1H), 3.38 (dd, J=9.1, 7.9 Hz, 1H), 2.60 (br s, 1H), 2.08–1.98 (m, 1H), 0.90 (d, J=7.0 Hz, 3H); $^{13}C$ NMR (125 MHZ, $CDCl_3$) d 159.2, 130.2, 129.2, 113.8, 75.0, 73.0, 67.7, 55.2, 35.6, 13.4; high resolution mass spectrum (CI, $NH_3$) m/z 210.1252 [M$^+$; calcd for $C_{12}H_{18}O_3$: 210.1256].

Anal. Calcd for $C_{12}H_{18}O_3$: C, 68.54; H, 8.63. Found: C, 68.41; H, 8.60.

EXAMPLE 2

Aldol (+)-10

A solution of DMSO (40.0 mL, 564 mmol) in $CH_2Cl_2$ (1.0 L) was cooled to −78° C. and oxalyl chloride (23.0 mL, 263 mmol) was added over 1 h. After an additional 15 min, a cooled (−78° C.) solution of alcohol (−)-8 (38.0 g, 181 mmol) in $CH_2Cl_2$ (50 mL) was introduced via a cannula over 15 min (20 mL rinse) and the resultant milky mixture was stirred 0.5 h further at −78° C. i-$Pr_2NEt$ (150 mL, 861 mmol) was then added over 15 min. The mixture was stirred for 30 min, slowly warmed to room temperature (70 min), and quenched with aqueous $NaHSO_4$ (1.0 M, 1.0 L). The organic phase was concentrated, diluted with ether (500 mL), washed with water (6×500 mL), dried over $MgSO_4$, filtered and concentrated to give the corresponding aldehyde (38.0 g) as a colorless oil.

A solution of oxazolidinone (+)-9 (44.3 g, 190 mmol) in $CH_2Cl_2$ (500 mL) was cooled to 0° C. n-$Bu_2BOTf$ (1.0 M in $CH_2Cl_2$, 199.0 mL, 199 mmol) was introduced over 0.5 h, followed by addition of $NEt_3$ (30.2 mL, 217 mmol) over 10 min. The mixture was stirred at 0° C. for 0.5 h and cooled to −78° C. A precooled (−78° C.) solution of the above aldehyde in $CH_2Cl_2$ (100 mL) was then added via a cannula over 30 min (2×20 mL rinse). After 2 h at −78° C. and 2 h at 0° C., the reaction was quenched with pH 7 phosphate buffer (200 mL). The mixture was slowly treated with a solution of 30% $H_2O_2$ in MeOH (1:2, 600 mL) at 0° C., stirred overnight at room temperature, and concentrated. The residue was extracted with ethyl acetate (3×250 mL) and the combined extracts were washed with saturated aqueous $NaHCO_3$ and water (500 mL each), dried over $MgSO_4$, filtered and concentrated. Flash chromatography (30% ethyl acetate/hexane) provided (+)-10 (70.9 g, 89% yield from 8) as a colorless oil: $[\alpha]^{23}_D$ +278° (c 0.49, $CHCl_3$); IR ($CHCl_3$) 3470 (w, br), 3020 (m), 2980 (m), 2940 (m), 2920 (m), 2880 (m), 1790 (s), 1705 (m), 1620 (m), 1590 (w), 1520 (m), 1485 (w), 1460 (m), 1390 (m), 1360 (m), 1305 (w), 1230 (br, s), 1110 (m), 1080 (m), 1035 (m), 985 (m), 970 (m), 820 (w), 695 (w) $cm^{-1}$; $^1H$ NMR (500 MHZ, $CDCl_3$) d 7.33–7.30 (m, 2H), 7.27–7.19 (m, 5H), 6.85 (d, J=8.7 Hz, 2H), 4.67–4.63 (m, 1H), 4.42 (apparent s, 2H), 4.14 (apparent d, J=5.0 Hz, 2H), 3.93 (qd, J=6.9, 3.4 Hz, 1H), 3.85 (ddd, J=8.2, 3.1, 3.1 Hz, 1H), 3.78 (s, 3H), 3.69 (d, J=2.8 Hz, 1H), 3.54 (apparent t, J=9.3 Hz, 1H), 3.54 (dd, J=21.1, 9.2 Hz, 1H), 3.28 (dd, J=13.4, 3.2 Hz, 1H), 2.76 (dd, J=13.4, 9.6 Hz, 1H), 1.98–1.93 (m, 1H), 1.25 (d, J=6.9 Hz, 3H), 0.94 (d, J=7.0 Hz, 3H); $^{13}C$ NMR (125 MHZ, $CDCl_3$) d 176.1, 159.2, 153.0, 135.3, 129.9, 129.3, 129.2, 128.8, 127.2, 113.7, 75.3, 74.5, 73.1, 66.0, 55.5, 55.2, 40.6, 37.7, 35.9, 13.5, 9.7; high resolution mass spectrum (CI, $NH_3$) m/z 442.2243 [(M+H)$^+$; calcd for $C_{25}H_{32}NO_6$: 442.2229].

Anal. Calcd for $C_{25}H_{31}NO_6$: C, 68.01; H, 7.08. Found: C, 67.81; H, 7.26.

EXAMPLE 3

Common Precursor (+)-5

A suspension of N,O-Dimethylhydroxylamine hydrochloride (46.9 g, 481 mmol) in THF (250 mL) was cooled to 0° C. and AlMe$_3$ (2.0 M in hexane, 240 mL, 480 mmol) was added over 30 min. The resultant solution was warmed to room temperature, stirred for 0.5 h and then cooled to −30° C. A solution of oxazolidinone (+)-10 (70.9 g, 161 mmol) in THF (150 mL) was introduced over 20 min via cannula (20 mL rinse).

After 3 h, the solution was poured slowly into a mixture of aqueous HCl (1.0 N, 1.2 L) and CH$_2$Cl$_2$ (1.0 L) at 0° C. and the mixture was shaken vigorously for 1 h. The aqueous phase was extracted with CH$_2$Cl$_2$ (2×500 mL) and the combined organic extracts were washed with water (3×1.0 L), dried over MgSO$_4$, filtered and concentrated. The crude material was taken up in ethyl acetate/hexane (1:3, 150 mL) with vigorous stirring to precipitate most of the chiral auxiliary. Filtration, concentration and flash chromatography (20% acetone/hexane) afforded (+)-5 (46.2 g, 88% yield) as a colorless oil: $[\alpha]^{23}_D$ +144° (c 0.41, CHCl$_3$); IR (CHCl$_3$) 3470 (m, br), 3010 (s), 2975 (s), 2945 (s), 2915 (s), 2870 (s), 2845 (m), 1680 (s), 1590 (w), 1515 (s), 1465 (s), 1425 (m), 1390 (m), 1365 (m), 1310 (m), 1250 (s), 1180 (s), 1150 (m), 1090 (s), 1040 (s), 1000 (s), 825 (m) cm$^{-1}$; $^1$H NMR (500 MHZ, CDCl$_3$) d 7.25 (d, J=8.6 Hz, 2H), 6.86 (d, J=8.7 Hz, 2H), 4.44 (ABq, J$_{AB}$=11.6 Hz, Δδ$_{AB}$=17.1 Hz, 2H), 3.95 (d, J=2.8 Hz, 1H), 3.79 (s, 3H), 3.70 (ddd, J=8.2, 3.2, 3.2 Hz, 1H), 3.66 (s, 3H), 3.62 (dd, J=9.0, 4.0 Hz, 1H), 3.53 (dd, J=9.1, 5.9 Hz, 1H), 3.17 (s, 3H), 3.04 (m, 1H), 1.91–1.84 (m, 1H), 1.17 (d, J=7.0 Hz, 3H), 0.98 (d, J=6.9 Hz, 3H); $^{13}$C NMR (125 MHZ, CDCl$_3$) d 178.0, 159.0, 130.6, 129.1, 113.7, 113.6, 73.8, 72.8, 72.6, 61.3, 55.1, 36.5, 36.0, 14.2, 10.4; high resolution mass spectrum (CI, NH$_3$) m/z 326.1962 [(M+H)$^+$; calcd for C$_{17}$H$_{28}$NO$_5$: 326.1967].

Anal. Calcd for C$_{17}$H$_{27}$NO$_5$: C, 62.74; H, 8.36. Found: C, 62.74; H, 8.24.

EXAMPLE 4

Weinreb Amide (−)-11

A mixture of common precursor (+)-5 (337.3 mg, 1.04 mmol), 4 Å molecular sieves (344 mg), and CH$_2$Cl$_2$ (10 mL) was cooled to 0° C. and treated with DDQ (310.3 mg, 1.37 mmol). After 1.5 h, the mixture was filtered through a short Celite column (50% ethyl acetate/hexane). The filtrate was washed with saturated aqueous NaHCO$_3$ and water (100 mL each), dried over MgSO$_4$, filtered and concentrated. Flash chromatography (30% ethyl acetate/hexane) provided (−)-11 (255.6 mg, 76% yield) as a colorless oil: $[\alpha]^{23}_D$ −339° (c 0.520, CHCl$_3$); IR (CHCl$_3$) 3010 (s), 2970 (s), 2940 (m), 2880 (m), 2840 (m), 1663 (s), 1620 (s), 1592 (w), 1520 (s), 1466 (s), 1447 (m), 1425 (m), 1393 (s), 1375 (s), 1307 (m), 1253 (s), 1178 (s), 1120 (s), 1083 (s), 1035 (s), 1015 (m), 1000 (m), 930 (m), 830 (m), 700 (w), 660 (w), 620 (w) cm$^{-1}$; $^1$H NMR (500 MHZ, CDCl$_3$) d 7.41 (d, J=8.8 Hz, 2H), 6.87 (d, J=8.8 Hz, 2H), 5.46 (s, 1H), 4.04 (dd, J=11.3, 4.7 Hz, 1H), 3.82 (dd, J=9.8, 6.5 Hz, 1H), 3.79 (s, 3H), 3.71 (s, 3H), 3.51 (apparent t, J=11.2 Hz, 1H), 3.19 (s, 3H), 3.21–3.14 (m, 1H), 1.98–1.92 (m, 1H), 1.27 (d, J=7.0 Hz, 3H), 0.75 (d, J=6.8 Hz, 3H); $^{13}$C NMR (125 MHZ, CDCl$_3$) d 175.8, 159.8, 131.2, 127.6, 113.5, 100.7, 82.8, 72.8, 61.3, 55.3, 39.0, 33.8, 32.6, 13.1, 12.4; high resolution mass spectrum (CI, NH$_3$) m/z 323.1736 [M$^+$; calcd for C$_{17}$H$_{25}$NO$_5$: 323.1732].

Anal. Calcd for C$_{17}$H$_{25}$NO$_5$: C, 63.14; H, 7.79. Found: C, 63.18; H, 7.74.

EXAMPLE 5

Aldehyde (−)-12

A solution of amide (−)-11 (2.07 g, 6.40 mmol) in THF (70 mL) was cooled to −78° C. and LiAlH$_4$ (1.0 M in THF, 3.40 mL, 3.40 mmol) was added over 15 min. After 10 min at −78° C. and 10 min at 0° C., the mixture was quenched with MeOH (1.0 mL), and partitioned between ethyl acetate and saturated aqueous Rochelle's salt (100 mL each). The organic phase was washed with brine (100 mL), dried over MgSO$_4$, filtered and concentrated. Flash chromatography (15% ethyl acetate/hexane) gave (−)-12 (1.38 g, 80% yield) as a colorless oil: $[\alpha]^{23}_D$ −7.8° (c 0.46, CHCl$_3$); IR (CHCl$_3$) 3015 (m), 2970 (m), 2940 (m), 2840 (m), 1735 (s), 1725 (s), 1615 (m), 1590 (w), 1520 (s), 1460 (s), 1390 (m), 1370 (m), 1305 (m), 1250 (s), 1170 (s), 1115 (s), 1085 (s), 1035 (s), 990 (m), 960 (m), 830 (m) cm$^{-1}$; $^1$H NMR (500 MHZ, CDCl$_3$) d 9.74 (apparent s, 1H), 7.32 (d, J=8.8 Hz, 2H), 6.84 (d, J=8.7 Hz, 2H), 5.46 (s, 1H), 4.13 (dd, J=11.5, 4.8 Hz, 1H), 4.05 (dd, J=10.4, 2.6 Hz, 1H), 3.77 (s, 3H), 3.56 (apparent t, J=11.1 Hz, 1H), 2.56 (qd, J=7.1, 2.6 Hz, 1H), 2.15–2.03 (m, 1H), 1.23 (d, J=7.1 Hz, 3H), 0.80 (d, J=6.7 Hz, 3H); $^{13}$C NMR (125 MHZ, CDCl$_3$) d 204.0, 159.9, 130.7, 127.2, 113.5, 100.9, 81.6, 72.8, 55.2, 47.4, 30.3, 11.9, 7.1; high resolution mass spectrum (CI, NH$_3$) m/z 265.1432 [(M+H)$^+$; calcd for C$_{15}$H$_{21}$O$_4$: 265.1439].

EXAMPLE 6

Aldol (+)-13

A solution of oxazolidinone (+)-9 (21.6 g, 92.7 mmol) in CH$_2$Cl$_2$ (200 mL) was cooled to 0° C. and n-Bu$_2$BOTf (1.0 M in CH$_2$Cl$_2$, 86.1 mL, 86.1 mmol) was added over 0.5 h, followed by addition of NEt$_3$ (15.7 mL, 112.5 mmol) over 10 min. The mixture was stirred at 0° C. for 1 h and cooled to −78° C. A solution of aldehyde (−)-12 (17.5 g, 66.2 mmol) in CH$_2$Cl$_2$ (50 mL) was added over 10 min. After additional 20 min at −78° C. and 1 h at 0° C., the reaction was quenched with pH 7 phosphate buffer (100 mL) and MeOH (300 mL), then slowly treated with a solution of 30% H$_2$O$_2$ in MeOH (1:1, 100 mL) at 0° C. After 1 h, saturated aqueous Na$_2$S$_2$O$_3$ (100 mL) was added. The mixture was concentrated and the residue was extracted with ethyl acetate (3×250 mL). The combined extracts were washed with saturated aqueous Na$_2$S$_2$O$_3$, aqueous NaHCO$_3$ (10%), brine (200 mL each), dried over MgSO$_4$, filtered and concentrated. Flash chromatography (10% ethyl acetate/hexane) provided (+)-13 (26.3 g, 80% yield) as white crystals: mp 98–100° C.; $[\alpha]^{23}_D$ +13.5° (c 1.19, CHCl$_3$); IR (CHCl$_3$) 3690 (w), 3520 (w, br), 3020 (m), 2980 (m), 2940 (m), 2880 (w), 2850 (m), 1790 (s), 1695 (m), 1620 (m), 1595 (w), 1525 (m), 1505 (w), 1490 (w), 1465 (m), 1390 (s), 1365 (m), 1310 (m), 1260–1210 (m, br), 1175 (m), 1120 (s), 1085 (m), 1040 (m), 1020 (m), 985 (m), 970 (m), 930 (w), 830 (m), 700 (m) cm$^{-1}$; $^1$H NMR (500 MHZ, CDCl$_3$) d 7.35 (d, J=8.7 Hz, 2H), 7.31 (d, J=7.6 Hz, 2H), 7.27 (d, J=7.2 Hz, 1H), 7.19 (d, J=7.7 Hz, 2H), 6.84 (d, J=8.7 Hz, 2H), 5.45 (s, 1H), 4.67–4.62 (m, 1H), 4.14 (apparent d, J=5.3 Hz, 2H), 4.08 (dd, J=11.4, 4.8 Hz, 1H), 4.07 (apparent t, J=4.1 Hz, 1H), 4.04–3.99 (m, 1H), 3.76 (s, 3H), 3.61 (dd, J=9.9, 2.2 Hz, 1H), 3.51 (apparent t, J=11.1 Hz, 1H), 3.33 (d, J=1.3 Hz, 1H), 3.21 (dd, J=13.4, 3.4 Hz, 1H), 2.76 (dd, J=13.4, 9.4 Hz, 1H), 2.12–2.06 (m, 1H), 1.92–1.86 (m, 1H), 1.31 (d, J=6.9 Hz, 3H), 1.07 (d, J=7.0 Hz, 3H), 0.74 (d, J=6.7 Hz, 3H); $^{13}$C NMR (125 MHZ, CDCl$_3$) d 177.1, 160.0, 152.7, 135.0, 131.0, 129.4, 128.9, 127.40, 127.39, 113.6, 101.2, 85.8, 74.5, 73.0, 66.0, 55.2, 54.9, 39.8, 37.7, 35.7, 30.4, 12.8, 11.7, 7.8; high resolution mass spectrum (CI, NH$_3$) m/z 497.2410 [M$^+$; calcd for C$_{28}$H$_{35}$NO$_7$: 497.2413].

Anal. Calcd for C$_{28}$H$_{35}$NO$_7$: C, 67.58; H, 7.09. Found: C, 67.42; H, 7.02.

EXAMPLE 7

Acetal (+)-14

A solution of alcohol (+)-13 (26.3 g, 52.9 mmol) and 2,6-lutidine (11.1 mL, 95.3 mmol) in $CH_2Cl_2$ (150 mL) was cooled to $-20°$ C. and TBSOTf (20.5 mL, 79.3 mmol) was added over 30 min. After additional 2 h at 0° C., the mixture was diluted with ether (300 mL), washed with aqueous $NaHSO_4$ (1.0 M, 200 mL), brine (200 mL), dried over $MgSO_4$, filtered and concentrated. Flash chromatography (gradient elution, 5%→10% ethyl acetate/hexane) afforded (+)-14 (32.4 g, 100% yield) as a colorless oil: $[\alpha]^{23}_D$ +20.3° (c 1.32, $CHCl_3$); IR ($CHCl_3$) 3025 (m), 2970 (m), 2940 (m), 2864 (m), 1788 (s), 1705 (m), 1620 (m), 1597 (w),1524 (m), 1503 (w), 1470 (m), 1447 (w), 1430 (w), 1395 (s), 1358 (m), 1307 (m), 1255 (s), 1135 (m), 1120 (s), 1075 (m), 1030 (m), 985 (m), 976 (m), 930 (m), 865 (m), 838 (s), 813 (m), 790 (m), 700 (m) $cm^{-1}$; $^1$H NMR (500 MHZ, $CDCl_3$) d 7.38 (d, J=8.7 Hz, 2H), 7.30–7.12 (m, 5H), 6.82 (d, J=8.7 Hz, 2H), 5.44 (s, 1H), 4.30 (dddd, J=13.4, 7.3, 5.1, 5.1 Hz, 1H), 4.11 (dd, J=7.1, 4.0 Hz, 1H), 4.02 (dd, J=11.2, 4.7 Hz, 1H), 3.97 (dq, J=7.0, 7.0 Hz, 1H), 3.80 (dd, J=25 8.9, 2.3 Hz, 1H), 3.740 (apparent t, J=4.9 Hz, 1H), 3.738 (s, 3H), 3.48 (apparent t, J=11.1 Hz, 1H), 3.27 (apparent t, J=8.2 Hz, 1H), 3.15 (dd, J=13.4, 3.2 Hz, 1H), 2.59 (dd, J=13.4, 9.8 Hz, 1H), 2.05 (apparent qd, J=7.4, 4.2 Hz, 1H), 2.02–1.94 (m, 1H), 1.19 (d, J=6.9 Hz, 1H), 1.04 (d, J=7.5 Hz, 3H), 0.92 (s, 9H), 0.73 (d, J=6.7 Hz, 3H), 0.05 (s, 3H), 0.04 (s, 3H); $^{13}$C NMR (125 MHZ, $CDCl_3$) d 175.6, 159.9, 152.4, 135.5, 132.0, 129.4, 128.8, 127.8, 127.2, 113.4, 100.7, 80.7, 74.6, 73.1, 65.3, 55.3, 55.2, 41.4, 40.9, 37.4, 30.6, 26.0, 18.1, 15.0, 12.7, 11.5, −4.0, −4.6; high resolution mass spectrum (CI, $NH_3$) m/z 612.3340 [(M+H)$^+$; calcd for $C_{34}H_{50}NO_7Si$: 612.3356].

Anal. Calcd for $C_{34}H_{49}NO_7Si$: C, 66.74; H, 8.07. Found: C, 66.69; H, 7.98.

EXAMPLE 8

Alcohol (−)-15

A solution of acetal (+)-14 (32.0 g, 52.3 mmol) in THF (600 mL) was cooled to −30° C and EtOH (6.14 mL, 105 mmol) was added, followed by addition of $LiBH_4$ (2.0 M in THF, 52.3 mL, 105 mmol) over 15 min. After additional 1 h at 0° C. and 12 h at room temperature, the mixture was diluted with ether (1.0 L), quenched carefully with aqueous NaOH (1.0 N, 200 mL) and stirred for 2 h at room temperature. The layers were separated and the organic phase was washed with brine (500 mL), dried over $Na_2SO_4$, filtered and concentrated. Flash chromatography (20% ethyl acetate/hexane) provided (−)-15 (18.7 g, 81% yield) as a colorless oil: $[\alpha]^{23}_D$ −36.1° (c 1.15, $CHCl_3$); IR ($CHCl_3$) 3630 (w), 3480 (w, br), 3010 (m), 2960 (s), 2940 (s), 2885 (m) 2860 (s), 1620 (m), 1594 (w), 1523 (s), 1468 (s), 1445 (w), 1430 (w), 1395 (m), 1365 (m), 1307 (m), 1255 (s), 1175 (m), 1165 (m),1150 (m), 1120 (s), 1080 (s), 1030 (s), 990 (m), 968 (m), 910 (s), 860 (m), 833 (s), 700 (m), 645 (m) $cm^{-1}$; $^1$H NMR (500 MHZ, $CDCl_3$) d 7.36 (d, J=8.7 Hz, 2H), 6.85 (d, J=8.8 Hz, 2H), 5.38 (s, 1H), 4.08 (dd, J=11.2, 4.7 Hz, 1H), 3.84 (dd, J=6.7, 1.9 Hz, 1H), 3.77 (s, 3H), 3.53 (dd, J=9.9, 1.8 Hz, 1H), 3.55–3.52 (m, 1H), 3.47 (apparent t, J=11.1 Hz, 1H), 3.44 (dd, J=10.3, 6.2 Hz, 1H), 2.08–1.97 (m, 2H), 1.94 (dqd, J=7.1, 7.1, 1.7 Hz, 1H), 1.76 (br s, 1H), 1.02 (d, J=7.1 Hz, 3H), 0.88 (s, 9H), 0.84 (d, J=6.9 Hz, 3H), 0.73 (d, J=6.7 Hz, 3H), 0.03 (s, 3H), 0.00 (s, 3H); $^{13}$C NMR (125 MHZ, $CDCl_3$) d 159.8, 131.4, 127.3, 113.5, 101.0, 82.9, 74.3, 73.3, 66.3, 55.2, 38.7, 37.8, 30.7, 26.1, 18.3, 12.2, 11.1, 10.7, −4.0, −4.2; high resolution mass spectrum (CI, $NH_3$) m/z 439.2889 [(M+H)$^+$; calcd for $C_{24}H_{43}O_5Si$: 439.2879].

Anal. Calcd for $C_{24}H_{42}O_5Si$: C, 65.71; H, 9.65. Found: C, 65.51; H 9.54.

EXAMPLE 9

Tosylate (−)-16

A solution of alcohol (−)-15 (5.00 g, 11.4 mmol) in anhydrous pyridine (30 mL) was cooled to 0° C. and treated with TsCl (3.91 g, 20.5 mmol). After 30 min at 0° C. and 5 h at room temperature, the reaction was quenched with saturated aqueous $NaHCO_3$ (20 mL). The mixture was diluted with ether (200 mL), washed with aqueous $NaHSO_4$ (1.0 M), aqueous $NaHCO_3$ (10%), brine (200 mL each), dried over $MgSO_4$, filtered and concentrated. Flash chromatography (10% ethyl acetate/hexane) provided (−)-15 (6.76 g, 100% yield) as white solid: mp 71–72° C.; $[\alpha]^{23}_D$ −23.2° (c 1.42, $CHCl_3$); IR ($CHCl_3$) 3020 (m), 3000 (m), 2960 (s), 2935 (s), 2880 (m), 2855 (s), 1617 (m), 1600 (m), 1590 (m), 1518 (m), 1495 (w), 1462 (s), 1390 (m), 1360 (s), 1302 (m), 1250 (s), 1190 (s), 1178 (s), 1120 (s), 1098 (s), 1085 (s), 1070 (s, 1032 (s), 963 (s), 900 (m), 830 (s), 810 (s), 653 (m); $^1$H NMR (500 MHZ, $CDCl_3$) d 7.70 (d, J=8.3 Hz, 2H), 7.34 (d, J=8.7 Hz, 2H), 7.25 (d, J=8.8 Hz, 2H), 6.86 (d, J=8.7 Hz, 2H), 5.36 (s, 3H), 4.07 (dd, J=11.2, 4.7 Hz, 1H), 3.85 (dd, J=7.3, 2.7 Hz, 1H), 3.79 (s, 3H), 3.71 (dd, J=7.1, 1.7 Hz, 1H), 3.48 (dd, J=9.9, 1.4 Hz, 1H), 3.45 (apparent t, J=11.1 Hz, 1H), 2.40 (s, 3H), 2.15 (dqd, J=13.9, 7.0, 1.7 Hz, 1H), 2.05–1.96 (m, 1H), 1.83 (dqd, J=7.1, 7.1, 1.6 Hz, 1H), 0.94 (d, J=7.1 Hz, 3H), 0.82 (s, 9H), 0.81 (d, J=7.7 Hz, 3H), 0.69 (d, J=6.7 Hz, 3H), −0.04 (s, 3H), −0.11 (s, 3H); $^{13}$C NMR (125 MHZ, $CDCl_3$) d 159.8, 144.6, 133.2, 131.3, 129.7, 127.9, 127.3, 113.5, 100.9, 82.0, 73.7, 73.2, 73.0, 55.2, 38.4, 35.5, 30.6, 26.0, 21.6, 18.3, 12.2, 10.6, 10.3, −3.9, −4.3; high resolution mass spectrum (FAB, NBA) m/z 593.2955 [(M+H)$^+$; calcd for $C_{31}H_{49}O_7SSi$: 593.2968].

EXAMPLE 10

Fragment (−)-A

From Tosylate (−)-16: A solution of Tosylate (−)-16 (6.76 g, 11.4 mmol) in anhydrous DMF (50 mL) was treated with NaI (17.1 g, 114.0 mmol), heated at 60° C. for 1.5 h, and cooled to room temperature. The mixture was diluted with ether (200 mL), washed with water (200 mL), saturated aqueous $Na_2S_2O_3$ (100 mL), brine (200 mL), dried over $MgSO_4$, filtered and concentrated. Flash chromatography (3% ethyl acetate/hexane) provided (−)-A (5.87 g, 94% yield) as a colorless oil.

From Alcohol (−)-15: A solution of alcohol (−)-15 (4.70 g, 10.7 mmol), $PPh_3$ (4.21 g, 16.1 mmol) and imidazole (1.09 g, 16.1 mmol) in benzene/ether (1:2, 75 mL) was treated with $I_2$ (4.08 g, 16.1 mmol) under vigorous stirring. The mixture was stirred 1 h then diluted with ether (200 mL), washed with saturated $Na_2S_2O_3$, brine (100 mL each), dried over $MgSO_4$, filtered and concentrated. Flash chromatography (2% ethyl acetate/hexane) furnished (−)-A (5.56 g, 95% yield) as a colorless oil: $[\alpha]^{23}_D$ −39.3° (c 2.01, $CHCl_3$); IR ($CHCl_3$) 3015 (m), 2960 (s), 2940 (s), 2860 (m), 1620 (w), 1520 (m), 1465 (m), 1430 (w), 1390 (m), 1305 (w), 1255 (s), 1230 (m), 1215 (m), 1205 (m), 1170 (m), 1120 (m), 1070 (m), 1035 (m), 990 (w), 970 (w), 930 (w), 830 (m) $cm^{-1}$; $^1$H NMR (500 MHZ, $CDCl_3$) d 7.39 (d, J=8.7 Hz, 2H), 6.86 (d, J=8.8 Hz, 2H), 5.40 (s, 1H), 4.09 (dd, J=11.2, 4.7 Hz, 1H), 3.85 (dd, J=7.1, 1.9 Hz, 1H), 3.79 (s, 3H), 3.48 (dd, J=8.2, 1.5 Hz, 1H), 3.47 (apparent t, J=11.1 Hz, 1H), 3.18–3.12 (m, 2H), 2.11–2.00 (m, 2H), 1.84 (ddq, J=7.1, 7.1, 1.6 Hz, 1H), 1.02 (d, J=7.1 Hz, 3H), 0.98 (d, J=6.7 Hz, 3H), 0.89 (s, 9H), 0.72 (d, J=6.7 Hz, 3H), 0.06 (s, 3H); $^{13}$C NMR (125 MHZ, $CDCl_3$) d 159.8, 131.4, 127.4, 113.4, 100.9, 82.4, 75.5, 73.2, 55.3, 39.6, 38.7, 30.7, 26.2, 18.4, 14.7, 14.5, 12.2, 10.7, −3.7, −3.8; high resolution mass spectrum (CI, $NH_3$) m/z 548.1833 [(M)$^+$; calcd for $C_{24}H_{41}IO_4Si$: 548.1819].

Anal. Calcd for $C_{24}H_{41}O_4ISi$: C, 52.55; H, 7.53. Found: C, 52.77; H, 7.68.

EXAMPLE 11

Amide (+)-17

A solution of common precursor (+)-5 (12.1 g, 37.2 mmol) and 2,6-lutidine (7.80 mL, 70.0 mmol) in $CH_2Cl_2$ (90 mL) was cooled to 0° C. and tert-Butyldimethylsilyl trifluoromethanesulfonate (12.8 mL, 55.8 mmol) was added over 10 min. After 1.5 h, the mixture was diluted with $Et_2O$ (100 mL), washed with aqueous $NaHSO_4$ (1.0 M), brine (200 mL each), dried over $MgSO_4$, filtered and concentrated. Flash chromatography (10% ethyl acetate/hexanes) provided (+)-17 (16.4 g, 100% yield) as a colorless oil: $[\alpha]^{23}_D$ +9.49° (c 1.47, $CHCl_3$); IR ($CHCl_3$) 3018 (s), 2970 (s), 2945 (s), 2900 (m), 2870 (s), 1658 (s),1620 (m), 1592 (w), 1520 (s), 1470 (s), 1448 (m), 1425 (m), 1393 (m), 1367 (m), 1308 (m), 1255 (s), 1213 (s), 1185 (m), 1178 (m), 1115 (s), 1084 (s), 1042 (s), 1000 (s), 940 (w), 928 (w), 871 (s), 839 (s), 770 (s), 726 (s), 664 (m) $cm^{-1}$; $^1H$ NMR (500 MHZ, $CDCl_3$) d 7.21 (d, J=8.7 Hz, 2H), 6.83 (d, J=8.7 Hz, 2H), 4.36 (ABq, $J_{AB}$=11.6 Hz, $\Delta\delta_{AB}$=17.3 Hz, 2H), 3.92 (dd, J=8.2, 3.0 Hz, 1H), 3.77 (s, 3H), 3.55 (s, 3H), 3.54 (dd, J=9.2, 2.5 Hz, 1H), 3.13 (dd, J=9.2, 7.8 Hz, 1H), 3.09 (s, 3H), 3.15–3.09 (m, 1H), 1.92–1.87 (m, 1H), 1.09 (d, J=7.0 Hz, 3H), 0.98 (d, J=7.0 Hz, 3H), 0.88 (s, 9H), 0.04 (apparent s, 6H); $^{13}C$ NMR (125 MHZ, $CDCl_3$) d 176.8, 159.1, 130.9, 129.2, 113.7, 76.0, 72.7, 71.9, 61.1, 55.2, 39.3, 38.9, 26.1, 18.4, 15.3, 15.0, −3.87, −3.93; high resolution mass spectrum (CI, $NH_3$) m/z 440.2823 [(M+H)$^+$; calcd for $C_{23}H_{42}NO_5Si$: 440.2832].

Anal. Calcd for $C_{23}H_{41}NO_5Si$: C, 62.83; H, 9.40. Found: C, 63.05; H, 9.32.

EXAMPLE 12

Aldehyde (+)-18

A solution of amide (+)-17 (9.19 g, 20.9 mmol) in THF (350 mL) was cooled to −78° C. and DIBAL (1.0 M in hexane, 44.0 mL, 44.0 mmol) was added over 30 min. After 0.5 h at −78° C., the reaction was quenched with MeOH (10 mL). The mixture was diluted with ether (500 mL), washed with saturated aqueous Rochelle's salt, brine (300 mL each), dried over $MgSO_4$, filtered and concentrated. Flash chromatography (10% ethyl acetate/hexane) gave (+)-18 (7.05 g, 89% yield) as a colorless oil: $[\alpha]^{23}_D$ +23.2° (c 1.49, $CHCl_3$); IR ($CHCl_3$) 2960 (s), 2930 (s), 2860 (s), 1730 (s), 1610 (m), 1583 (w), 1510 (m), 1460 (m), 1373 (m), 1360 (w), 1300 (m), 1245 (s), 1170 (m), 1085 (m), 1033 (s), 933 (w), 835 (s) $cm^{-1}$; $^1H$ NMR (500 MHZ, $CDCl_3$) d 9.67 (d, J=0.9 Hz, 1H), 7.22 (d, J=8.7 Hz, 2H), 6.86 (d, J=8.7 Hz, 2H), 4.37 (ABq, $J_{AB}$=11.6 Hz, $\Delta\delta_{AB}$=23.6 Hz, 2H), 4.18 (dd, J=6.1, 3.7 Hz, 1H), 3.78 (s, 3H), 3.41 (dd, J=9.2, 5.7 Hz, 1H), 3.31 (dd, J=9.2, 6.0 Hz, 1H), 2.47 (qdd, J=7.1, 3.7, 0.9 Hz, 1H), 2.03–1.95 (m, 1H), 1.08 (d, J=7.0 Hz, 3H), 0.94 (d, J=7.0 Hz, 3H), 0.84 (s, 9H), 0.04 (s, 3H), −0.03 (s, 3H); $^{13}C$ NMR (125 MHZ, $CDCl_3$) d 204.8, 159.2, 130.5, 129.2, 113.8, 72.7, 72.4, 71.7, 55.3, 50.0, 38.3, 25.9, 18.2, 14.3, 8.4, −4.1, −4.4; high resolution mass spectrum (FAB, NBA) m/z 403.2304 [(M+Na)$^+$; calcd for $C_{21}H_{36}O_4SiNa$: 403.2280].

EXAMPLE 13

Bromo Ester 19

A solution of aldehyde (+)-18 (822.1 mg, 2.16 mmol) in benzene (20 mL) was treated with $Ph_3P=CBrCO_2Et$ (2.28 g, 5.34 mmol), heated at reflux for 40 h and cooled to room temperature. The mixture was filtered through a short silica column (20% ethyl acetate/hexane) and concentrated. Flash chromatography (3% ethyl acetate/hexane) afforded Z-Bromo ester (−)-19 (861.4 mg, 75% yield) and E-Bromo Ester (+)-19 (101.0 mg, 8.8% yield).

Z-Bromo Ester (−)-19: Colorless oil; $[\alpha]^{23}_D$ −6.38° (c 1.85, $CHCl_3$); IR ($CHCl_3$) 2960 (s), 2940 (s), 2860 (s), 1725 (s), 1618 (m), 1590 (w), 1515 (s), 1468 (m), 1390 (m), 1370 (m), 1303 (m), 1250 (s, br), 1176 (m), 1090 (s), 1037 (s), 1008 (m), 950 (m), 940 (m), 840 (s) $cm^{-1}$; $^1H$ NMR (500 MHZ, $C_6D_6$) d 7.45 (d, J=9.7 Hz, 1H), 7.26 (d, J=8.6 Hz, 2H), 6.80 (d, J=8.7 Hz, 2H), 4.37 (ABq, $J_{AB}$=11.6 Hz, $\Delta\delta_{AB}$=19.3 Hz, 2H), 3.99, (dq, J=10.8, 7.1 Hz, 1H), 3.94 (dq, J=10.8, 7.1 Hz, 1H), 3.82 (apparent t, J=5.4 Hz, 1H), 3.41 (dd, J=9.1, 6.3 Hz, 1H), 3.31 (s, 3H), 3.30 (dd, J=9.2, 6.5 Hz, 1H), 3.13–3.06 (m, 1H), 2.05 (apparent septet, J=6.9 Hz, 1H), 1.013 (d, J=7.0 Hz, 3H), 1.006 (d, J=6.8 Hz, 3H), 0.97 (s, 9H), 0.92 (apparent t, J=7.1 Hz, 3H), 0.06 (s, 3H), 0.05 (s, 3H); $^{13}C$ NMR (125 MHZ, $CDCl_3$) d 162.5, 159.1, 149.6, 130.8, 129.0, 114.9, 113.7, 75.5, 72.6, 72.2, 62.4, 55.3, 40.2, 38.9, 26.0, 18.3, 14.2, 14.1, 13.7, −4.0, −4.2; high resolution mass spectrum (CI, $NH_3$) m/z 546.2270 [(M+NH)$^+$; calcd for $C_{25}H_{45}NO_5BrSi$: 546.2251].

Anal. Calcd for $C_{25}H_{41}O_5BrSi$: C, 56.70; H, 7.80. Found: C, 56.96; H, 7.86.

E-Bromo Ester (+)-19. Colorless oil; $[\alpha]^{23}_D$ +3.2° (c 1.65, $CHCl_3$); IR ($CHCl_3$) 2965 (s), 2940 (s), 2905 (m), 2890 (m), 2865 (s), 1720 (s), 1617 (m), 1590 (w), 1518 (s), 1468 (s), 1375 (s), 1350 (m), 1305 (m), 1250 (s, br), 1177 (m), 1090 (s), 1035 (s), 1007 (s), 950 (m), 840 (s), 675 (w) $cm^{-1}$; $^1H$ NMR (500 MHZ, $CDCl_3$) d 7.23 (d, J=8.6 Hz, 2H), 6.86 (d, J=8.7 Hz, 2H), 6.56 (d, J=10.6 Hz, 1H), 4.39 (apparent s, 2H), 4.24 (dq, J=10.8, 7.1 Hz, 1H), 4.22 (dq, J=10.8, 7.1 Hz, 1H), 3.79 (s, 3H), 3.61 (dd, J=5.5, 5.0 Hz, 1H), 3.43 (dd, J=9.2, 5.5 Hz, 1H), 3.39–3.32 (m, 1H), 3.24 (dd, J=9.1, 7.2 Hz, 1H), 1.98–1.90 (m, 1H), 1.30 (apparent t, J=7.1 Hz, 1H), 1.00 (d, J=6.7 Hz, 3H), 0.94 (d, J=7.0 Hz, 3H), 0.89 (s, 9H), 0.05 (s, 3H), 0.03 (s, 3H); $^{13}C$ NMR (125 MHZ, $CDCl_3$) d 162.8, 159.1, 151.9, 130.8, 129.1, 113.7, 110.2, 76.3, 72.6, 72.2, 62.1, 55.2, 38.8, 26.1, 18.3, 14.7, 14.1, 13.9, −4.06, −4.10; high resolution mass spectrum (CI, $NH_3$) m/z 529.1982 [(M+H)$^+$; calcd for $C_{25}H_{42}BrO_5Si$: 529.1985].

Anal. Calcd for $C_{25}H_{41}O_5BrSi$: C, 56.70; H, 7.80. Found: C, 56.83; H, 7.99.

EXAMPLE 14

Allylic Alcohol (−)-20

A solution of ester (−)-19 (858.4 mg, 1.62 mmol) in $CH_2Cl_2$ (16 mL) was cooled to −78° C. and DIBAL (1.0 M in hexane, 3.60 mL, 3.60 mmol) was added over 10 min. After 5 min at −78° C. and 10 min at room temperature, the reaction was quenched with MeOH (200 mL), followed by addition of saturated aqueous Rochelle's salt dropwise with stirring until a solid precipitated. The solution was separated by decanting (3×30 mL rinse, ethyl acetate) and the combined organic solutions were dried over $MgSO_4$, and concentrated. Flash chromatography (10% ethyl acetate/ hexane) provided (−)-20 (674.5 mg, 85% yield) as a colorless oil: $[\alpha]^{23}_D$ −15.5° (c 2.51, $CHCl_3$); IR ($CHCl_3$) 3600 (w), 3420 (w, br), 3010 (m), 2960 (s), 2940 (s), 2890 (m), 2860 (s), 1618 (m), 1590 (w), 1520 (s), 1470 (m), 1380 (m), 1315 (m), 1307 (m), 1255 (s), 1178 (m), 1085 (s), 1039 (s), 1010 (m), 972 (m), 940 (m), 840 (s), 675 (m), 660 (m) $cm^{-1}$; $^1H$ NMR (500 MHZ, $CDCl_3$) d 7.24 (d, J=8.7 Hz, 2H), 6.87 (d, J=8.7 Hz, 2H), 5.88 (br d, J=9.3 Hz, 1H), 4.39 (ABq, $J_{AB}$=11.6 Hz, $\Delta\delta_{AB}$=18.3 Hz, 2H), 4.16 (apparent d, J=5.6 Hz, 2H), 3.79 (s, 3H), 3.59 (apparent t, J=5.3 Hz, 1H), 3.48 (dd, J=9.2, 5.3 Hz, 1H), 3.23 (dd, J=9.2, 7.7 Hz, 1H), 2.82–2.76 (m, 1H), 2.00–1.92 (m, 1H), 0.98 (d, J=6.9 Hz, 3H), 0.97 (d, J=6.8 Hz, 3H), 0.88 (s, 9H), 0.024 (s, 3H), 0.016 (s, 3H); $^{13}C$ NMR (125 MHZ, $CDCl_3$) d 159.1, 134.1, 130.9, 129.1, 125.1, 113.7, 76.5, 72.6, 72.3, 68.4, 55.3, 39.1, 38.7, 26.1, 18.4, 14.9, 14.3, −3.9, −4.0; high resolution mass spectrum (CI, $NH_3$) m/z 487.1873 [(M+H)$^+$; calcd for $C_{23}H_{40}O_4BrSi$: 487.1879].

Anal. Calcd for $C_{23}H_{39}O_4BrSi$: C, 56.66; H, 8.06. Found: C, 56.72; H, 8.07.

EXAMPLE 15

Mesylate (−)-21

A solution of alcohol (−)-20 (6.85 g, 14.1 mmol) in CH$_2$Cl$_2$ (150 mL) was cooled to 0° C. and MsCl (2.20 mL, 28.4 mmol) was added over 2 min. After 10 min, the reaction was quenched with aqueous NaHSO$_4$ (1.0 M, 100 mL). The organic phase was washed with water (100 mL), dried over MgSO$_4$, and concentrated. Flash chromatography (10% ethyl acetate/hexane) afforded (−)-21 (7.85 g, 99% yield) as a colorless oil: [α]$^{23}_D$ −14.6° (c 1.40, CHCl$_3$); IR (CHCl$_3$) 3020 (m), 2960 (s), 2940 (s), 2880 (m), 2860 (s), 1730 (w), 1610 (m), 1583 (m), 1510 (s), 1460 (m), 1410 (m), 1362 (s), 1300 (m), 1250 (s), 1220 (s), 1175 (s), 1080 (s), 1032 (s), 1002 (m), 960 (m), 937 (s), 835 (s) cm$^{−1}$; $^1$H NMR (500 MHZ, CDCl$_3$) d 7.23 (d, J=8.6 Hz, 2H), 6.86 (d, J=8.6 Hz, 2H), 6.07 (d, J=9.4 Hz, 1H), 4.74 (d, J=0.4 Hz, 2H), 4.38 (ABq, J$_{AB}$=11.7 Hz, Δδ$_{AB}$=25.5 Hz, 2H), 3.79 (s, 3H), 3.61 (apparent t, J=5.2 Hz, 1H), 3.44 (dd, J=9.2, 5.7 Hz, 1H), 3.22 (dd, J=9.2, 7.3 Hz, 1H), 3.01 (s, 3H), 2.84–2.77 (m, 1H), 1.99–1.91 (m, 1H), 0.98 (d, J=6.8 Hz, 3H), 0.96 (d, J=7.0 Hz, 3H), 0.88 (s, 9H), 0.03 (s, 3H), 0.02 (s, 3H); $^{13}$C NMR (125 MHZ, CDCl) d 159.1, 140.9, 130.8, 129.1, 116.7, 113.8, 76.1, 74.2, 72.6, 72.1, 55.3, 39.6, 38.8, 38.5, 26.0, 18.3, 14.7, 14.3, −3.9, −4.0; high resolution mass spectrum (CI, NH$_3$) m/z 582.1911 [(M+NH)$^+$; calcd for C$_{24}$H$_{45}$NO$_6$BrSSi: 582.1920].

EXAMPLE 16

Vinyl Bromide (−)-22

A solution of mesylate (−)-21 (6.43 g, 11.4 mmol) in benzene (120 mL) was treated with LiBHEt$_3$ (1.0 M in THF, 25.0 mL, 25.0 mmol) at room temperature. After 0.5 h, the reaction was quenched with aqueous NaOH (1.0 N, 50 mL). The mixture was diluted with ethyl acetate (200 mL), washed with brine (2×200 mL), dried over MgSO$_4$, filtered and concentrated. Flash chromatography (5% ethyl acetate/hexane) provided (−)-22 (4.86 g, 91%) as a colorless oil: [α]$^{23}_D$ −16.9° (c 1.69, CHCl$_3$); IR (CHCl$_3$) 3005 (m), 2965 (s), 2935 (s), 2860 (s), 1660 (w), 1610 (m), 1585 (w), 1510 (m), 1460 (m), 1425 (w), 1377 (m), 1360 (m), 1300 (m), 1250 (s), 1180 (m), 1170 (m), 1075 (s), 1030 (s), 860 (m), 835 (s), 805 (m), 660 (w) cm$^{−1}$; $^1$H NMR (500 MHZ, CDCl$_3$) d 7.24 (d, J=8.6 Hz, 2H), 6.86 (d, J=8.6 Hz, 2H), 5.47 (apparent dd, J=9.0, 1.2 Hz, 1H), 4.39 (ABq, J$_{AB}$=11.7 Hz, Δδ$_{AB}$=15.8 Hz, 2H), 3.79 (s, 3H), 3.56 (apparent t, J=5.4 Hz, 1H), 3.50 (dd, J=9.1, 5.1 Hz, 1H), 3.22 (dd, J=8.8, 8.1 Hz, 1H), 2.74–2.67 (m, 1H), 2.21 (d, J=1.1 Hz, 3H), 1.99–1.91 (m, 1H), 0.98 (d, J=6.9 Hz, 3H), 0.94 (d, J=6.8 Hz, 3H), 0.88 (s, 9H), 0.01 (s, 3H), 0.00 (s, 3H); $^{13}$C NMR (125 MHZ, CDCl$_3$) d 159.1, 133.4, 131.0, 129.1, 120.6, 113.7, 76.7, 72.6, 72.5, 55.3, 39.7, 38.7, 28.8, 26.1, 18.4, 14.8, 14.4, −3.96, −4.01; high resolution mass spectrum (FAB, NBA) m/z 493.1763 [(M+Na)$^+$; calcd for C$_{23}$H$_{39}$O$_3$BrSiNa: 493.1750].

EXAMPLE 17

Vinyl Silane (−)-23

A solution of vinyl bromide (−)-22 (83.2 mg, 0.177 mmol) in THF (2.0 mL) was cooled to −78° C. and n-BuLi (1.6 M in hexane, 260 ml, 416 mmol) was added over 10 min. After 1 h at −78° C. and 15 min at room temperature, the reaction was quenched with H$_2$O (200 mL). The mixture was concentrated and dissolved in ethyl acetate (30 mL), washed with water (30 mL), dried over MgSO$_4$, filtered and concentrated. Flash chromatography (5% ethyl acetate/hexane) provided (−)-23 (47.9 mg, 69% yield) as a colorless oil: [α]$^{23}_D$ −61.5° (c 0.615, CHCl$_3$); IR (CHCl$_3$) 3680 (w), 3470 (m, br), 1614 (m), 1588 (w), 1513 (s), 1465 (m), 1442 (m), 1415 (m), 1360 (m), 1302 (m), 1250 (s), 1176 (m), 1120 (m), 1077 (m), 1032 (m), 992 (m), 830 (s), 820 (s), 805 (s) cm$^{−1}$; $^1$H NMR (500 MHZ, CDCl$_3$) d 7.22 (d, J=8.7 Hz, 2H), 6.85 (d, J=8.7 Hz, 2H), 6.22 (dq, J=10.5, 1.6 Hz, 1H), 4.42 (ABq, J$_{AB}$=11.4 Hz, Δδ$_{AB}$=18.8 Hz, 2H), 3.78 (s, 3H), 3.65 (br s, 1H), 3.56 (dd, J=9.1, 4.0 Hz, 1H), 3.44 (dd, J=8.8, 2.9 Hz, 1H), 3.42 (apparent t, J=8.8 Hz, 1H), 2.45 (dqd, J=10.3, 6.6, 2.7 Hz, 1H), 1.95–1.87 (m, 1H), 1.78 (d, J=1.6 Hz, 3H), 0.91 (d, J=6.7 Hz, 3H), 0.87 (s, 9H), 0.80 (d, J=7.0 Hz, 3H), 0.09 (s, 3H), 0.08 (s, 3H); $^{13}$C NMR (125 MHZ, CDCl$_3$) d 159.4, 147.7, 130.8, 129.7, 129.4, 113.9, 79.9, 76.4, 73.3, 55.3, 38.1, 36.3, 27.1, 26.6 17.8, 13.4, 13.1, −3.4, −3.7; high resolution mass spectrum (CI, NH$_3$) m/z 393.2821 [(M+H)$^+$; calcd for C$_{23}$H$_{41}$O$_3$Si: 393.2824].

Anal. Calcd for C$_{23}$H$_{40}$O$_3$Si: C, 70.36; H, 10.27. Found: C, 70.58; H, 10.57.

EXAMPLE 18 trans Olefin (+)-24

A solution of vinyl bromide (−)-22 (27.8 mg, 0.0591 mmol) in ether (600 μL) was cooled to −78° C., and t-BuLi (1.7 M in pentane, 103 μL, 0.175 mmol) was added over 2 min. After 10 min at −78° C. and 5 min at room temperature, the reaction was quenched with MeOH (100 mL). The mixture was filtered through a short silica plug, and concentrated. Flash chromatography (1% ethyl acetate/hexane) provided (+)-24 (21.9 mg, 94% yield) as a colorless oil; [α]$^{23}_D$ +19.3° (c 1.10, CHCl$_3$); IR (CHCl$_3$) 3000 (m), 2960 (s), 2935 (s), 2880 (m), 2860 (s), 1612 (m), 1587 (w), 1510 (s), 1462 (m), 1440 (m), 1405 (w), 1375 (m), 1360 (m), 1300 (m), 1250 (s), 1170 (m), 1090 (s), 1034 (s), 1002 (m), 970 (m), 934 (w), 850 (m), 832 (s), 720 (m) cm$^{−1}$; $^1$H NMR (500 MHZ, C$_6$D$_6$) d 7.24 (d, J=8.7 Hz, 2H), 6.80 (d, J=8.6 Hz, 2H), 5.43 (ddq, J=15.3, 7.8, 1.4 Hz, 1H), 5.34 (dqd, J=15.4, 6.3, 0.7 Hz, 1H), 4.38 (ABq, J$_{AB}$=11.7 Hz, Δδ$_{AB}$=30.7 Hz, 2H), 3.58 (apparent t, J=5.2 Hz, 1H), 3.57 (dd, J=9.0, 5.1 Hz, 1H), 3.36 (dd, J=9.0, 7.2 Hz, 1H), 3.30 (s, 3H), 2.39 (ddq, J=6.8, 6.8, 6.8 Hz, 1H), 2.17–2.10 (m, 1H), 1.58 (apparent d, J=6.1 Hz, 3H), 1.07 (d, J=7.2 Hz, 3H), 1.05 (d, J=6.9 Hz, 3H), 1.00 (s, 9H), 0.10 (s, 3H), 0.08 (s, 3H); $^{13}$C NMR (125 MHZ, CDCl$_3$) d 159.0, 135.6, 131.1, 129.1, 123.9, 113.7, 78.4, 72.6, 72.5, 55.3, 40.4, 37.9, 26.2, 26.1, 18.4, 18.0, 15.9; 15.1, −3.8, −4.1; high resolution mass spectrum (CI, NH$_3$) m/z 393.2836 [(M+H)$^+$; calcd for C$_{23}$H$_{41}$O$_3$Si: 393.2824].

EXAMPLE 19

Alcohol (−)-25

A solution of PMB ether (−)-22 (50.0 mg, 0.106 mmol) and PMB acetal (−)-15 (46.5 mg, 0.106 mmol) in CH$_2$Cl$_2$ (2.0 mL) was cooled to 0° C., then treated with H$_2$O (100 mL) and DDQ (26.5 mg, 0.117 mmol). After 30 min, the mixture was diluted with ether (60 mL), washed with saturated aqueous NaHCO$_3$ (60 mL), brine (3×60 mL), dried over MgSO$_4$, filtered and concentrated. Flash chromatography (gradient elution, 5%→10% ethyl acetate/hexane) afforded (−)-25 (31.0 mg, 83% yield) and recovered (−)-15 (40.0 mg, 86% recovery).

(−)-25: [α]$^{23}_D$ −13.3° (c 0.99, CHCl$_3$); IR (CHCl$_3$) 3640 (w), 3520 (m), 3000 (m), 2960 (s), 2940 (s), 2890 (m), 2860 (s), 1660 (w), 1472 (m), 1465 (m), 1440 (m), 1407 (m), 1390 (m), 1380 (m), 1360 (m), 1258 (s), 1072 (s), 1023 (s), 1005 (s), 980 (m), 937 (m), 847 (s) cm$^{−1}$; $^1$H NMR (500 MHZ, CDCl$_3$) d 5.50 (apparent dd, J=9.0, 1.1 Hz, 1H), 3.65 (dd, J=11.0, 4.8 Hz, 1H), 3.59 (dd, J=11.0, 5.7 Hz, 1H), 3.56 (apparent t, J=5.2 Hz, 1H), 2.80–2.72 (m, 1H), 2.25 (d, J=1.0 Hz, 3H), 2.20 (br s, 1H), 1.86–1.78 (m, 1H), 0.99 (d, J=7.1 Hz, 3H), 0.98 (d, J=6.9 Hz, 3H), 0.90 (s, 9H), 0.09 (s, 3H), 0.05 (s, 3H); $^{13}$C NMR (125 MHZ, CDCl$_3$) d 132.6, 121.7, 79.7, 65.6, 40.9, 38.8, 28.9, 26.1, 18.3, 15.5, 15.0, −3.9, −4.0; high resolution mass spectrum (CI, NH$_3$) m/z 351.1087 [M$^+$; calcd for C$_{15}$H$_{31}$O$_2$BrSi: 351.1093].

EXAMPLE 20

Alcohol (+)-26

A solution of amide (+)-17 (323.5 mg, 0.738 mmol) in EtOH (8.0 mL) was stirred for 5 h under H$_2$ atmosphere in the presence of Pearlman's catalyst (20% Pd(OH)$_2$/C, 104.1 mg), then filtered and concentrated. Flash chromatography (10 mL silica, 20% ethyl acetate/hexane) provided (+)-26 (216.7 mg, 92% yield) as a colorless oil: [α]$^{23}_D$ +16.1° (c 2.60, CHCl$_3$); IR (CHCl$_3$) 3480 (m, br), 3000 (s), 2958 (s), 2935 (s), 2880 (s), 2860 (s) 1635 (s), 1460 (s), 1415 (m), 1390 (s), 1360 (m), 1285 (w) 1255 (s), 1174 (m), 1148 (m), 1093 (s), 1070 (s), 1047 (s), 1033 (s), 990 (s), 935 (m), 905 (w), 860 (s), 830 (s) cm$^{-1}$; $^1$H NMR (500 MHZ, CDCl$_3$) d 4.05 (dd, J=9.1, 3.1 Hz, 1H), 3.69 (s, 3H), 3.55–3.50 (m, 1H), 3.23 (ddd, J=10.1, 10.1, 2.8 Hz, 1H), 3.13 (s, 3H), 3.09 (br m, 1H), 2.81 (br m, 1H), 1.91–1.83 (m, 1H), 1.14 (d, J=7.0 Hz, 3H), 0.879 (d, J=7.0 Hz, 3H), 0.879 (s, 9H), 0.08 (s, 3H), 0.06 (s, 3H); $^{13}$C NMR (125 MHZ, CDCl$_3$) d 177.3, 75.2, 64.9, 61.5, 40.8, 38.2, 32.2, 26.0, 18.2, 15.9, 12.8, −4.1, −4.3; high resolution mass spectrum (CI, NH$_3$) m/z 320.2265 [(M+H)$^+$; calcd for C$_{15}$H$_{34}$NO$_4$Si: 320.2256].

EXAMPLE 21

Aldehyde (+)-27

A solution of alcohol (+)-26 (8.80 g, 27.5 mmol) and NEt$_3$ (15.3 mL, 110 mmol) in CH$_2$Cl$_2$ (50 mL) was cooled to −10° C. and treated with SO$_3$·pyr (13.1 g, 82.6 mmol) in DMSO (100 mL). After 20 min at room temperature, the mixture was diluted with ether (300 mL), washed with aqueous NaHSO$_4$ (1.0 M, 200 mL), brine (4×200 mL), dried over MgSO$_4$, filtered and concentrated. Flash chromatography (20% ethyl acetate/hexane) afforded (+)-27 (8.55 g, 98% yield) as a colorless oil: [α]$^{23}_D$ +51.2° (c 1.00, CHCl$_3$); IR (CHCl$_3$) 3010 (m), 2960 (s), 2940 (s), 2895 (m), 2865 (m), 1750 (m), 1720 (s), 1647 (s), 1460 (m), 1420 (m), 1390 (s), 1360 (m), 1255 (m), 1180 (m), 1105 (m), 1077 (m), 1040 (s), 995 (s), 936 (m), 853 (s), 837 (s), 710 (m), 657 (m) cm$^{-1}$; $^1$H NMR (500 MHZ, CDCl$_3$) d 9.68 (d, J=1.6 Hz, 1H), 4.22 (dd, J=8.9, 2.6 Hz, 1H), 3.68 (s, 3H), 3.10 (apparent s, 4H), 2.46 (qdd, J=7.1, 2.6, 1.5 Hz, 1H), 1.16 (d, J=6.9 Hz, 3H), 1.10 (d, J=7.0 Hz, 3H), 0.88 (s, 9H), 0.092 (s, 3H), 0.088 (s, 3H); $^{13}$C NMR (125 MHZ, CDCl$_3$) d 203.2, 175.6, 75.1, 61.5, 52.1, 39.6, 32.1, 25.9, 18.2, 15.4, 10.2, −4.07, −4.11; high resolution mass spectrum (CI,NH$_3$) m/z 318.2096 [(M+H)$^+$; C$_{15}$H$_{32}$NO$_4$Si: 318.2100].

EXAMPLE 22

Dithiane (+)-28

A solution of ZnCl$_2$ (dried at 140° C. for 1 h under vacuum, 170.5 mg, 1.25 mmol) in ether (6.0 mL) was cooled to 0° C. and (TMSSCH$_2$)$_2$CH$_2$ (175.0 μL, 0.628 mmol) was added. The resultant white milky suspension was treated with aldehyde (+)-27 (180.0 mg, 0.567 mmol) in ether (6.0 mL). The mixture was stirred for 4.5 h at 0° C. and 1.5 h at room temperature, then partitioned between ethyl acetate (50 mL) and aqueous ammonia (30 mL). The organic phase was washed with brine (2×30 mL), dried over MgSO$_4$, filtered and concentrated. Flash chromatography (10% ethyl acetate/hexane) provided (+)-28 (182.9 mg, 79% yield) as a white solid: mp 55–57° C.; [α]$^{23}_D$ +18.5° (c 1.44, CHCl$_3$); IR (CHCl$_3$) 3015 (m), 2970 (s), 2945 (s), 2910 (m), 2870 (m), 1665 (s), 1475 (m), 1470 (m), 1437 (m), 1430 (m), 1420 (m), 1390 (m), 1365 (m), 1320 (w), 1280 (m), 1260 (m), 1120 (m), 1115 (m), 1097 (m), 1080 (m), 1065 (m), 1040 (m), 1000 (m), 940 (w), 925 (w), 910 (w), 877 (m), 838 (s), 815 (m), 800 (m), 700 (w), 675 (w), 660 (w) cm$^{-1}$; $^1$H NMR (500 MHZ, CDCl$_3$) d 4.33 (d, J=4.2 Hz, 1H), 4.23 (dd, J=7.1, 3.6 Hz, 1H), 3.68 (s, 3H), 3.15 (s, 3H), 2.98 (dq, J=6.8, 3.7 Hz, 1H), 2.90 (ddd, J=14.1, 12.2, 2.5 Hz, 1H), 2.83–2.77 (m, 3H), 2.09–2.03 (m, 1H), 1.94 (ddq, J=7.2, 7.2, 4.3 Hz, 1H), 1.88–1.76 (m, 1H), 1.08 (d, J=7.2 Hz, 3H), 1.07 (d, J=6.9 Hz, 3H), 0.90 (s, 9H), 0.13 (s, 3H), 0.02 (s, 3H); $^{13}$C NMR (125 MHZ, CDCl$_3$) d 176.2, 73.2, 61.0, 50.8, 44.2, 38.6, 31.3, 30.3, 26.2, 18.4, 12.9, 11.0, −4.1, −4.2; high resolution mass spectrum (CI, NH$_3$) m/z 408.2081 [(M+H)$^+$; calcd for C$_{18}$H$_{38}$NO$_3$S$_2$Si: 408.2062].

Anal. Calcd. for C$_{18}$H$_{37}$NO$_3$S$_2$Si: C, 53.03; H, 9.15. Found: C, 53.06; H, 9.31.

EXAMPLE 23

Aldehyde (+)-29

A solution of dithiane (+)-28 (1.05 g, 2.58 mmol) in THF (40 mL) was cooled to −78° C. and DIBAL (1.0 M in hexane, 5.15 mL, 5.15 mmol) was added over 15 min. After 10 min at −78° C., the mixture was quenched with MeOH (2.0 mL) and partitioned between ether and saturated aqueous Rochelle's salt (50 mL each). The organic phase was washed with brine (30 mL), dried over MgSO$_4$, filtered and concentrated. Flash chromatography (10% ethyl acetate/hexane) provided (+)-29 (822 mg, 91% yield) as white solid: mp 54–55° C.; [α]$^{23}_D$ +50.8° (c 1.19, CHCl$_3$); IR (CHCl$_3$) 2965 (s), 2940 (s), 2910 (s), 2865 (s), 2720 (w), 1730 (s), 1475 (m), 1467 (m), 1428 (m), 1418 (m), 1390 (m), 1365 (m), 1280 (m), 1260 (s), 1190 (m), 1150 (m), 1104 (s), 1070 (m), 1030 (s), 1007 (m), 953 (m), 940 (m), 910 (m), 835 (s), 810 (m), 675 (m) cm$^{-1}$; $^1$H NMR (500 MHZ, CDCl$_3$) d 9.70 (s, 1H), 4.44 (dd, J=8.3, 2.2 Hz, 1H), 4.38 (d, J=3.7 Hz, 1H), 2.93 (ddd, J=14.1, 12.3, 2.6 Hz, 1H), 2.84–2.80 (m, 3H), 2.43 (qd, J=7.1, 2.2 Hz, 1H), 2.13–2.07 (m, 1H), 2.02 (dqd, J=8.2, 7.1, 3.7 Hz, 1H), 1.88–1.79 (m, 1H), 1.10 (d, J=6.9 Hz, 3H), 1.05 (d, J=7.1 Hz, 3H), 0.87 (s, 9H), 0.16 (s, 3H), −0.01 (s, 3H); $^{13}$C NMR (125 MHZ, CDCl$_3$) d 204.6, 71.1, 51.0, 49.7, 43.5, 31.3, 30.3, 26.2, 26.0, 18.4, 12.9, 6.8, −3.9, −4.3; high resolution mass spectrum (CI, NH$_3$) m/z 349.1678 [(M+H)$^+$; calcd for C$_{16}$H$_{33}$O$_2$S$_2$Si: 349.1691].

Anal. Calcd for C$_{16}$H$_{32}$O$_2$S$_2$Si: C, 55.12; H, 9.25. Found: C, 55.08; H, 9.28.

EXAMPLE 24

Dimethoxy Acetal (+)-30

A solution of aldehyde (+)-29 (792 mg, 2.27 mmol) in HC(OMe)$_3$/MeOH (48 mL, 1:5) was treated with TsOH.H$_2$O (8.6 mg, 0.045 mmol) at room temperature. After 30 min, NEt$_3$ (1.0 mL) was added and the mixture was concentrated. Flash chromatography (10% ethyl acetate/hexane) provided (+)-30 (886 mg, 99% yield) as a white solid: mp 58–59° C.; [α]$^{23}_D$ +27.1° (c 2.85, CHCl$_3$); IR (CHCl$_3$) 2960 (s), 2940 (s), 2905 (s), 2860 (m), 2835 (m), 1473 (m), 1463 (m), 1432 (m), 1425 (m), 1415 (m), 1387 (m), 1362 (m), 1340 (w), 1278 (m), 1252 (s), 1190 (m), 1158 (m), 1104 (s), 1070 (m), 1050 (m), 1030 (s), 1005 (m), 963 (m), 938 (m), 908 (m), 873 (m), 834 (s), 810 (m) cm$^{-1}$; $^1$H NMR (500 MHZ, CDCl$_3$) d 4.41 (d, J=3.1 Hz, 1H), 4.23 (d, J=8.6 Hz, 1H), 4.02 (dd, J=8.6, 1.3 Hz, 1H), 3.29 (s, 3H), 3.26 (s, 3H), 2.93 (ddd, J=14.0, 12.4, 2.5 Hz, 1H), 2.85–2.78 (m, 3H), 2.11–2.05 (m, 1H), 1.93–1.77 (m, 3H), 1.00 (d, J=7.2 Hz, 3H), 0.91 (s, 9H), 0.85 (d, J=6.9 Hz, 3H), 0.17 (s, 3H), 0.09 (s, 3H); $^{13}$C NMR (125 MHZ, CDCl$_3$) d 105.0, 71.5, 53.0, 51.5, 51.2, 43.8, 37.4, 31.3, 30.2, 26.3, 18.8, 12.9, 8.1, −3.8, −4.3; high resolution mass spectrum (FAB, NBA) m/z 417.1934 [(M+Na)$^+$; calcd for C$_{18}$H$_{38}$O$_3$S$_2$SiNa: 417.1930].

Anal. Calcd for C$_{18}$H$_{38}$O$_3$S$_2$Si: C, 54.78; H, 9.70. Found: C, 54.80; H, 9.66.

EXAMPLE 25

Hydroxy Acetal (−)-32

A solution of dithiane (+)-30 (3.60 g, 9.12 mmol) in 10% HMPA/THF (60 mL) was cooled to −78° C. and treated with t-BuLi (1.7 M in pentane, 5.63 mL, 9.58 mmol) dropwise over 15 min. The mixture was stirred 1 h at −78° C. and 1 h at −42° C., then recooled to −78° C. A solution of benzyl R-(−)-glycidyl ether (1.65 g, 10.0 mmol) in 10% HMPA/THF (12 mL) was added via cannula. After 0.5 h, the reaction mixture was warmed to −42° C. for 0.5 h and quenched with saturated aqueous $NH_4Cl$ (20 mL). The mixture was diluted with ether (200 mL), washed with water, brine (200 mL each), dried over $MgSO_4$, filtered and concentrated. Flash chromatography (10% ethyl acetate/hexane) afforded (−)-32 (4.04 g, 79% yield) as a colorless oil: $[\alpha]^{23}_D$ −5.9° (c 2.1, $CHCl_3$); IR ($CHCl_3$) 3450 (w, br), 3020 (m), 2960 (s), 2940 (s), 2910 (m), 2860 (m), 2840 (m), 1605 (w), 1500 (w), 1475 (m), 1468 (m), 1458 (m), 1440 (m), 1430 (m), 1393 (m), 1387 (m), 1365 (m), 1280 (w), 1255 (m), 1233 (m), 1203 (m), 1167 (w), 1153 (w), 1110 (s), 1060 (m), 1045 (m), 1030 (m), 1010 (m), 980 (w), 940 (m), 910 (w), 860 (m), 837 (s), 800 (m), 695 (m), 670 (m), 660 (m) $cm^{-1}$; $^1H$ NMR (500 MHZ, $CDCl_3$) d 7.35–7.25 (m, 5H), 4.64 (dd, J=4.0, 1.1 Hz, 1H), 4.57 (ABq, $J_{AB}$=12.1 Hz, $\Delta\delta_{AB}$=17.8 Hz, 2H), 4.21 (d, J=7.7 Hz, 1H), 4.14–4.09 (m, 1H), 3.48 (dd, J=9.5, 6.0 Hz, 1H), 3.47 (dd, J=9.6, 5.0 Hz, 1H), 3.37 (d, J=0.7 Hz, 1H), 3.36 (s, 3H), 3.29 (s, 3H), 3.08 (ddd, J=14.4, 11.4, 2.9 Hz, 1H), 2.95 (ddd, J=14.4, 11.3, 3.1 Hz, 1H), 2.71–2.64 (m, 2H), 2.59 (dqd, J=6.7, 6.7, 0.9 Hz, 1H), 2.49 (dd, J=15.6, 7.9 Hz, 1H), 2.30 (dq, J=4.0, 7.3 Hz, 1H), 2.27 (dd, J=15.6, 2.3 Hz, 1H), 2.04–2.00 (m, 1H), 1.86–1.78 (m, 1H), 1.18 (d, J=7.4 Hz, 3H), 0.94 (d, J=6.8 Hz, 3H), 0.90 (s, 9H), 0.08 (s, 3H), 0.07 (s, 3H); $^{13}C$ NMR (125 MHZ, $CDCl_3$) d 138.2, 128.4, 127.6, 106.9, 74.4, 73.3, 70.0, 67.9, 55.7, 53.6, 52.6, 47.2, 39.4, 38.5, 26.3, 26.1, 26.0, 25.0, 18.3, 9.8, 9.5, −3.9, −4.9; high resolution mass spectrum (FAB, NBA) m/z 581.2763 [(M+Na)$^+$; calcd for $C_{28}H_{50}O_5S_2SiNa$: 581.2767].

EXAMPLE 26

Ketone (+)-33

A solution of hydroxy acetal (−)-32 (3.94 g, 7.05 mmol) in $H_2O$/MeOH (1:9, 75 mL) was treated with $(CF_3CO_2)_2$ IPh (4.55 g, 10.6 mmol) at 0° C. After 5 min, the mixture was quenched with saturated $NaHCO_3$ (20 mL) and extracted with ether (200 mL). The organic phase was washed with brine (200 mL), dried over $MgSO_4$, filtered and concentrated. Flash chromatography (20% ethyl acetate/hexane) furnished (+)-33 (2.66 g, 80% yield) as a colorless oil. $[\alpha]^{23}_D$ +36° (c 0.36, $CHCl_3$); IR ($CHCl_3$) 3580 (w, br), 3005 (m), 2960 (s), 2930 (s), 2900 (m), 2860 (m), 1710 (m), 1463 (m), 1455 (m), 1387 (m), 1362 (m), 1253 (m), 1220 (m), 1105 (s), 1070 (s),1053 (s), 1030 (s), 1002 (m), 938 (m), 866 (m), 830 (s), 808 (m), 690 (m), 660 (m) $cm^{-1}$; $^1H$ NMR (500 MHZ, $CDCl_3$) d 7.34–7.25 (m, 5H), 4.54 (apparent s, 2H), 4.40–4.25 (m, 1H), 4.23 (dd, J=7.6, 1.9 Hz, 1H), 4.19 (d, J=8.0 Hz, 1H), 3.46 (dd, J=9.7, 4.9 Hz, 1H), 3.43 (dd, J=9.7, 5.9 Hz, 1H), 3.27 (s, 3H), 3.25 (s, 3H), 3.01 (d, J=3.8 Hz, 1H), 2.76 (dd, J=18.0, 8.7 Hz, 1H), 2.74 (dq, J=7.1, 7.1 Hz, 1H), 2.62 (dd, J=17.9, 3.2 Hz, 1H), 1.83 (dqd, J=8.0, 7.0, 1.9 Hz, 1H), 0.97 (d, J=7.1 Hz, 3H), 0.88 (d, J=6.9 Hz, 3H), 0.83 (s, 9H), 0.06 (s, 3H), −0.05 (s, 3H); $^{13}C$ NMR (125 MHZ, $CDCl_3$) d 213.0, 138.0, 128.4, 127.71, 127.68, 105.0, 73.4, 73.3, 71.8, 66.5, 52.9, 52.6, 52.3, 46.5, 37.9, 26.1, 18.4, 12.7, 8.8, −4.1, −4.8; high resolution mass spectrum (FAB, NBA) m/z 491.2821 [(M+Na)$^+$; calcd for $C_{25}H_{44}O_6SiNa$: 491.2805].

EXAMPLE 27

Diol (−)-34

A solution of $Me_4NBH(OAc)_3$ (1.80 g, 6.84 mmol) in HOAc/$CH_3CN$ (1:1, 10.0 mL) was cooled to −40° C. and ketone (+)-33 (536 mg, 1.14 mmol) in $CH_3CN$ (5 mL) was added. After 12 h at −20° C., the mixture was treated with saturated aqueous Rochelle's salt (20 mL) and extracted with $CH_2Cl_2$ (3×50 mL). The combined organic extracts were washed with saturated $NaHCO_3$, brine (100 mL each), dried over $MgSO_4$, filtered and concentrated. Flash chromatography (1:1:1, $CH_2Cl_2$/ether/hexane) provided (−)-34 (519 mg, 97% yield) as a colorless oil: $[\alpha]^{23}_D$ −7.78° (c 0.900, $CHCl_3$); IR ($CHCl_3$) 3680 (w), 3460 (m, br), 3015 (m), 2960 (s), 2940 (s), 2900 (m), 2865 (s), 1470 (m), 1460 (m), 1390 (m), 1365 (m), 1260 (m), 1230 (m), 1208 (m), 1112 (s), 1065 (s), 1030 (m), 1010 (m), 942 (m), 865 (m), 838 (m), 698 (m) $cm^{-1}$; $^1H$ NMR (500 MHZ, $CDCl_3$) d 7.33–7.30 (m, 4H), 7.29–7.25 (m, 1H), 4.55 (ABq, $J_{AB}$=12.0 Hz, $\Delta\delta_{AB}$=15.7 Hz, 2 H), 4.16–4.11 (m, 1H), 4.13 (d, J=7.8 Hz, 1H), 4.07 (dd, J=4.8, 1.6 Hz, 1H), 3.73 (br s, 1H), 3.68 (dddd, J=9.3, 9.3, 2.4, 2.4 Hz, 1H), 3.50 (dd, J=9.6, 4.5 Hz, 1H), 3.42 (dd, J=9.4, 7.0 Hz, 1H), 3.38 (s, 3H), 3.29 (s, 3H), 3.09 (d, J=4.0 Hz, 1H), 1.90 (dqd, J=7.0, 7.0, 1.5 Hz, 1H), 1.76 (br dd, J=13.6, 8.5 Hz, 1H), 1.68 (dqd, J=9.6, 6.9, 5.0 Hz, 1H), 1.49 (ddd, J=14.3, 9.0, 2.9 Hz, 1H), 0.894 (d, J=7.9 Hz, 3H), 0.886 (s, 9H), 0.80 (d, J=7.0 Hz, 3H), 0.055 (s, 3H), 0.048 (s, 3H); $^{13}C$ NMR (125 MHZ, $CDCl_3$) d 138.2, 128.4, 127.7, 127.6, 107.3, 74.5, 73.3, 71.0, 70.9, 67.8, 55.2, 52.1, 45.9, 37.3, 36.9, 25.9, 18.2, 11.6, 10.6, −4.3, −4.7; high resolution mass spectrum (FAB, NBA) m/z 493.2951 [(M+Na)$^+$; calcd for $C_{25}H_{46}O_6SiNa$: 493.2962].

EXAMPLE 28

Alcohol (−)-35

A solution of (−)-34 (123.3 mg, 0.262 mmol) in benzene (10 mL) was treated with TsOH.$H_2O$ (2.0 mg, 0.0105 mmol) at room temperature. After 20 min, the mixture was quenched with $NEt_3$ (1.0 mL) and concentrated. Flash chromatography (2% ether/$CH_2Cl_2$) afforded 35 (100.1 mg, β/α=2:1, 87% yield) as a colorless oil.

β Anomer (35): $[\alpha]^{23}_D$ −3.3° (c 2.25, $CHCl_3$); IR ($CHCl_3$) 3680 (w), 3580 (w), 3490 (w), 3010 (m), 2960 (s), 2930 (s), 2880 (m), 2860 (s), 1603 (w), 1525 (w), 1515 (w), 1493 (m), 1470 (m), 1460 (m), 1450 (m), 1387 (m), 1360 (m), 1347 (m), 1330 (m), 1253 (s), 1225 (m), 1200 (m), 1143 (m), 1110 (s), 1070 (s), 1045 (s), 1020 (s), 1015 (m), 1003 (m), 985 (m), 950 (m), 870 (m), 853 (m), 833 (s), 807 (m), 800 (m), 790 (m), 690 (m), 670 (m), 657 (m) $cm^{-1}$; $^1H$ NMR (500 MHZ, $CDCl_3$) d 7.34–7.25 (m, 5H), 4.69 (d, J=2.4 Hz, 1H), 4.55 (ABq, $J_{AB}$=12.0 Hz, $\Delta\delta_{AB}$=14.6 Hz, 2H), 4.17–4.12 (m, 1H), 3.78 (ddd, J=9.7, 9.7, 2.5 Hz, 1H), 3.60 (apparent t, J=2.7 Hz, 1H), 3.51 (dd, J=9.5, 4.1 Hz, 1H), 3.42 (s, 3H), 3.39 (dd, J=9.5, 7.0 Hz, 1H), 2.86 (d, J=3.8 Hz, 1H), 1.88 (apparent qt, J=7.1, 2.7 Hz, 1H), 1.76 (ddd, J=14.4, 8.9, 2.6 Hz, 1H), 1.72–1.65 (m, 1H), 1.53 (ddd, J=14.4, 9.3, 2.9 Hz, 1H), 0.90 (d, J=8.2 Hz, 3H), 0.89 (s, 9H), 0.78 (d, J=6.8 Hz, 3H), 0.04 (s, 3H), 0.02 (s, 3H); $^{13}C$ NMR (125 MHZ, $CDCl_3$) d 138.2, 128.4, 127.7, 101.2, 76.7, 74.7, 73.3, 73.0, 67.4, 56.6, 41.1, 36.0, 34.7, 25.9, 18.1, 13.7, 9.7, −4.6, −4.9; high resolution mass spectrum (FAB, NBA) m/z 461.2693 [(M+Na)$^+$; calcd for $C_{24}H_{42}O_5SiNa$: 461.2699].

α Anomer (35): $[\alpha]^{23}_D$ +48° (c 0.54, $CHCl_3$); IR ($CHCl_3$) 3670 (w), 3570 (w), 3480 (w, br), 3005 (m), 2960 (s), 2930 (s), 2880 (m), 2855 (s), 1600 (w), 1527 (w), 1515 (w), 1495 (w), 1460 (m), 1360 (m), 1253 (s), 1225 (m), 1212 (m), 1200 (m), 1170 (m), 1148 (m), 1106 (s), 1087 (s), 1048 (s), 1030 (s), 963 (m), 872 (m), 833 (s), 788 (m), 690 (m) $cm^{-1}$; $^1H$ NMR (500 MHZ, $CDCl_3$) d 7.34–7.24 (m, 5H), 4.55 (ABq, $J_{AB}$=12.1 Hz, $\Delta\delta_{AB}$=14.4 Hz, 2H), 4.30 (d, J=2.9 Hz, 1H), 4.12–4.07 (m, 1H), 4.01 (ddd, J=9.2, 9.2, 2.7 Hz, 1H), 3.51 (apparent t, J=4.4 Hz, 1H), 3.50 (dd, J=9.5, 4.2 Hz, 1H), 3.39 (dd, J=9.5, 7.1 Hz, 1H), 3.28 (s, 3H), 2.86 (d, J=3.2 Hz, 1H), 1.85 (qdd, J=7.3, 5.2, 2.9 Hz, 1H), 1.76 (dqd, J=9.3, 6.9, 4.0 Hz, 1H), 1.71 (ddd, J=14.5, 9.0, 2.8 Hz, 1H), 1.55 (ddd, J=14.4, 9.2, 2.9 Hz, 1H), 0.96 (d, J=7.3 Hz, 3H), 0.88 (s, 9H), 0.81 (d, J=6.8 Hz, 3H), 0.03 (s, 3H), −0.01 (s, 3H); $^{13}$C NMR d 138.2, 128.4, 127.7, 101.2, 76.7, 74.7, 73.3, 73.0, 67.4, 56.7, 41.1, 36.0, 34.7, 25.9, 18.1, 13.7, 9.7, −4.6, −4.9; high resolution mass spectrum (FAB, NBA) m/z 461.2715 [(M+Na)$^+$; calcd for $C_{24}H_{42}O_5SiNa$: 461.2699].

EXAMPLE 29

Methyl Pyranoside 36

A solution of 35 (281.2 mg, β/α=2:1, 0.642 mmol) and 2,6-lutidine (224.0 μL, 1.92 mmol) in $CH_2Cl_2$ (6.0 mL) was cooled to 0° C. and TBSOTf (295.0 μL, 1.28 mmol) was added over 5 min. After 1 h at 0° C., the mixture was diluted with ethyl acetate (100 mL), washed with aqueous $NaHSO_4$ (1.0 M, 50 mL), brine (100 mL), dried over $MgSO_4$, filtered and concentrated. Flash chromatography (5% ethyl acetate/ hexane) provided 36 (344.6 mg, β/α=2:1, 97% yield) as a colorless oil.

α anomer: $[\alpha]^{23}_D$ +50.0° (c 1.44, $CHCl_3$); IR ($CHCl_3$) 2960 (s), 2935 (s), 2885 (s), 2860 (s), 1490 (w), 1460 (m), 1388 (m), 1378 (m), 1360 (m), 1250 (s), 1190 (m), 1145 (m) 1105 (s), 1085 (s), 1050 (s), 1025 (s), 1002 (s), 963 (m), 934 (m), 867 (m), 833 (s), 690 (m) cm$^{-1}$; $^1$H NMR (500 MHZ, $CDCl_3$) d 7.32–7.25 (m, 5H), 4.51 (ABq, $J_{AB}$=12.1 Hz, $\Delta\delta_{AB}$=19.7 Hz, 2H), 4.23 (d, J=4.8 Hz, 1H), 4.03 (dddd, J=8.0, 5.3, 5.3, 2.5 Hz, 1H), 3.87 (ddd, J=9.9, 7.8, 1.8 Hz, 1H), 3.53 (dd, J=7.2, 4.8 Hz, 1H), 3.39 (dd, J=9.8, 5.6 Hz, 1H), 3.37 (dd, J=10.0, 5.2 Hz, 1H), 3.33 (s, 3H), 1.79 (dqd, J=7.1, 7.1, 4.9 Hz, 1H), 1.71–1.64 (m, 2H), 1.53 (ddd, J=14.4, 8.8, 1.9 Hz, 1H), 0.94 (d, J=7.0 Hz, 3H), 0.89 (s, 9H), 0.865 (s, 9H), 0.862 (d, J=6.9 Hz, 3H), 0.07 (s, 3H), 0.04 (s, 3H), 0.03 (s, 3H), 0.005 (s, 3H); $^{13}$C NMR (125 MHZ, $CDCl_3$) d 138.5, 128.3, 127.6, 127.5, 103.8, 75.5, 73.2, 72.8, 69.8, 69.1, 55.7, 38.9, 38.5, 37.6, 26.0, 25.8, 18.18, 18.16, 15.1, 12.9, −3.9, −4.6, −4.7, −4.8; high resolution mass spectrum (FAB, NBA) m/z 575.3552 [(M+Na)$^+$; calcd for $C_{30}H_{56}O_5Si_2Na$: 575.3564].

β anomer: $[\alpha]^{23}_D$ +13.3° (c 1.38, $CHCl_3$); IR ($CHCl_3$) 3003 (m), 2960 (s), 2935 (s), 2880 (s), 2860 (s), 1495 (w), 1470 (m), 1464 (m), 1390 (m), 1360 (m), 1350 (m), 1330 (w), 1253 (s), 1155 (s), 1140 (s), 1120 (s), 1090 (s), 1045 (s), 1022 (s), 1002 (s), 953 (m), 933 (m), 850 (s), 830 (s), 690 (m), 658 (m) cm$^{-1}$; $^1$H NMR (500 MHZ, $CDCl_3$) d 7.32–7.22 (m, 5H), 4.74 (d, J=2.4 Hz, 1H), 4.50 (ABq, $J_{AB}$=13.2 Hz, $\Delta\delta_{AB}$=17.8 Hz, 2H), 4.23–4.18 (m, 1H), 3.74 (ddd, J=10.6, 10.6, 1.3 Hz, 1H), 3.60 (apparent t, J=2.7 Hz, 1H), 3.48 (s, 3H), 3.38 (dd, J=9.8, 4.5 Hz, 1H), 3.35 (dd, J=9.8, 5.7 Hz, 1H), 1.88 (qdd, J=7.1, 2.7, 2.7 Hz, 1H), 1.66 (ddd, J=14.0, 10.1, 1.6 Hz, 1H), 1.63–1.55 (m, 1H), 1.49 (ddd, J=14.0, 10.8, 1.8 Hz, 1H), 0.91 (d, J=7.1 Hz, 3H), 0.89 (s, 9H), 0.88 (s, 9H), 0.785 (d, J=6.8 Hz, 3H), 0.07 (s, 3H), 0.045 (s, 3H), 0.040 (s, 3H), 0.02 (s, 3H); $^{13}$C NMR (125 MHZ, $CDCl_3$) d 138.5, 128.2, 127.6, 127.4, 100.6, 76.9, 75.8, 73.2, 71.7, 67.9, 56.7, 41.1, 38.4, 35.0, 26.1, 25.8, 18.2, 18.1, 14.0, 9.7, −3.9, −4.5, −5.0; high resolution mass spectrum (FAB, NBA) m/z 575.3560 [(M+Na)$^+$; calcd for $C_{30}H_{56}O_5Si_2Na$: 575.3564].

EXAMPLE 30

Primary Alcohol 37

A solution of 36 (331.6 mg, 0.600 mmol) in EtOH/EtOAc (1:8, 9 mL) was treated with Pd/C (10% wet, E101 NE/W, 51.2 mg) under $H_2$ atmosphere for 3 h, then filtered and concentrated. Flash chromatography (10% ethyl acetate/ hexane) provided 37 (276.6 mg, β/α=2:1, 99% yield) as a colorless oil.

β anomer: $[\alpha]^{23}_D$ +16.9° (c 2.52, $CHCl_3$); IR ($CHCl_3$) 3680 (w), 3590 (w, br), 3450 (w, br), 3000 (m), 2960 (s), 2925 (s), 2880 (m), 2855 (s), 1470 (m), 1462 (m), 1388 (m), 1360 (m), 1253 (s), 1222 (m), 1200 (m), 1150 (m), 1130 (m), 1110 (s), 1098 (m), 1065 (s), 1046 (s), 1023 (s), 1002 (m), 980 (m), 952 (m), 894 (m), 865 (m), 850 (m), 830 (s), 663 (m), 657 (m) cm$^{-1}$; $^1$H NMR (500 MHZ, $CDCl_3$) d 4.73 (d, J=2.5 Hz, 1H), 4.09–4.05 (m, 1H), 3.64 (ddd, J=10.5, 10.5, 1.3 Hz, 1H), 3.60 (apparent t, J=2.5 Hz, 1H), 3.62–3.59 (m, 1H), 3.47 (s, 3H), 3.47–3.42 (m, 1H), 1.95–1.85 (m, 2H), 1.82 (ddd, J=14.3, 9.2, 1.5 Hz, 1H), 1.60 (dqd, J=10.2, 6.8, 2.5 Hz, 1H), 1.45 (ddd, J=14.3, 10.7, 2.6 Hz, 1H), 0.895 (d, J=7.5 Hz, 3H), 0.887 (apparent s, 18H), 0.785 (d, J=6.8 Hz, 3H), 0.09 (s, 3H), 0.08 (s, 3H), 0.04 (s, 3H), 0.02 (s, 3H); $^{13}$C NMR (125 MHZ, $CDCl_3$) d 100.8, 76.8, 72.2, 69.5, 67.6, 56.8, 41.0, 38.2, 34.9, 25.9, 25.8, 18.1, 14.0, 9.7, −4.2, −4.6, −4.7, −5.0; high resolution mass spectrum (FAB, NBA) m/z 485.3080 [(M+Na)$^+$; calcd for $C_{23}H_{50}O_5SiNa$: 485.3094].

α anomer: $[\alpha]^{23}_D$ +54.9° (c 1.20, $CHCl_3$); IR ($CHCl_3$) 3670 (w), 3590 (w) 3440 (w, br), 3000 (m), 2960 (s), 2925 (s), 2880 (m), 2855 (s), 1463 (m), 1390 (m), 1360 (m), 1255 (s), 1225 (m), 1192 (m), 1168 (m), 1143 (m), 1102 (s), 1083 (s), 1045 (s), 1030 (m), 1002 (m), 963 (m), 932 (m), 862 (m), 833 (s) cm$^{-1}$; $^1$H NMR (500 MHZ, $CDCl_3$) d 4.25 (d, J=4.2 Hz, 1H), 3.89 (dddd, J=6.5, 4.6, 4.6, 4.6 Hz, 1H), 3.80 (ddd, J=9.1, 9.1, 2.3 Hz, 1H), 3.61 (br dd, J=10.9, 3.4 Hz, 1H), 3.51 (dd, J=6.5, 4.6 Hz, 1H), 3.52–3.48 (m, 1H), 3.33 (s, 3H), 2.15 (s, br, 1H), 1.81 (dqd, J=6.9, 6.9, 4.2 Hz, 1H), 1.72–1.60 (m, 3H), 0.94 (d, J=7.1 Hz, 3H), 0.882 (s, 9H), 0.879 (s, 9H), 0.845 (d, J=6.8 Hz, 3H), 0.09 (s, 3H), 0.08 (s, 3H), 0.02 (s, 3H), 0.00 (s, 3H); $^{13}$C NMR (125 MHz, $CDCl_3$) d 104.0, 72.7, 71.3, 70.0, 67.6, 55.7, 38.7, 38.5, 37.3, 25.8, 18.13, 18.08, 15.2, 13.1, −4.4, −4.6, −4.7; high resolution mass spectrum (FAB, NBA) m/z 485.3081 [(M+Na)$^+$; calcd for $C_{23}H_{50}O_5Si_2Na$: 485.3094].

EXAMPLE 31

Alcohol 38

A solution of 37 (276.6 mg, 0.598 mmol) in $Et_2O$ (40 mL) was treated with EtSH (8.90 mL, 120 mmol) and $MgBr_2.Et_2O$ (1.54 g, 5.96 mmol) at room temperature. After 60 h, the mixture was diluted with ethyl acetate (50 mL), washed with brine (2×100 mL), dried over $MgSO_4$, filtered and concentrated. Flash chromatography (3% acetone/ hexane) provided 38 α (34.4 mg, 12% yield) and 38 β (211.3 mg, 71% yield).

β anomer: colorless oil; $[\alpha]^{23}_D$ +16.6° (c 1.18, $CHCl_3$); IR ($CHCl_3$) 3595 (m), 3400 (m, br), 3000 (m), 2960 (s), 2930 (s), 2855 (s), 1655 (w), 1612 (s), 1588 (m), 1510 (s) 1462 (s), 1375 (m), 1360 (m), 1300 (m), 1250 (s, br), 1170 (m), 1080 (s, br), 1030 (s), 1002 (m), 967 (m), 835 (s) cm$^{-1}$; $^1$H NMR (500 MHZ, $CDCl_3$) d 5.08 (d, J=2.3 Hz, 1H), 4.04–4.00 (m, 1H), 3.62 (ddd, J=10.4, 10.4, 1.0 Hz, 1H), 3.60 (ddd, J=11.1, 11.1, 4.2 Hz, 1H), 3.56 (apparent t, J=2.7 Hz, 1H), 3.43 (ddd, J=11.7, 7.9, 4.1 Hz, 1H), 2.70 (dq, J=12.7, 7.4 Hz, 1H), 2.67 (dq, J=12.8, 7.5 Hz, 1H), 1.95 (dd, J=7.9, 4.8 Hz, 1H), 1.86 (qdd, J=7.1, 2.7, 2.7 Hz, 1H), 1.79 (ddd, J=14.4, 9.0, 1.4 Hz, 1H), 1.66–1.59 (m, 1H), 1.57 (s, 1H), 1.45 (ddd, J=14.4, 10.5, 2.7 Hz, 1H), 1.27 (apparent t, J=7.4 Hz, 1H), 0.99 (d, J=7.1 Hz, 3H), 0.90 (s, 9H), 0.89 (s, 9H), 0.79 (d, J=6.8 Hz, 3H), 0.083 (s, 3H), 0.075 (s, 3H), 0.04 (s, 3H), 0.03 (s, 3H); $^{13}$C NMR (125 MHZ, CDCl$_3$) d 81.0, 76.2, 75.0, 69.8, 67.6, 41.9, 38.3, 34.5, 25.9, 25.8, 25.2, 18.1, 15.2, 14.4, 11.5, −4.2, −4.56, −4.63, −4.9; high resolution mass spectrum (FAB, NBA) m/z 515.3037 [(M+Na); calcd for C$_{24}$H$_{52}$O$_4$SSi$_2$Na: 515.3023].

α anomer: colorless oil; $[\alpha]^{23}_D$ +94.5° (c 0.33, CHCl$_3$); IR (CHCl$_3$) 3680 (w), 3580 (w), 3440 (w, br), 3010 (m), 2960 (s), 2930 (s), 2880 (m), 2860 (s), 1513 (w), 1470 (m), 1462 (m), 1390 (m), 1380 (m), 1360 (m), 1257 (s), 1225 (m), 1200 (m), 1114 (m), 1070 (s), 1047 (s), 1022 (m), 1002 (m), 957 (m), 860 (m), 833 (s), 705 (s), 660 (m) cm$^{-1}$; $^1$H NMR (500 MHZ, CDCl$_3$) d 4.76 (d, J=3.1 Hz, 1H), 4.04 (ddd, J=9.8, 9.8, 1.8 Hz, 1H), 3.84 (dddd, J=5.0, 5.0, 5.0, 5.0 Hz, 1H), 3.57 (dd, J=11.0, 4.2 Hz, 1H), 3.53 (apparent t, J=4.0 Hz, 1H), 3.47 (dd, J=11.0, 4.7 Hz, 1H), 2.57 (dq, J=12.8, 7.5 Hz, 1H), 2.54 (dq, J=12.8, 7.5 Hz, 1H), 1.97–1.91 (m, 1H), 1.75 (ddd, J=14.7, 6.1 Hz, 2.0, 1H), 1.72–1.65 (m, 1H), 1.60 (ddd, J=14.9, 10.0, 5.1 Hz, 1H), 1.60–1.50 (br, 1H), 1.23 (apparent t, J=7.4 Hz, 3H), 1.06 (d, J=7.1 Hz, 3H), 0.92 (s, 9H), 0.89 (s, 9H), 0.85 (d, J=6.9 Hz, 3H), 0.12 (s, 3H), 0.08 (s, 3H), 0.05 (s, 3H), 0.02 (s, 3H); $^{13}$C NMR (125 MHZ, CDCl$_3$) d 85.3, 73.8, 71.5, 69.2; 67.5, 40.6, 38.2, 36.4, 26.4, 26.1, 25.9, 18.2, 18.1, 17.5, 14.7, 13.9, −4.2, −4.4, −4.8; high resolution mass spectrum (FAB, NBA) m/z 515.3045 [(M+Na)$^+$; calcd for C$_{24}$H$_{52}$O$_4$SSi$_2$Na: 515.3023].

EXAMPLE 32

Fragment (+)-C

A solution of DMSO (100 μL, 1.42 mmol) in CH$_2$Cl$_2$ (2.0 mL) was cooled to −78° C. and oxalyl chloride (55.0 μl, 0.630 mmol) was introduced dropwise. After 15 min. a cooled (−78° C.) solution of 38 α (104.8 mg, 0.213 mmol) in CH$_2$Cl$_2$ (1.0 mL) was introduced via cannula (2×500 μL rinse). The resultant milky solution was stirred for 15 min at −78° C. and i-Pr$_2$NEt (370 μl, 2.12 mmol) was added dropwise. The reaction mixture was stirred for 0.5 h, slowly warmed to room temperature (15 min), and quenched with aqueous NaHSO$_4$ (1.0 M, 4.0 mL). The organic phase was diluted with ether (30 mL), washed with brine (3×30 mL), dried over MgSO$_4$, filtered and concentrated. Flash chromatography (2% ethyl acetate/hexane) furnished (+)-C (88.8 mg, 86% yield) as a colorless oil: $[\alpha]^{23}_D$ +11.2° (c 1.42, CHCl$_3$); IR (CHCl$_3$) 2960 (s), 2935 (s), 2880 (s), 2860 (s), 1735 (s), 1470 (m), 1460 (m), 1380 (m), 1360 (m), 1320 (m), 1295 (w), 1265 (s), 1153 (m), 1120 (m), 1080 (m), 1060 (s), 1043 (s), 1025 (s), 1003 (s), 970 (m), 950 (m), 935 (m), 903 (m), 865 (m), 835 (s), 800 (m), 690 (m) cm$^{-1}$; $^1$H NMR (500 MHZ, CDCl$_3$) d 9.56 (d, J=0.9 Hz, 1H), 5.07 (d, J=2.3 Hz, 1H), 4.35 (ddd, J=7.9, 2.2, 0.6 Hz, 1H), 3.70 (ddd, J=10.3, 10.3, 1.5 Hz, 1H), 3.57 (apparent t, J=2.7 Hz, 1H), 2.71–2.60 (m, 2H), 1.86 (apparent qt, J=7.1, 2.7 Hz, 1H), 1.78 (ddd, J=14.1, 10.4, 7.8 Hz, 1H), 1.72–1.66 (m, 1H), 1.67 (ddd, J=10.3, 3.9, 1.8 Hz, 1H), 1.25 (apparent t, J=7.4 Hz, 3H), 1.00 (d, J=7.2 Hz, 3H), 0.90 (s, 9H), 0.89 (s, 9H), 0.78 (d, J=6.8 Hz, 3H), 0.10 (s, 3H), 0.04 (s, 6H), 0.03 (s, 3H); $^{13}$C NMR (125 MHZ, CDCl$_3$) d 202.6, 81.2, 76.1, 74.9, 73.7, 41.9, 35.8, 34.4, 25.82, 25.79, 25.2, 18.2, 18.1, 15.3, 14.3, 11.5, −4.2, −4.5, −4.9, −5.2; high resolution mass spectrum (CI, NH$_3$) m/z 491.3058 [(M+H)$^+$; calcd for C$_{24}$H$_{51}$O$_4$SSi$_2$: 491.3046].

EXAMPLE 33

Fragment (−)-B

From vinyl bromide (−)-22: A solution of (−)-22 (3.78 g, 8.04 mmol) in HMPA/DMF (2:1, 6 mL) was added to a mixture of KI (4.15 g, 250 mmol), NiBr$_2$ (34.9 mg, 0.160 mmol), and Zn powder (23.2 mg, 0.355 mmol). The mixture was stirred at room temperature for 15 min then heated to 90° C. The green color mixture turned black-brown after 5 min and dark green after 1 h. After additional 1 h at 90° C., the mixture was cooled to room temperature, diluted with ethyl acetate (200 mL), washed with brine (4×200 mL), dried over MgSO$_4$, filtered and concentrated. Flash chromatography (2% ethyl acetate/hexane) provided B (3.59 g, containing 13% unreacted vinyl bromide) as a colorless oil.

From aldehyde (+)-18: A suspension of EtPh$_3$P$^+$I$^-$ (15.1 g, 36.1 mmol) in THF (200 mL) was treated with n-BuLi (1.6 M in hexane, 23.0 mL, 36.8 mmol) at room temperature over 10 min. After an additional 10 min, the resultant red solution was added via cannula to a cooled (−78° C.) solution of I$_2$ (8.02 g, 31.6 mmol) in THF (300 mL) over 15 min. The yellow slurry formed was stirred at −78° C. for 5 min and at −23° C. for 10 min. NaHMDS (1.0 M in THF, 31.0 mL, 31.0 mmol) was added over 8 min and the mixture stirred 15 min further. A solution of aldehyde (+)-18 (6.96 g, 18.3 mmol) in THF (50 mL) was introduced via cannula (10 mL rinse), and the reaction mixture was stirred at −23° C. for 10 min, warmed to room temperature, stirred for 3 h, and then quenched with MeOH (10 mL). Following concentration and filtration through a silica column (50% ethyl acetate/hexane), the filtrate was washed with saturated aqueous Na$_2$S$_2$O$_3$, brine (300 mL each), dried over MgSO$_4$, filtered and concentrated. Flash chromatography (5% ethyl acetate/hexane) furnished B (6:1 Z/E, 3.94 g, 41% yield) as a colorless oil.

An analytical sample of (−)-B was obtained by reversed-phase HPLC (gradient elution, 90% CH$_3$CN/H$_2$O→100% CH$_3$CN): $[\alpha]^{23}_D$ −23° (c 0.30, CHCl$_3$); IR (CHCl$_3$) 3000 (m), 2960 (s), 2930 (s), 2880 (m), 2855 (s), 1610 (m), 1588 (w), 1510 (s), 1463 (m), 1453 (m), 1428 (m), 1405 (w), 1390 (m), 1377 (m), 1360 (m), 1303 (m), 1250 (s), 1180 (m), 1172 (m), 1080 (s, br), 1033 (s), 1002 (m), 948 (m), 935 (m), 922 (m), 833 (s) 803 (m), 760 (m, br), 720 (m), 658 (m) cm$^{-1}$; $^1$H NMR (500 MHZ, CDCl$_3$) d 7.25 (d, J=8.6 Hz, 2H), 6.87 (d, J=8.7 Hz, 2H), 5.28 (apparent dd, J=8.9, 1.4 Hz, 1H), 4.41 (ABq, J$_{AB}$=7.0 Hz, Δδ$_{AB}$=10.2 Hz, 2H), 3.80 (s, 3H), 3.60 (apparent t, J=5.3 Hz, 1H), 3.51 (dd, J=9.1, 5.1 Hz, 1H), 3.23 (dd, J=9.0, 8.0 Hz, 1H), 2.54–2.47 (m, 1H), 2.44 (d, J=1.4 Hz, 3H), 2.00–1.92 (m, 1H), 1.00 (d, J=6.9 Hz, 3H), 0.95 (d, J=6.7 Hz, 3H), 0.89 (s, 9H), 0.02 (s, 3H), 0.01 (s, 3H); $^{13}$C NMR (125 MHZ, CDCl$_3$) d 159.1, 139.6, 131.0, 129.1, 113.7, 98.9, 76.5, 72.6, 72.5, 55.3, 44.5, 38.7, 33.5, 26.1, 18.4, 14.7, 14.5, −3.95, −3.99; high resolution mass spectrum (FAB, NBA) m/z 541.1626 [(M+Na)$^+$; calcd for C$_{23}$H$_{39}$O$_3$ISiNa: 541.1611].

EXAMPLE 34

Olefin (−)-39

ZnCl$_2$ (1.32 g, 9.69 mmol) was dried at 160° C. under vacuum overnight and then treated with a solution of (−)-A (5.25 g, 9.59 mmol) in dry Et$_2$O (50 mL) via a cannula (2×25 mL rinse). The mixture was stirred at room temperature until most of the ZnCl$_2$ dissolved and cooled to −78° C. t-BuLi (1.7 M in pentane, 17.0 mL) was added over 30 min, and the resultant solution was stirred 15 min further, warmed to room temperature, and stirred for 1 h. The solution was added by cannula to a mixture of B (3.21 g, 6.19 mmol; 6:1 Z/E) and Pd(PPh$_3$)$_4$ (364.0 mg, 0.315 mmol). The mixture was covered with aluminum foil, stirred overnight, and then diluted with ethyl acetate (100 mL), washed with brine (2×100 mL), dried over MgSO$_4$, filtered and concentrated. Flash chromatography (5% ethyl acetate/hexane) gave (−)-39 (3.32 g, 66% yield) as a white semisolid: $[\alpha]^{23}_D$ −28.6° (c 1.53, CHCl$_3$); IR (CHCl$_3$) 3010 (m), 2970 (s), 2940 (s), 2865 (s), 1620 (m), 1590 (w), 1520 (s), 1465 (s), 1445 (m), 1390 (m), 1380 (m), 1360 (m), 1305 (m), 1250 (s), 1175 (m), 1115 (s), 1080 (s), 1040 (s), 970 (m), 940 (w), 860 (m), 835 (s) cm$^{-1}$; $^1$H NMR (500 MHZ, CDCl$_3$) d 7.36 (d, J=8.7 Hz, 2H), 7.22 (d, J=8.6 Hz, 2H), 6.86 (d, J=9.0 Hz, 2H), 6.84 (d, J=8.9 Hz, 2H), 5.37 (s, 1H), 5.00 (d, J=10.2 Hz, 1H), 4.36 (ABq, J$_{AB}$=11.6 Hz, $\Delta\delta_{AB}$=17.4 Hz, 2H), 4.08 (dd, J=11.2, 4.7 Hz, 1H), 3.78 (s, 3H), 3.77 (s, 3H), 3.61 (dd, J=7.1, 1.8 Hz, 1H), 3.51 (dd, J=9.9, 1.7 Hz, 1H), 3.47 (apparent t, J=11.0 Hz, 1H), 3.46 (dd, J=9.1, 5.0 Hz, 1H), 3.38 (dd, J=6.0, 4.8 Hz, 1H), 3.19 (apparent t, J=8.8 Hz, 1H), 2.51 (ddq, J=10.1, 6.5, 6.5 Hz, 1H), 2.32 (apparent t, J=12.2 Hz, 1H), 2.08–2.02 (m, 1H), 1.99–1.93 (m, 2H), 1.88 (dqd, J=7.1, 7.1, 1.8 Hz, 1H), 1.67 (br d, J=11.1 Hz, 1H), 1.55 (d, J=0.5 Hz, 3H), 1.01 (d, J=7.1 Hz, 3H), 0.94 (d, J=6.9 Hz, 3H), 0.90 (s, 9H), 0.89 (d, J=6.7 Hz, 3H), 0.87 (s, 9H), 0.74 (d, J=6.3 Hz, 3H), 0.73 (d, J=6.4 Hz, 3H), 0.03 (s, 3H), 0.013 (s, 3H), 0.008 (s, 3H), 0.003 (s, 3H); $^{13}$C NMR (125 MHZ, CDCl$_3$) d 159.8, 159.0, 132.0, 131.5, 131.2, 131.1, 129.0, 127.3, 113.7, 113.5, 101.1, 83.4, 78.49, 78.46, 73.3, 72.6, 72.5, 55.3, 38.8, 38.2, 37.5, 35.6, 33.7, 30.8, 26.27, 26.25, 23.1, 18.42, 18.40, 17.0, 14.6, 12.6, 12.1, 10.9, −3.5, −3.7, −3.8, −3.9; high resolution mass spectrum (FAB, NBA) m/z 835.5315 [(M+Na)$^+$; calcd for C$_{47}$H$_{80}$O$_7$Si$_2$Na: 835.5341].

Anal. Calcd for C$_{47}$H$_{80}$O$_7$Si$_2$: C, 69.41; H, 9.91. Found: C, 69.52; H, 10.10.

EXAMPLE 35

Alcohol (−)-40

A solution of olefin (−)-39 (2.65 g, 3.26 mmol) in CH$_2$Cl$_2$ (32 mL) was cooled to 0° C. and treated with H$_2$O (1.50 mL) and DDQ (774 mg, 3.41 mmol). After 4 h, the mixture was diluted with CH$_2$Cl$_2$ (20 mL), dried over MgSO$_4$, and filtered through a silica column (50% ethyl acetate/hexane). Following concentration, the residue was dissolved in EtOH (50 mL) and treated with NaBH$_4$ (500 mg, excess) at room temperature to reduce the contaminated p-methoxybenzyl aldehyde. After 0.5 h, the mixture was quenched with saturated aqueous NH$_4$Cl (50 mL) at 0° C. then concentrated. The residue was partitioned between CH$_2$Cl$_2$ (200 mL) and water (100 mL). The organic phase was washed with water (100 mL), dried over MgSO$_4$, filtered and concentrated. Flash chromatography (10% ethyl acetate/hexane) provided (−)-40 (2.06 g, 91% yield) as a white solid. mp 99–100° C.; [α]$^{23}_D$ −25.4° (c 1.35, CHCl); IR (CHCl$_3$) 3520 (w), 3010 (m), 2960 (s), 2940 (s), 2880 (m), 2860 (m), 1620 (m), 1593 (w), 1520 (m), 1565 (m), 1390 (m), 1360 (m), 1255 (s), 1175 (m), 1165 (m), 1117 (m), 1075 (s), 1037 (s), 1025 (s), 1005 (m), 982 (m), 965 (m), 930 (w), 835 (s), 800 (m), 705 (w), 675 (w), 660 (w) cm$^{-1}$; $^1$H NMR (500 MHZ, CDCl$_3$) d 7.36 (d, J=8.7 Hz, 2H), 6.86 (d, J=8.8 Hz, 2H), 5.37 (s, 1H), 5.01 (d, J=10.1 Hz, 1H), 4.09 (dd, J=11.2, 4.7 Hz, 1H), 3.79 (s, 3H), 3.65 (dd, J=10.4, 4.7 Hz, 1H), 3.63 (dd, J=7.0, 1.8 Hz, 1H), 3.54–3.50 (m, 1H), 3.51 (dd, J=10.0, 2.0 Hz, 1H), 3.47 (apparent t, J=11.2 Hz, 1H), 3.41 (dd, J=6.6, 4.0 Hz, 1H), 2.59 (ddq, J=13.2, 6.7, 6.7 Hz, 1H), 2.33 (apparent t, J=12.2 Hz, 1H), 2.24 (apparent t, J=5.5 Hz, 1H), 2.09–1.95 (m, 2H), 1.89 (dqd, J=7.0, 7.0, 1.7 Hz, 1H), 1.84–1.77 (m, 1H), 1.72 (br d J=11.0 Hz, 1H), 1.58 (d, J=0.8 Hz, 3H), 1.01 (d, J=7.1 Hz, 3H), 0.98 (d, J=7.1 Hz, 3H), 0.94 (d, J=6.7 Hz, 3H), 0.910 (s, 9H), 0.905 (s, 9H), 0.75 (d, J=7.1 Hz, 3H), 0.74 (d, J=7.1 Hz, 3H), 0.09 (s, 3H), 0.07 (s, 3H), 0.05 (s, 3H), 0.01 (s, 3H); $^{13}$C NMR (125 MHZ, CDCl$_3$) d 159.8, 133.0, 131.5, 130.5, 127.3, 113.4, 101.0, 83.3, 81.6, 78.4, 73.3, 65.4, 55.3, 38.5, 38.2, 37.6, 37.0, 33.7, 30.8, 26.17, 26.16, 23.2, 18.4, 18.3, 17.4, 15.7, 12.6, 12.1, 10.9, −3.57, −3.61, −3.66, −3.9; high resolution mass spectrum (CI, NH$_3$) m/z 693.4918 [(M+H)$^+$; calcd for C$_{39}$H$_{73}$O$_6$Si$_2$: 693.4945].

Anal. Calcd for C$_{39}$H$_{72}$O$_6$Si$_2$: C, 67.58; H, 10.47. Found: C, 67.30; H, 10.54.

EXAMPLE 36

Phosphonium Salt (−)-49

A solution of alcohol (−)-40 (402.8 mg, 0.577 mmol) in PhH/Et$_2$O (1:2, 45 mL) was treated with PPh$_3$ (532 mg, 2.03 mmol) and imidazole (158 mg, 2.32 mmol). After the imidazole dissolved, I$_2$ (437 mg, 1.72 mmol) was added under vigorous stirring. The mixture was stirred 2 h and then treated with NEt$_3$ (2 mL). The resultant yellow suspension was diluted with CH$_2$Cl$_2$ (50 mL) and washed with saturated aqueous Na$_2$S$_2$O$_3$ (100 mL), saturated aqueous NaHCO$_3$ (100 mL), and brine (2×100 mL). The organic phase was dried over MgSO$_4$, filtered and concentrated. Filtration through a short silica column (NEt$_3$/ethyl acetate/hexane, 2:10:90) removed triphenylphosphine oxide, affording the impure iodide 42. Preparative TLC (500 mm silica gel plate, 40% acetone/hexane) furnished an analytical sample as an unstable white solid: $^1$H NMR (500 MHZ, CDCl$_3$) d 7.35 (d, J=8.8 Hz, 2H), 6.85 (d, J=8.7 Hz, 2H), 5.37 (s, 1H), 5.02 (d, J=10.2 Hz, 1H), 4.08 (dd, J=11.2, 4.7 Hz, 1H), 3.78 (s, 3H), 3.62 (dd, J=7.0, 1.8 Hz, 1H), 3.51 (dd, J=9.9, 1.7 Hz, 1H), 3.47 (apparent t, J=11.1 Hz, 1H), 3.37 (dd, J=6.3, 4.3 Hz, 1H), 3.32 (dd, J=9.6, 4.5 Hz, 1H), 2.99 (dd, J=9.5, 8.6 Hz, 1H), 2.50 (ddq, J=10.2, 6.5, 6.5 Hz, 1H), 2.31 (apparent t, J=12.2 Hz, 1H), 2.08–1.95 (m, 2H), 1.88 (dqd, J=7.1, 7.1, 1.7 Hz, 1H), 1.85–1.78 (m, 1H), 1.74 (br d, J=11.7 Hz, 1H), 1.57 (apparent s, 3H), 1.01 (apparent d, J=7.0 Hz, 6H), 0.91–0.89 (m, 3H), 0.90 (s, 9H), 0.89 (s, 9H), 0.74 (d, J=6.8 Hz, 3H), 0.73 (d, J=6.7 Hz, 3H), 0.06 (s, 3H), 0.05 (s, 3H), 0.01 (s, 3H), −0.02 (s, 3H); $^{13}$C NMR (125 MHZ, CDCl$_3$/1% pyridine-d$_5$, 20 mg sample) d 159.8, 132.9, 131.5, 130.4, 127.3, 113.5, 101.1, 83.3, 79.6, 78.5, 73.3, 55.3, 41.4, 38.3, 37.6, 36.0, 33.7, 30.8, 26.20, 26.17, 23.2, 18.4, 17.7, 17.3, 13.5, 12.6, 12.2, 10.9, −3.5, −3.6, −4.0; high resolution mass spectrum (FAB, NBA) m/z 803.3935 [(M+H)$^+$; calcd for C$_{39}$H$_{72}$O$_5$ISi$_2$: 803.3963].

The very sensitive impure iodide (obtained by filtration through silica) was quickly mixed with i-Pr$_2$NEt (300 μL, 1.72 mmol) and PPh$_3$ (2.47 g, 9.42 mmol). The mixture was heated at 80° C. for 24 h, then cooled to room temperature and extracted with hexane (2×30 mL). The residue was purified by flash chromatography (2% MeOH/CHCl$_3$) furnishing (−)-49 (224.9 mg, 37% yield from (−)-39) as a pale yellow foam. The hexane extract was concentrated and purified by flash chromatography (2% ethyl acetate/hexane) affording a mixture of cyclization products (200 mg). Further purification by normal phase HPLC (1.5% ethyl acetate/hexane) provided (−)-50 as the major cyclization product.

Wittig reagent (−)-49: [α]$^{23}_D$ −25.3° (c 1.48, CHCl$_3$); IR (CHCl$_3$) 2960 (s), 2930 (s), 2860 (m), 1615 (m), 1590 (w), 1515 (m), 1485 (w), 1460 (m), 1440 (m), 1385 (m), 1360 (m), 1300 (m), 1250 (s), 1215 (m, br), 1180 (m), 1110 (s), 1080 (m), 1025 (m), 1005 (m), 965 (m), 945 (w), 860 (m), 830 (s), 732 (m), 725 (m), 710 (m), 680 (m), 653 (m) cm$^{-1}$; $^1$H NMR (500 MHZ, CDCl$_3$; concentration dependent) d 7.82–7.76 (m, 15H), 7.35 (d, J=8.8 Hz, 2H), 6.84 (d, J=8.8 Hz, 2H), 5.35 (s, 1H), 5.30 (d, J=10.5 Hz, 1H), 4.07 (dd, J=11.2, 4.7 Hz, 1H), 3.77 (s, 3H), 3.73–3.67 (m, 2H), 3.56 (dd, J=7.0, 1.8 Hz, 1H), 3.48 (dd, J=9.8, 1.7 Hz, 1H), 3.46 (apparent t, J=11.1 Hz, 1H), 3.31 (ddd, J=15.6, 11.2, 11.2 Hz, 1H), 2.49 (ddq, J=10.5, 6.4, 6.4 Hz, 1H), 2.25 (apparent t, J=12.1 Hz, 1H), 2.10–1.92 (m, 3H), 1.85 (dqd, J=7.1, 7.1, 1.8 Hz, 1H), 1.57–1.52 (m, 1H), 1.56 (s, 3H), 0.98 (d, J=7.1 Hz, 3H), 0.89 (d, J=6.6 Hz, 3H), 0.852 (s, 9H), 0.849 (s, 9 H), 0.72–0.71 (m, 3H), 0.71 (d, J=6.6 Hz, 3H), 0.69 (d, J=6.9 Hz, 3H), 0.10 (s, 3H), −0.02 (s, 3H), −0.03 (s, 3H), −0.07 (s, 3H); $^{13}$C NMR (125 MHZ, CDCl$_3$) d 159.8, 135.2 (J$_{CP}$=2.6 Hz), 133.5 (J$_{CP}$=10.0 Hz), 132.9, 131.4, 130.6 (J$_{CP}$=12.6

Hz), 130.3, 127.3, 118.4 ($J_{CP}$=85.5 Hz), 113.4, 101.0, 83.2, 80.1 ($J_{CP}$=14.0 Hz), 78.3, 73.2, 55.3, 38.1, 37.4, 36.0, 33.7 ($J_{CP}$=4.4 Hz), 33.6, 30.7, 26.1, 25.5 ($J_{CP}$=49.7 Hz), 22.9, 18.33, 18.29, 17.2, 17.1, 12.5, 12.1, 10.9, −3.2, −3.6, −3.7, −4.0; high resolution mass spectrum (FAB, NBA) m/z 937.5708 [(M-I)$^+$; calcd for $C_{57}H_{86}O_5PSi_2$: 937.5751].

Olefin (−)50: white solid; mp 80–82° C.; $[\alpha]^{23}_D$ −18° (c 0.48, CHCl$_3$); IR (CHCl$_3$) 2955 (s), 2920 (s), 2880 (m), 2850 (s), 1640 (w), 1613 (m), 1588 (w), 1517 (m), 1460 (m), 1387 (m), 1360 (m),1300 (m), 1250 (s), 1178 (m), 1170 (m), 1160 (m), 1115 (m), 1080 (m), 1023 (s), 1000 (m), 980 (m), 960 (m), 930 (w), 887 (m), 855 (m), 830 (m), 715 (m) cm$^{-1}$; $^1$H NMR (500 MHZ, $C_6D_6$) d 7.62 (d, J=8.7 Hz, 2H), 6.83 (d, J=8.7 Hz, 2H), 5.46 (s, 1H), 5.00 (s, 1H), 4.95 (s, 1H), 3.93 (dd, J=11.1, 4.7 Hz, 1H), 3.89 (dd, J=7.2, 1.5 Hz, 1H), 3.55 (dd, J=9.9, 1.9 Hz, 1H), 3.51 (apparent t, J=5.9 Hz, 1H), 3.27 (s, 3H), 3.22 (apparent t, J=11.0 Hz, 1H), 2.32 (dd, J=13.6, 3.5 Hz, 1H), 2.27–2.20 (m, 1H), 2.16 (dd, J=13.7, 9.5 Hz, 1H), 2.07–1.92 (m, 4H), 1.87–1.80 (m, 1H), 1.50–1.42 (m, 1H), 1.18 (d, J=7.1 Hz, 3H), 1.10 (d, J=6.6 Hz, 3H), 1.06 (d, J=6.6 Hz, 3H), 1.04 (s, 9H), 1.02 (d, J=7.0 Hz, 3H), 1.00 (s, 9H), 0.41 (d, J=6.7 Hz, 3H), 0.13 (s, 3H), 0.09 (s, 3H), 0.08 (s, 3H), 0.06 (s, 3H); $^{13}$C NMR (125 MHZ, CDCl$_3$) d 159.8 (q), 150.7 (q), 131.5 (q), 127.3, 113.4, 108.3 (CH$_2$), 101.0, 83.2, 81.9, 78.1, 73.3 (CH$_2$), 55.2, 49.9, 44.9, 41.4 (CH$_2$), 39.0 (CH$_2$), 38.3, 36.6, 33.4, 30.8, 26.3, 25.9, 18.5 (q), 18.2 (q), 17.8, 15.5, 12.9, 12.1, 11.0, −3.4, −3.7, −4.6, −4.7; high resolution mass spectrum (FAB, NBA) m/z 697.4642 [(M+Na)$^+$; calcd for $C_{39}H_{70}O_5Si_2Na$: 697.4659].

EXAMPLE 37
Model Olefin (+)-43

NaHMDS (0.6 M in PhMe, 9.46 mL, 5.68 mmol) was added over 10 min to a suspension of $(CH_3)_2CHP^+Ph_3$ I$^-$ (2.52 g, 5.83 mmol) in PhMe (20 mL) at room temperature. After 15 min, the mixture was cooled to −78° C., and aldehyde (+)-18 (1.46 g, 3.84 mmol) in PhMe (15 mL) was introduced via a cannula (15 mL rinse). After 20 min at −78° C. and 30 min at room temperature, the reaction was quenched with MeOH (1.0 mL). The solution was separated, and the oil residue was extracted with hexane (3×30 mL). The combined organic solutions were then concentrated and, and flash chromatography (2% ethyl acetate/hexane) provided (+)-43 (1.44 g, 92% yield) as a colorless oil: $[\alpha]^{23}_D$ +8.07° (c 2.57, CHCl$_3$); IR (CHCl$_3$) 2960 (s), 2925 (s), 2880 (s), 2855 (s), 1610 (m), 1585 (m), 1510 (s), 1460 (s), 1375 (m), 1360 (m), 1300 (m), 1245 (s), 1172 (m), 1085 (s, br), 1035 (s), 1003 (m), 970 (m), 950 (m), 935 (m), 862 (s), 835 (s) cm$^{-1}$; $^1$H NMR (500 MHZ, CDCl$_3$) d 7.23 (d, J=9.0 Hz, 2H), 6.85 (d, J=8.6 Hz, 2H), 4.92 (d-quintet, J=9.7, 1.4 Hz, 1H), 4.37 (apparent s, 2H), 3.78 (s, 3H), 3.49 (dd, J=9.2, 4.9 Hz, 1H), 3.39 (dd, J=6.3, 4.5 Hz, 1H), 3.19 (dd, J=9.0, 8.4 Hz, 1H), 2.49 (ddq, J=9.6, 6.7, 6.7 Hz, 1H), 2.00–1.92 (m, 1H), 1.63 (d, J=1.2 Hz, 3H), 1.55 (d, J=1.3 Hz, 3H), 0.945 (d, J=7.0 Hz, 3H), 0.874 (d, J=6.7 Hz, 3H), 0.873 (s, 9H), 0.01 (apparent s, 6H); $^{13}$C NMR (125 MHZ, CDCl$_3$) 159.0, 131.1, 129.7, 129.4, 129.1, 113.7, 78.6, 72.6, 55.3, 38.5, 36.0, 26.2, 25.8, 18.4, 17.9, 17.0, 14.8, −3.88, −3.95; high resolution mass spectrum (CI, NH$_3$) m/z 407.2984 [(M+H)$^+$; calcd for $C_{24}H_{43}O_3Si$: 407.2981].

EXAMPLE 38
Alcohol (+)-44

A mixture of olefin (+)-43 (387.6 mg, 0.954 mmol) in CH$_2$Cl$_2$ (10 mL) was treated with H$_2$O (500 μL) and DDQ (320 mg, 1.41 mmol). After 30 min at room temperature, the mixture was filtered through a short silica plug (50% ethyl acetate/hexane) and concentrated. Flash chromatography (3% ethyl acetate/hexane) provided (+)-43 (273.1 mg, 99% yield) as a colorless oil: $[\alpha]^{23}_D$ +17.5° (c 2.80, CHCl$_3$); IR (CHCl$_3$) 3620 (w), 3500 (m, br), 2955 (s), 2925 (s), 2880 (s), 2860 (s), 1460 (s), 1405 (m), 1375 (m), 1360 (m), 1337 (m), 1252 (s), 1070 (s), 1050 (s), 1015 (s), 1002 (s), 978 (m), 933 (m), 832 (s) cm$^{-1}$; $^1$H NMR (500 MHZ, CDCl$_3$) d 4.92 (apparent d quintet, J=9.7, 1.4 Hz, 1H), 3.66 (ddd, J=11.0, 4.4, 4.4 Hz, 1H), 3.52 (ddd, J=11.0, 5.5, 5.5 Hz, 1H), 3.42 (dd, J=6.8, 4.0 Hz, 1H), 2.57 (ddq, J=9.6, 6.8, 6.8 Hz, 1H), 2.45 (apparent t, J=5.2 Hz, 1H), 1.85–1.78 (m, 1H), 1.65 (d, J=1.3 Hz, 3H), 1.59 (d, J=1.3 Hz, 3H), 0.98 (d, J=7.1 Hz, 3H), 0.92 (d, J=6.8 Hz, 3H), 0.90 (s, 9H), 0.08 (s, 3H), 0.05 (s, 3H); $^{13}$C NMR (125 MHZ, CDCl$_3$) d 130.7, 128.5, 81.7, 65.5, 38.1, 37.4, 26.2, 25.8, 18.3, 17.9, 17.4, 15.9, −3.7, −3.9; high resolution mass spectrum (CI, NH$_3$) m/z 287.2418 [(M+H)$^+$; calcd for $C_{16}H_{35}O_2Si$: 287.2406].

EXAMPLE 39
Wittig reagent (+)-46

Iodine (1.08 g, 4.24 mmol) was added to a solution of alcohol (+)-44 (810 mg, 2.83 mmol), PPh$_3$ (1.11 g, 4.24 mmol) and imidazole (289 mg, 4.24 mmol) in benzene/ether (1:2, 21 mL) under vigorous stirring at room temperature. After 40 min, the mixture was diluted with ether (100 mL), washed with saturated Na$_2$S$_2$O$_3$ (50 mL), brine (100 mL), dried over MgSO$_4$, filtered and concentrated. Flash chromatography (hexane) provided a mixture of 45/47/48 (1.06 g, 97% yield, 18:1:1) as a colorless oil; This material was then treated with I-Pr$_2$NEt (928 μL, 5.33 mmol) and PPh$_3$ (7.01 g, 26.7 mmol) then heated at 80° C. for 13 h. The mixture was extracted with hexane (3×100 mL). The residue was purified by flash chromatography (2% MeOH/CHCl$_3$) providing Wittig reagent (+)-48 (207.1 mg, 38% yield from (+)-46) as a pale yellow foam. The hexane extract was concentrated and purified by flash chromatography (hexane) affording a mixture of two cyclization products (380 mg) and further purification by preparative TLC (hexane) afforded (−)-49 and (−)-50.

Wittig reagent (+)-46: $[\alpha]^{23}_D$ +4.8° (c 1.23, CHCl$_3$); IR (CHCl$_3$) 2940 (s), 2860 (m), 1588 (w), 1482 (w), 1468 (m), 1460 (m), 1440 (s), 1380 (m), 1360 (w), 1310 (w), 1253 (m), 1230 (m), 1210 (m), 1110 (s), 1080 (m), 1050 (m), 1018 (m), 1000 (m), 995 (m), 860 (m), 832 (s), 800 (m), 708 (m), 680 (m), 652 (m) cm$^{-1}$; $^1$H NMR (500 MHZ, CDCl$_3$; concentration dependent) d 7.81–7.67 (m, 15H), 4.92 (d, J=9.7 Hz, 1H), 3.50 (apparent t, J=5.3 Hz, 1H), 3.38 (ddd, J=14.9, 14.9, 1.5 Hz, 1H), 3.25 (ddd, J=15.6, 11.1, 11.1 Hz, 1H), 2.42 (ddq, J=9.7, 6.6, 6.6 Hz, 1H), 2.10–2.00 (m, 1H), 1.53 (s, 3H), 1.43 (s, 3H), 0.83 (s, 9H), 0.81 (d, J=6.7 Hz, 3H), 0.75 (d, J=6.8 Hz, 3H), 0.03 (s, 3H), −0.02 (s, 3H); $^{13}$C NMR (125 MHZ, CDCl$_3$) d, 135.3 ($J_{cp}$=2.8 Hz), 133.3 ($J_{cp}$=9.9 Hz), 131.0, 130.6 ($J_{cp}$=12.4 Hz), 128.0, 118.2 ($J_{cp}$=85.6 Hz), 80.4 ($J_{cp}$=13.3 Hz), 36.0, 33.0 ($J_{cp}$=4.0 Hz), 26.1, 25.6, 25.1 ($J_{cp}$=50.8 Hz), 18.3, 18.1, 17.9, 16.4, −3.3, −4.0; high resolution mass spectrum (FAB, NBA) m/z 531.3221 [(M-I)$^+$; calcd for $C_{34}H_{48}OPSi$: 531.3213].

Olefin (−)-47: Colorless oil; $[\alpha]^{23}_D$ −14° (c 0.36, CHCl$_3$); IR (CHCl$_3$) 2960 (s), 2930 (s), 2860 (s), 1470 (m), 1460, 1370 (m), 1360 (m), 1250 (m), 1206 (w), 1165 (m), 1140 (m), 1070 (s), 1020 (s), 1000 (m), 932 (w), 908 (w), 897 (w), 853 (m), 830 (s) cm$^{-1}$; $^1$H NMR (500 MHZ, CDCl$_3$) d 3.63 (d, br, J=3.6 Hz, 1H), 2.50 (apparent q, J=7.3 Hz, 1H), 2.28 (ddd, J=15.5, 7.7, 0.8 Hz, 1H), 2.13–2.03 (m, 1H), 1.99–1.91 (m, 1H), 1.60 (apparent br s, 3H), 1.57 (apparent d, J=0.8 Hz, 1H), 0.94 (d, J=6.7 Hz, 3H), 0.91 (d, J=7.4 Hz, 3H), 0.85 (s, 9H), 0.01 (apparent s, 6H); $^{13}$C NMR (125 MHZ, CDCl$_3$) d 138.9 (q), 122.0 (q), 82.9, 46.1, 36.4, 35.8 (CH$_2$), 25.9, 21.2, 20.4, 18.3 (q), 18.0, 14.3, −4.6, −4.8; high resolution mass spectrum (CI, $NH_3$) m/z 269.2310 [(M+H)$^+$; calcd for $C_{16}H_{33}OSi$: 269.2300].

Olefin (−)-48: Colorless oil; $[\alpha]^{23}_D$ −3.8° (c 0.24, $CHCl_3$); IR ($CHCl_3$) 2953 (s), 2925 (s), 2880 (m), 2855 (m), 1638 (w), 1470 (m), 1460 (m), 1385 (w), 1373 (m), 1360 (w), 1250 (m), 1135 (m), 1117 (m), 1100 (m), 1075 (m), 1028 (m), 1000 (m), 932 (w), 865 (m), 830 (s) cm$^{-1}$; $^1$H NMR (500 MHZ, $C_6D_6$) d 4.84–4.83 (m, 1H), 4.79–4.77 (m, 1H), 3.46 (apparent t, J=5.3 Hz, 1H), 1.94–1.88 (m, 1H), 1.87–1.78 (m, 2H), 1.73 (ddd, J=12.4, 7.3, 7.3 Hz, 1H), 1.66 (apparent dd, J 1.3, 0.8 Hz, 3H), 1.45 (ddd, J=12.2, 10.3, 8.7 Hz, 1H), 1.00 (d, J=6.9 Hz, 3H), 0.99 (s, 9H), 0.96 (d, J=6.7 Hz, 3H), 0.06 (s, 3H), 0.05 (s, 3H); $^{13}$C NMR (125 MHZ, $C_6D_6$) d 147.4 (q), 110.3 ($CH_2$), 82.3, 53.1, 45.4, 37.5 ($CH_2$), 37.3, 26.1, 19.3, 18.4 (q), 18.0, 15.6, −4.4, −4.5; high resolution mass spectrum (CI, $NH_3$) m/z 269.2315 [(M+H)$^+$; calcd for $C_{16}H_{33}OSi$: 269.2300].

EXAMPLE 40

Alcohol (+)-51

A solution of olefin (+)-44 (70.9 mg, 0.28 mmol) in EtOH/EtOAc (1:8, 4.5 mL) was treated with Pd/C (10% wet, E101 NE/W, 15.2 mg) under $H_2$ atmosphere for 18 h. The mixture was then filtered through a short silica pipet and concentrated. Flash chromatography (5% ethyl acetate/hexane) provided (+)-51 (70.8 mg, 100% yield) as a colorless oil. $[\alpha]^{23}_D$ +28° (c 0.15, $CHCl_3$); IR ($CHCl_3$) 3680 (w), 3620 (w), 3500 (w, br), 3010 (m), 2960 (s), 2935 (s), 2900 (m), 2885 (m), 2860 (m), 1522 (w), 1510 (w), 1470 (m), 1426 (m), 1420 (m), 1412 (m), 1387 (m), 1370 (m), 1255 (m), 1205 (m), 1070 (m), 1030 (m), 1013 (m), 1002 (m), 980 (m), 925 (m), 833 (s), 720 (m), 665 (m), 658 (m) cm$^{-1}$; $^1$H NMR (500 MHZ, $CDCl_3$) d 3.60–3.56 (m, 2H), 3.46 (dd, J=5.5, 3.8 Hz, 1H), 2.46 (br s, 1H), 1.89–1.81 (m, 1H), 1.74–1.66 (m, 1H), 1.64–1.56 (m, 1H), 1.21 (ddd, J=13.3, 8.9, 4.6 Hz, 1H), 1.09 (ddd, J=13.7, 9.6, 5.3 Hz, 1H), 0.94 (d, J=7.0 Hz, 3H), 0.90 (s, 9H), 0.88 (d, J=6.6 Hz, 3H), 0.86 (d, J=6.9 Hz, 3H), 0.83 (d, J=6.6 Hz, 3H), 0.095 (s, 3H), 0.07 (s, 3H); $^{13}$C NMR (125 MHZ, $CDCl_3$) d 81.3, 66.3, 42.5, 37.8, 35.7, 26.1, 25.4, 23.8, 21.8, 16.4, 15.1, −3.9, −4.1; high resolution mass spectrum (CI, $NH_3$) m/z 289.2565 [(M+H)$^+$; calcd for $C_{16}H_{37}O_2Si$: 289.2562].

EXAMPLE 41

Iodide (+)-52

A solution of alcohol (+)-51 (150 mg, 0.520 mmol), $PPh_3$ (205 mg, 0.780 mmol) and imidazole (53 mg, 0.780 mmol) in benzene/ether (1:2; 6.0 mL) was treated with iodine (198 mg, 0.780 mmol) under vigorous stirring at room temperature. After 40 min, the mixture was diluted with ether (100 mL), washed with saturated $Na_2S_2O_3$ (50 mL), brine (100 mL), dried over $MgSO_4$, filtered and concentrated. Flash chromatography (hexane) provided (+)-51 (195 mg, 94% yield) as a colorless oil: $[\alpha]^{23}_D$ +24.2° (c 2.21, $CHCl_3$); IR ($CHCl_3$) 2960 (s), 2935 (s), 2900 (m), 2860 (s), 1470 (m), 1463 (m), 1425 (w), 1405 (w), 1382 (m), 1368 (m), 1360 (m), 1290 (w), 1255 (s), 1190 (m), 1170 (m), 1082 (s), 1065 (m), 1028 (m), 1003 (m), 970 (w), 932 (w), 832 (s) cm$^{-1}$; $^1$H NMR (500 MHZ, $CDCl_3$) d 3.41 (dd, J=9.6, 3.7 Hz, 1H), 3.38 (dd, J=6.3, 2.6 Hz, 1H), 3.10 (dd, J=9.6, 7.5 Hz, 1H), 1.72–1.56 (m, 3H), 1.17 (ddd, J=13.4, 8.3, 5.4 Hz, 1H), 1.09 (ddd, J=13.3, 5.9, 2.1 Hz, 1H), 0.99 (d, J=6.8 Hz, 3H), 0.89 (s, 9H), 0.88 (d, J=6.6 Hz, 3H), 0.84 (d, J=6.6 Hz, 3H), 0.81 (d, J=6.8 Hz, 3H), 0.09 (s, 3H), 0.06 (s, 3H); $^{13}$C NMR (125 MHZ, $CDCl_3$) d 79.1, 43.7, 39.8, 33.8, 26.2, 25.3, 23.5, 22.0, 18.7, 18.5, 15.9, 14.4, −3.65, −3.71; high resolution mass spectrum (CI, $NH_3$) m/z 399.1572 [(M+H)$^+$; calcd for $C_{16}H_{36}OISi$: 399.1580].

EXAMPLE 42

Wittig Reagent (+)-53

A mixture of Iodide (+)-52 (195 mg, 0.489 mmol) and benzene (100 mL) was treated with i-$Pr_2NEt$ (85 μL, 0.488 mmol) and $PPh_3$ (1.28 g, 4.88 mmol), then heated at 70° C. for 24 h. The mixture was extracted with hexane (3×20 mL). The residue was purified by flash chromatography (3% MeOH/$CHCl_3$) furnishing (+)-53 (303 mg, 94% yield) as a white foam; $[\alpha]^{23}_D$ +3.3° (c 2.14, $CHCl_3$); IR ($CHCl_3$) 2950 (s), 2930 (s), 2855 (m), 1588 (w), 1482 (w), 1463 (m), 1438 (s), 1385 (m), 1365 (w), 1253 (m), 1225 (m), 1207 (m), 1110 (s), 1080 (m), 1032 (m), 1000 (m), 832 (s), 804 (m), 708 (m), 680 (m), 653 (m) cm$^{-1}$; $^1$H NMR (500 MHZ, $CDCl_3$) d 7.83–7.67 (m, 15H), 3.70 (ddd, J=15.6, 11.0, 11.0 Hz, 1H), 3.52 (dd, J=7.6, 1.7 Hz, 1H), 3.45 (apparent t, J=15.4 Hz, 1H), 2.08–1.97 (m, 1H), 1.70–1.62 (m, 1H), 1.51 (9 lines, J=6.5 Hz, 1H), 1.09–0.97 (m, 2H), 0.850 (s, 9H), 0.79 (d, J=6.7 Hz, 3H), 0.77 (d, J=7.9 Hz, 3H), 0.74 (d, J=6.5 Hz, 3H), 0.68 (d, J=6.8 Hz, 3H), 0.12 (s, 3H), 0.11 (s, 3H); $^{13}$C NMR (125 MHZ, $CDCl_3$) d 135.2 ($J_{cp}$=2.7 Hz), 133.6 ($J_{cp}$=9.9 Hz), 130.6 ($J_{cp}$=12.4 Hz), 118.5 ($J_{cp}$=85.5 Hz), 80.1 ($J_{cp}$=12.9 Hz), 43.5, 33.6, 32.6 ($J_{cp}$=3.7 Hz), 26.2, 25.3 ($J_{cp}$=51.1 Hz), 25.0, 23.4, 21.7, 18.6, 18.5, 13.7, −2.7, −3.8; high resolution mass spectrum (FAB,NBA) m/z 533.3369 [(M-I)$^+$; calcd for $C_{34}H_{50}OPSi$: 533.3357].

EXAMPLE 43

Olefin (−)-54

Phosphonium salt (−)-49 was dried azeotropically with anhydrous benzene and heated at 50° C. under vacuum for 3 h before use. A solution of (−)-49 (97.7 mg, 0.0917 mmol) in THF (700 μL) was cooled to −78° C. and treated with NaHMDS (1.0 M in THF, 85.5 μL, 0.0855 mmol). The mixture was stirred for 20 min at 0° C., recooled to −78° C. and aldehyde C (28.0 mg, 0.0570 mmol) in THF (300 μL) was added. After 10 min at −78° C. and 2 h at room temperature, the mixture was quenched with saturated aqueous $NH_4Cl$ (1.0 mL) and extracted with ether (30 mL). The ether solution was washed with water, brine (30 mL each), dried over $MgSO_4$, filtered and concentrated. Flash chromatography (2% ethyl acetate/hexane) provided (−)-56 (50.0 mg, 76% yield) as a colorless oil: $[\alpha]^{23}_D$ −44.9° (c 2.09, $CHCl_3$); IR ($CHCl_3$) 2960 (s), 2930 (s), 2855 (s), 1615 (m), 1587 (w), 1517 (m), 1463 (s), 1380 (m), 1360 (m), 1320 (m), 1300 (m), 1250 (s), 1170 (m), 1160 (m), 1120–1000 (s, br), 990 (m), 965 (m), 935 (m), 900 (m), 835 (s), 807 (m), 670 (m) cm$^{-1}$; $^1$H NMR (500 MHZ, $CDCl_3$) d 7.35 (d, J=8.7 Hz, 2H), 6.85 (d, J=8.8 Hz, 2H), 5.37 (s, 1H), 5.27 (dd, J=11.2, 7.8 Hz, 1H), 5.19 (apparent t, J=10.9 Hz, 1H), 5.08 (d, J=10.1 Hz, 1H), 5.06 (d, J=2.2 Hz, 1H), 4.68 (apparent t, J=9.1 Hz, 1H), 4.08 (dd, J=11.2, 4.7 Hz, 1H), 3.78 (s, 3H), 3.68 (apparent t, J=10.1 Hz, 1H), 3.61 (dd, J=7.1, 1.7 Hz, 1H), 3.53 (apparent t, J=2.6 Hz, 1H), 3.50 (dd, J=9.9, 1.6 Hz, 1H), 3.46 (apparent t, J=11.1 Hz, 1H), 3.25 (apparent t, J=5.3 Hz, 1H), 2.71–2.58 (m, 1H), 2.68 (dq, J=12.8, 7.4 Hz, 1H), 2.62 (dq, J=12.8, 7.4 Hz, 1H), 2.50 (m, 1H), 2.30 (apparent t, J=12.2 Hz, 1H), 2.08–2.01 (m, 1H), 1.98–1.90 (m, 1H), 1.88 (dqd, J=7.1, 7.1, 1.7 Hz, 1H), 1.82 (apparent qt, J=7.1, 2.6 Hz, 1H), 1.65 (br d, J=12.4 Hz, 1H), 1.62–1.57 (m, 2H), 1.56 (d, J=0.4 Hz, 3H), 1.38 (ddd, J=13.6, 10.7, 1.5 Hz, 1H), 1.29–1.22 (apparent t, J=7.4 Hz, 3H), 1.00 (d, J=7.1 Hz, 3H), 0.94 (d, J=7.3 Hz, 3H), 0.930 (d, J=6.9 Hz, 3H), 0.925 (d, J=7.1 Hz, 3H), 0.90 (s, 18H), 0.89 (s, 9H), 0.86 (s, 9H), 0.74 (apparent d, J=6.6 Hz, 6H), 0.73 (d, J=6.1 Hz, 3H), 0.05 (s, 3H), 0.04 (s, 3H), 0.03 (s, 3H), 0.019 (s, 3H), 0.017 (s, 3H), 0.013 (s, 3H), 0.009 (s, 3H), 0.00 (s, 3H); $^{13}$C NMR (125 MHZ, $CDCl_3$) d 159.8, 134.4, 131.9, 131.8, 131.5, 131.4, 127.3, 113.4, 101.0, 83.4, 80.9, 80.4, 78.5, 76.7, 76.5, 74.2, 73.3, 65.5, 55.2, 42.5, 41.9, 38.2, 37.5, 37.1, 35.4, 34.4, 33.8, 26.3, 26.2, 26.0, 25.9, 25.1, 23.2, 18.5, 18.4, 18.12, 18.08, 17.0, 16.6, 15.6, 14.4, 12.7, 12.1, 11.6, 10.9, −2.7, −3.5, −3.66, −3.69, −4.2, −4.5, −4.9, −5.0; high resolution mass spectrum (FAB, NBA) m/z 1171.7799 [(M+Na)$^+$; calcd for $C_{63}H_{120}O_8SSi_4Na$: 1171.7781].

EXAMPLE 44
Hydroxy Diene (−)-55

A solution of the olefin (−)-54 (49.8 mg, 0.0434 mmol) in $CH_2Cl_2$ (4.4 mL) was cooled to −78° C. and DIBAL (1.0 M in toluene, 430 μL, 0.430 mmol) was added over 5 min. After 10 min at −78° C. and 30 min at 0° C., the reaction was quenched with saturated aqueous Rochelle's salt (500 μL). The mixture was diluted with ether (60 mL), washed with saturated aqueous Rochelle salt, brine (30 mL each), dried over $MgSO_4$, filtered and concentrated. Flash chromatography (5% ethyl acetate/hexane) furnished (−)-57 (38.0 mg, 88% yield) as a colorless oil: $[\alpha]^{23}_D$ −32° (c 1.90, $CHCl_3$); IR ($CHCl_3$) 3500 (w, br), 2960 (s), 2935 (s), 2900 (m), 2885 (m), 2860 (s), 1610 (m), 1585 (w), 1510 (m), 1470 (m), 1460 (m), 1400 (m), 1375 (m), 1360 (m), 1300 (m), 1250 (s), 1170 (m), 1095 (m), 1080 (m), 1047 (s), 1000 (m), 960 (m), 950 (m), 933 (m), 835 (s), 805 (m), 665 (m) cm$^{-1}$; $^1$H NMR (500 MHZ, $CDCl_3$) d 7.24 (d, J=8.6 Hz, 2H), 6.85 (d, J=8.6 Hz, 2H), 5.27 (dd, J=11.4, 7.8 Hz, 1H), 5.20 (apparent t, J=10.3 Hz, 1H), 5.10 (d, J=10.0 Hz, 1H), 5.05 (d, J=2.2 Hz, 1H), 4.68 (apparent t, J=9.2 Hz, 1H), 4.49 (ABq, $J_{AB}$=10.4 Hz, $\Delta\delta_{AB}$=23.4 Hz, 2H), 3.78 (s, 3H), 3.73 (ddd, J=10.7, 4.0, 4.0 Hz, 1H), 3.68 (apparent t, J=10.4 Hz, 1H), 3.57 (ddd, J=10.6, 5.1, 5.1 Hz, 1H), 3.53 (dd, J=5.4, 3.4 Hz, 1H), 3.50 (apparent t, J=5.2 Hz, 1H), 3.35 (apparent t, J=5.5 Hz, 1H), 3.26 (apparent t, J=5.2 Hz, 1H), 2.68 (dq, J=12.8, 7.4 Hz, 1H), 2.61 (dq, J=12.8, 7.5 Hz, 1H), 2.71–2.58 (m, 2H), 2.51–2.44 (m, 1H), 2.22 (apparent t, J=12.4 Hz, 1H), 1.99–1.86 (m, 3H), 1.81 (apparent qt, J=7.1, 2.6 Hz, 1H), 1.72 (br d, J=12.7 Hz, 1H), 1.62–1.57 (m, 1H), 1.61 (s, 3H), 1.56–1.48 (m, 1H), 1.38 (ddd, J=13.5, 12.3, 1.4 Hz, 1H), 1.27 (apparent t, J=7.4 Hz, 3H), 1.03 (d, J=6.9 Hz, 3H), 1.02 (d, J=6.8 Hz, 3H), 0.95–0.92 (m, 9H), 0.93 (s, 9H), 0.90 (s, 9H), 0.89 (s, 9H), 0.86 (s, 9H), 0.74 (d, J=8.0 Hz, 3H), 0.73 (d, J=7.0 Hz, 3H), 0.08 (s, 6H), 0.05 (s, 3H), 0.024 (s, 3H), 0.020 (s, 3H), 0.012 (s, 3H), 0.009 (s, 3H), 0.006 (s, 3H); $^{13}$C NMR (125 MHZ, $CDCl_3$) d 159.4, 134.4, 132.3, 131.7, 130.9, 130.4, 129.3, 114.0, 86.3, 80.9, 80.4, 77.6, 76.5, 75.3, 74.2, 65.6, 65.5, 55.3, 42.6, 41.9, 40.0, 37.6, 37.0, 36.8, 35.9, 35.2, 34.5, 26.30, 26.27, 25.9, 25.8, 25.1, 23.2, 18.53, 18.47, 18.13, 18.07, 17.1, 16.6, 15.7, 15.6, 14.4, 13.6, 11.6, 11.4, −2.8, −3.2, −3.4, −3.6, −4.2, −4.5, −4.9; high resolution mass spectrum (FAB, NBA) m/z 1173.7859 [(M+Na)$^+$; calcd for $C_{63}H_{122}O_8SSi_4Na$: 1173.7835].

EXAMPLE 45
Aldehyde (−)-56

A solution of alcohol (−)-55 (13.8 mg, 0.0120 mmol) and $Et_3N$ (42 μL, 0.30 mmol) in $CH_2Cl_2$ (200 μL) was cooled to 0° C. and treated with $SO_3$·pyridine (40 mg, 0.251 mmol) in DMSO (600 μL). After 45 min at 0° C., the mixture was diluted with ethyl acetate (30 mL), washed with aqueous $NaHSO_4$ (1.0 M, 30 mL), brine (2×30 mL), dried over $MgSO_4$, filtered and concentrated. Pipette flash chromatography (3% ethyl acetate/hexane) afforded (−)-56 (13.2 mg, 96% yield) as a colorless oil: $[\alpha]^{23}_D$ −32.1° (c 1.40, $CHCl_3$); IR ($CHCl_3$) 2960 (s), 2935 (s), 2880 (m), 1720 (m), 1610 (m), 1512 (m), 1470 (m), 1460 (m), 1387 (m), 1380 (m), 1360 (m), 1340 (m), 1320 (m), 1300 (m), 1250 (s), 1110 (s), 1098 (s), 1080 (s), 1048 (s), 1002 (m), 988 (m), 965 (m), 950 (m), 935 (m), 835 (s) cm$^{-1}$; $^1$H NMR (500 MHZ, $CDCl_3$) d 9.78 (d, J=2.5 Hz, 1H), 7.20 (d, J=8.6 Hz, 2H), 6.85 (d, J=8.7 Hz, 2H), 5.27 (dd, J=11.1, 7.8 Hz, 1H), 5.19 (apparent t, J=10.4 Hz, 1H), 5.10 (d, J=10.0 Hz, 1H), 5.05 (d, J=2.1 Hz, 1H), 4.67 (apparent t, J=8.9 Hz, 1H), 4.45 (apparent s, 2H), 3.78 (s, 3H), 3.68 (apparent t, J=10.2 Hz, 1H), 3.58–3.56 (m, 2H), 3.51 (apparent t, J=2.6 Hz, 1H), 3.25 (apparent t, J=5.2 Hz, 1H), 2.73 (dqd, J=7.1, 6.0, 2.6 Hz, 1H), 2.70–2.57 (m, 3H), 2.51–2.44 (m, 1H), 2.23 (apparent t, J=12.4 Hz, 1H), 1.98–1.85 (m, 2H), 1.81 (apparent qt, J=7.1, 2.6 Hz, 1H), 1.67 (br d, J=13.0 Hz, 1H), 1.60 (s, 3H), 1.62–1.50 (m, 2H), 1.37 (ddd, J=13.8, 10.4, 1.5 Hz, 1H), 1.26 (apparent t, J=7.4 Hz, 3H), 1.10 (d, J=7.0 Hz, 3H), 1.02 (d, J=7.0 Hz, 3H), 0.938 (d, J=7.1 Hz, 3H), 0.932 (d, J=7.8 Hz, 3H), 0.919 (s, 9H), 0.918 (d, J=6.6 Hz, 3H), 0.90 (s, 9H), 0.88 (s, 9H), 0.86 (s, 9H), 0.732 (d, J=6.7 Hz, 3H), 0.726 (d, J=6.8 Hz, 3H), 0.07 (s, 3H), 0.053 (s, 3H), 0.047 (s, 3H), 0.02 (s, 6H), 0.009 (s, 3H), 0.005 (s, 6H); $^{13}$C NMR (125 MHZ, $CDCl_3$) d 204.6, 159.3, 134.4, 132.3, 131.8, 130.8, 130.3, 129.1, 128.3, 113.8, 82.6, 80.9, 80.4, 76.5, 74.5, 74.2, 65.5, 55.3, 49.5, 42.5, 41.9, 40.3, 37.1, 36.8, 35.4, 34.9, 34.4, 26.3, 26.2, 25.9, 25.8, 25.1, 23.2, 18.49, 18.45, 18.12, 18.07, 17.0, 16.6, 15.6, 14.4, 13.3, 12.1, 11.6, 11.4, −2.8, −3.3, −3.4, −3.7, −4.2, −4.5, −4.9, −5.0; high resolution mass spectrum (FAB, NBA) m/z 1171.7670 [(M+Na)$^+$; calcd for $C_{63}H_{120}O_8SSiNa$: 1171.7676].

EXAMPLE 46
Tetraene (−)-57

A solution of $Ph_2PCH_2CH=CH_2$ (40 μL, 0.19 mmol) in THF (1.0 mL) was cooled to −78° C. and t-BuLi (1.7 M in pentane, 72.0 μL, 0.122 mmol) was added. The mixture was stirred at 0° C. for 30 min, recooled to −78° C. and treated with $Ti(OiPr)_4$ (45 μL, 0.15 mmol). After 30 min, a cold (−78° C.) solution of the aldehyde (−)-56 (30.2 mg, 0.0262 mmol) in THF (1.0 mL) was introduced via cannula, and the resultant mixture was stirred for 10 min at −78° C. and 1 h at 0° C. MeI (20 μL, 0.32 mmol) was then added, and the reaction was maintained at 0° C. for 30 min, warmed to room temperature, protected from light with aluminum foil, and stirred overnight. The reaction mixture was diluted with ether (30 mL), washed with aqueous $NaHSO_4$ (1.0 M), brine (30 mL each), dried over $MgSO_4$, filtered and concentrated. Flash chromatography (2% ethyl acetate/hexane) gave a 16:1 mixture of Z/E isomers (20.0 mg, 70% yield) as an oil. Pipette flash chromatography (20% benzene/hexane) furnished the Z-olefin (−)-57 as a colorless oil: $[\alpha]^{23}_D$ −57.2° (c 2.56, $CHCl_3$); IR ($CHCl_3$) 3015 (m), 2960 (s), 2940 (s), 2900 (m), 2885 (m), 2860 (s), 1613 (w), 1515 (m), 1475 (m), 1465 (m), 1390 (w), 1380 (w), 1360 (w), 1250 (s), 1110 (m), 1100 (m), 1080 (m), 1050 (s), 1003 (m), 963 (w), 950 (w), 835 (s), 800 (m), 790 (m), 770 (m), 700 (w), 690 (w), 670 (w), 655 (w) cm$^{-1}$; $^1$H NMR (500 MHZ, $CDCl_3$) d 7.25 (d, J=8.2 Hz, 2H), 6.84 (d, J=8.7 Hz, 2H), 6.57 (dddd, J=16.8, 11.0, 11.0, 0.7 Hz, 1H), 6.00 (apparent t, J=11.1 Hz, 1H), 5.55 (apparent t, J=10.5 Hz, 1H), 5.26 (dd, J=11.2, 7.8 Hz, 1H), 5.20–5.16 (m, 2H), 5.09 (d, J=10.1 Hz, 1H), 5.05 (d, J=2.2 Hz, 1H), 5.03 (d, J=10.0 Hz, 1H), 4.67 (apparent t, J=9.1 Hz, 1H), 4.49 (ABq, $J_{AB}$=10.6 Hz, $\Delta\delta_{AB}$=41.3 Hz, 2H), 3.78 (s, 3H), 3.68 (apparent t, J=10.2 Hz, 1H), 3.52 (apparent t, J=2.6 Hz, 1H), 3.43 (dd, J=4.8, 3.9 Hz, 1H), 3.24–3.21 (m, 2H), 3.01–2.94 (m, 1H), 2.67 (dq, J=12.8, 7.4 Hz, 1H), 2.61 (dq, J=12.8, 7.5 Hz, 1H), 2.71–2.57 (m, 1H), 2.46–2.39 (m, 1H), 2.00 (apparent t, J=12.4 Hz, 1H), 1.83–1.73 (m, 3H), 1.64 (br d, J=14.0 Hz, 1H), 1.62–1.52 (m, 2H), 1.55 (d, J=0.5 Hz, 3H), 1.36 (ddd, J 13.7, 10.8, 1.5 Hz, 1H), 1.26 (d, J=7.4 Hz, 3H), 1.25 (d, J=7.4 Hz, 3H), 1.08 (d, J=6.8 Hz, 3H), 0.98 (d, J=6.8 Hz, 3H), 0.94 (d, J=7.1 Hz, 3H), 0.93 (s, 9H), 0.90 (s, 9H), 0.89 (s, 9H), 0.89–0.86 (m, 3H), 0.86 (s, 9H), 0.73 (d, J=6.8 Hz, 3H), 0.70 (d, J=6.7 Hz, 3H), 0.08 (s, 6H), 0.05 (s, 3H), 0.02 (s, 3H), 0.013 (s, 3H), 0.010 (s, 6H), −0.02 (s, 3H); $^{13}$C NMR (125 MHZ, CDCl$_3$) d 159.1, 134.5, 134.3, 132.2, 131.9, 131.8, 131.2, 129.13, 129.07, 117.6, 113.7, 84.6, 80.9, 80.5, 76.5, 75.0, 74.2, 65.5, 55.3, 42.5, 41.9, 40.2, 37.2, 36.1, 35.4, 35.3, 34.5, 29.7, 26.3, 26.0, 25.9, 25.1, 23.1, 18.7, 18.6, 18.5, 18.14, 18.09, 17.0, 16.8, 15.6, 14.8, 14.4, 11.6, 10.6, −2.8, −3.2, −3.3, −3.6, −4.2, −4.5, −4.90, −4.93; high resolution mass spectrum (FAB, NBA) m/z 1195.8001 [(M+Na)$^+$; calcd for C$_{66}$H$_{124}$O$_7$SSi$_4$Na: 1195.8042].

EXAMPLE 47

Lactone (−)-58

A solution of diene (−)-57 (7.0 mg, 0.00597 mmol) in THF/CH$_3$CN (2:1, 1.50 mL) was treated with pH 7.0 phosphate buffer (500 μL) and HgCl$_2$ (215 mg). The suspension was stirred at room temperature for 40 min, diluted with ether (30 mL), washed with brine (2×30 mL), dried over MgSO$_4$, filtered and concentrated. Pipette flash chromatography (5% ethyl acetate/hexane) provided a mixture of lactols as a colorless oil which was further treated with DMSO (1.0 mL) and Ac$_2$O (200 mL) at room temperature for 2 days. The mixture was diluted with ether (30 mL), washed with saturated NaHCO$_3$ (30 mL), brine (30 mL), dried over MgSO$_4$, filtered and concentrated. Pipette flash chromatography (2% ethyl acetate/hexane) provided (−)-58 (5.5 mg, 82% yield from (−)-57) as a colorless oil: $[\alpha]^{23}_D$ −31.6 (c 0.23, CHCl$_3$); IR (CHCl$_3$) 3015 (m), 2960 (s), 2930 (s), 2880 (m), 2855 (m), 1725 (m), 1610 (w), 1510 (w), 1460 (m), 1385 (m), 1373 (m), 1360 (m), 1300 (w), 1250 (s), 1230 (m), 1200 (m), 1170 (m), 1120 (m), 1097 (m), 1060 (m), 1045 (s), 1020 (m), 1003 (m), 980 (w), 955 (w), 930 (w), 905 (w), 867 (m), 835 (s), 800 (m), 695 (m), 670 (m), 660 (m) cm$^{-1}$; $^1$H NMR (500 MHZ, CDCl$_3$) d 7.25 (d, J=9.0 Hz, 2H), 6.84 (d, J=8.7 Hz, 2H), 6.57 (ddd, J=16.7, 10.6, 10.6 Hz, 1H), 6.00 (apparent t, J=11.0 Hz, 1H), 5.55 (apparent t, J=10.5 Hz, 1H), 5.26 (dd, J=11.1, 7.9 Hz, 1H), 5.19 (dd, J=15.4, 1.4 Hz, 1H), 5.18 (apparent t J=10.1 Hz, 1H), 5.10 (d, J=10.2 Hz, 1H), 5.01 (d, J=10.0 Hz, 1H), 4.75 (apparent t, J=9.2 Hz, 1H), 4.50 (ddd, J=10.5, 1.3, 1.3 Hz, 1H), 4.50 (ABq, J$_{AB}$=10.6 Hz, Δδ$_{AB}$=42.6 Hz, 2H), 3.78 (s, 3H), 3.60 (apparent t, J=2.4 Hz, 1H), 3.42 (dd, J=5.1, 3.7 Hz, 1H), 3.23 (dd, J=7.5, 3.7 Hz, 1H), 3.20 (apparent t, J=5.4 Hz, 1H), 3.01–2.94 (m, 1H), 2.60 (qd, J=7.7, 2.6 Hz, 1H), 2.62–2.55 (m, 1H), 2.45–2.38 (m, 1H), 1.98 (apparent t, J=12.3 Hz, 1H), 1.84–1.67 (m, 3H), 1.63 (br d, J=13.2 Hz, 1H), 1.52 (s, 3H), 1.55–1.48 (m, 1H), 1.20 (d, J=7.6 Hz, 3H), 1.09 (d, J=6.8 Hz, 3H), 0.98 (d, J=6.8 Hz, 3H), 0.93 (apparent d, J=6.7 Hz, 6H), 0.93 (s, 9H), 0.89 (s, 9H), 0.86 (s, 9H), 0.85 (s, 9H), 0.84 (d, J=6.8 Hz, 3H), 0.69 (d, J=6.7 Hz, 3H), 0.085 (s, 3H), 0.079 (s, 3H), 0.051 (s, 3H), 0.046 (s, 3H), 0.042 (s, 3H), 0.029 (s, 3H), 0.028 (s, 3H), −0.02 (s, 3H); $^{13}$C NMR (125 MHZ, CDCl$_3$) d 173.2, 159.1, 134.4, 133.4, 132.4, 132.2, 131.9., 131.3, 131.2, 129.11, 129.09, 117.6, 113.7, 84.6, 80.5, 76.9, 75.0, 74.9, 64.6, 55.3, 44.1, 42.7, 40.1, 37.5, 36.0, 35.44, 35.37, 35.2, 34.2, 26.31, 26.28, 25.9, 25.7, 23.0, 18.7, 18.6, 18.4, 18.1, 18.0, 17.1, 16.5, 16.4, 14.9, 14.1, 10.5, −3.0, −3.2, −3.3, −4.3, −4.4, −4.5, −4.8, −4.9; high resolution mass spectrum (FAB, NBA) m/z 1149.7836 [(M+Na)$^+$; Calcd for C$_{64}$H$_{118}$O$_8$Si$_4$Na: 1149.7802].

EXAMPLE 48

Alcohol (−)-59

A solution of (−)-58 (4.0 mg, 0.00355 mmol) in CH$_2$Cl$_2$ (500 μL) was treated with H$_2$O (50 μL) and DDQ (3.0 mg, 0.0132 mmol) at 0° C. After 1 h, the mixture was diluted with ethyl acetate (30 mL), washed with brine (3×30 mL), dried over MgSO$_4$, filtered and concentrated. Pipette flash chromatography (2% ethyl acetate/hexane) provided (−)-59 (3.4 mg, 95% yield) as a colorless oil: $[\alpha]^{23}_D$ −20° (c 0.34, CHCl$_3$); IR (film, CHCl$_3$ on NaCl plate) 3500 (w, br), 2960 (s), 2930 (s), 2890 (s), 2855 (s), 1740 (m), 1460 (m), 1405 (m), 1380 (m), 1360 (s), 1253 (m), 1220 (m), 1120 (s), 1093 (s), 1075 (s), 1045 (s), 1022 (s), 1002 (m), 980 (m), 933 (m), 902 (m), 833 (s), 808 (m), 770 (s), 663 (m) cm$^{-1}$; $^1$H NMR (500 MHZ, CDCl$_3$) d 6.61 (ddd, J=16.8, 10.9, 10.9 Hz, 1H), 6.13 (apparent t, J=11.0 Hz, 1H), 5.32 (apparent t, J=10.5 Hz, 1H), 5.28 (dd, J=11.1, 7.9 Hz, 1H), 5.24–5.21 (m, 1H), 5.19 (apparent t, J=10.3 Hz, 1H), 5.14 (d, J=10.2 Hz, 1H), 5.06 (d, J=10.0 Hz, 1H), 4.76 (apparent t, J=9.3 Hz, 1H), 4.50 (apparent t, J=9.9 Hz, 1H), 3.62 (apparent t, J=2.4 Hz, 1H), 3.60 (dd, J=5.5, 3.4 Hz, 1H), 3.32 (br d, J=5.3 Hz, 1H), 3.24 (apparent t, J=5.1 Hz, 1H), 2.79 (ddq, J=9.9, 6.7, 6.7 Hz, 1H), 2.60 (qd, J=7.6, 2.7 Hz, 1H), 2.63–2.57 (m, 1H), 2.50–2.45 (m, 1H), 2.16 (apparent t, J=12.3 Hz, 1H), 1.90–1.77 (m, 3H), 1.75–1.69 (m, 2H), 1.57 (s, 3H), 1.60–1.50 (m, 1H), 1.20 (d, J=7.6 Hz, 3H), 0.96 (d, J=6.8 Hz, 3H), 0.95 (d, J=6.6 Hz, 3H), 0.95–0.93 (m, 6H), 0.91 (s, 9H), 0.89 (s, 9H), 0.89–0.84 (m, 3H), 0.87 (s, 9H), 0.85 (s, 9H), 0.73 (d, J=6.8 Hz, 3H), 0.07 (apparent s, 6H), 0.052 (s, 3H), 0.051 (s, 3H), 0.04 (apparent s, 6H), 0.03 (s, 3H), −0.01 (s, 3H); $^{13}$C NMR (125 MHZ, CDCl$_3$) d 173.3, 134.7, 133.5, 132.5, 132.1, 132.0, 131.5, 131.0, 118.4, 80.5, 78.8, 76.4, 74.9, 64.7, 44.1, 42.7, 38.0, 37.4, 36.3, 36.1, 35.2, 35.1, 34.2, 26.3, 26.2, 25.9, 25.7, 23.2, 18.5, 18.1, 18.0, 17.3, 17.2, 16.4, 16.1, 14.1, 13.7, 9.4, −3.0, −3.3, −3.6, −4.34, −4.36, −4.5, −4.8; high resolution mass spectrum (FAB, NBA) m/z 1029.7273 [(M+Na)$^+$; calcd for C$_{56}$H$_{110}$O$_7$Si$_4$Na: 1029.7226].

EXAMPLE 49

Carbamate (−)-60

A solution of alcohol (−)-59 (2.2 mg, 0.00219 mmol) in CH$_2$Cl$_2$ (500 μL) was treated with Cl$_3$CON═C═O (20 μL, 0.168 mmol) at room temperature. After 30 min, the mixture was diluted with regular CH$_2$Cl$_2$ (2.0 mL) and treated with neutral Al$_2$O$_3$ (500 mg). The mixture was stirred at room temperature for 2 h, filtered through a short silica plug, and concentrated. Pipette flash chromatography (10% ethyl acetate/hexane) provided (−)-60 (1.9 mg, 83% yield) as a colorless oil: $[\alpha]^{23}_D$ −37° (c 0.19, CHCl$_3$); IR (film, CHCl$_3$ on NaCl plate) 3510 (m), 3360 (m, br), 3180 (m), 2960 (s), 2930 (s), 2880 (s), 2855 (s), 1730 (s, br), 1596 (m), 1460 (s), 1385 (s), 1362 (s), 1325 (m), 1255 (s), 1220 (m), 1100 (s), 1043 (s), 983 (m), 937 (m), 904 (m), 832 (s), 770 (s), 663 (m) cm$^{-1}$; $^1$H NMR (500 MHZ, CDCl$_3$) d 6.58 (dddd, J=16.8, 10.6, 10.6, 0.7 Hz, 1H), 6.01 (apparent t, J=11.0 Hz, 1H), 5.36 (apparent t, J=10.4 Hz, 1H), 5.27 (dd, J=11.1, 7.9 Hz, 1H), 5.22–5.16 (m, 2H), 5.12 (d, J=10.1 Hz, 1H), 5.03 (d, J=10.0 Hz, 1H), 4.76 (apparent t, J=9.2 Hz, 1H), 4.71 (apparent t, J=6.1 Hz, 1H), 4.50 (ddd, J=10.5, 10.5, 1.3 Hz, 1H), 4.44 (br s, 2H), 3.62 (apparent t, J=2.4 Hz, 1H), 3.42 (apparent t, J=4.5 Hz, 1H), 3.22 (apparent t, J=5.3 Hz, 1H), 2.98 (ddq, J=10.1, 6.6, 6.6 Hz, 1H), 2.60 (qd, J=7.6, 2.7 Hz, 1H), 2.63–2.55 (m, 1H), 2.48–2.41 (m, 1H), 2.09 (apparent t, J=12.4 Hz, 1H), 1.93–1.88 (m, 1H), 1.87–1.77 (m, 2H), 1.71 (ddd, J=14.1, 10.8, 1.6 Hz, 1H), 1.67 (br d, J=13.7 Hz, 1H), 1.56 (apparent s, 3H), 1.55–1.50 (m, 1H), 1.21 (d, J=7.6 Hz, 3H), 0.98 (d, J=6.8 Hz, 3H), 0.95 (d, J=7.0 Hz, 3H), 0.94 (d, J=7.5 Hz, 3H), 0.918 (d, J=6.8 Hz, 3H), 0.915 (s, 9H), 0.89 (s, 9H), 0.86 (s, 9H), 0.853 (d, J=6.4 Hz, 3H), 0.847 (s, 9H), 0.70 (d, J=6.8 Hz, 3H), 0.09 (s, 3H), 0.07 (s, 3H), 0.053 (s, 3H), 0.051 (s, 3H), 0.040 (s, 3H), 0.037 (s, 3H), 0.03 (s, 3H), −0.02 (s, 3H); $^{13}$C NMR (125 MHZ, CDCl$_3$) d 173.3, 156.9, 133.6, 133.5, 132.4, 132.1, 131.9, 131.4, 129.8, 118.0, 80.5, 78.9, 74.9, 64.6, 44.2, 42.7, 37.8, 37.4, 36.0, 35.3, 35.2, 34.5, 34.2, 26.3, 26.2, 25.9, 25.7, 23.0, 18.5, 18.4, 18.1, 18.0, 17.5, 17.1, 16.44, 16.38, 14.1, 13.7, 10.1, −3.0, −3.4, −3.6, −4.4, −4.5, −4.8; high resolution mass spectrum (FAB, NBA) m/z 1072.7264 [(M+Na)$^+$; calcd for $C_{57}H_{111}NO_8Si_4Na$: 1072.7283].

EXAMPLE 50

Discodermolide [(−)-1]

A solution of olefin (−)-60 (5.8 mg, 5.5 mmol) in 4806 HF—CH$_3$CN (1:9, 1.0 mL) was stirred at room temperature for 12 h, then quenched with saturated aqueous NaHCO$_3$ (5.0 mL). The mixture was extracted with ethyl acetate (3×10 mL). The combined organic extracts were washed with brine (5.0 mL), dried over MgSO$_4$, filtered and concentrated. Pipette flash chromatography (gradient elution, 1:30 to 1:6 MeOH/CHCl$_3$) provided (−)-1 (2.0 mg, 60% yield) as a white amorphous solid: [α]$^{23}_D$ −16° (c 0.03, MeOH); IR (CHCl$_3$) 3690 (w), 3620 (w), 3540 (w), 3430 (w), 3020 (s), 2975 (m), 2935 (m), 1740 (m), 1590 (w), 1540 (w), 1520 (w), 1467 (w), 1430 (w), 1385 (m), 1330 (w), 1233 (s), 1210 (s), 1100 (w), 1045 (m), 1033 (m), 975 (w), 930 (m), 910 (w), 793 (m), 777 (m), 765 (m), 750 (m), 705 (m), 687 (m), 670 (m), 660 (m), 625 (w) cm$^{-1}$; $^1$H NMR (500 MHZ, CDCl$_3$) d 6.60 (dddd, J=16.8, 8.4, 8.4, 0.8 Hz, 1H), 6.02 (apparent t, J=11.1 Hz, 1H), 5.51 (dd, J=11.2, 7.9 Hz, 1H), 5.42 (ddd, J=10.6, 10.6, 0.6 Hz, 1H), 5.34 (apparent t, J=10.4 Hz, 1H), 5.20 (dd, J=16.9, 1.9 Hz, 1H), 5.16 (d, J=10.0 Hz, 1H), 5.11 (d, J=10.1 Hz, 1H), 4.77–4.69 (m, 1H), 4.70 (dd, J=7.3, 4.2 Hz, 1H), 4.60 (ddd, J=10.0, 10.0, 2.4 Hz, 1H), 4.56 (br s, 2H), 3.73 (m, 1H), 3.28 (m, 1H), 3.18 (dd, J=6.8, 4.8 Hz, 1H), 2.98 (ddq, J=10.1, 6.9, 6.9 Hz, 1H), 2.78 (ddq, J=9.8, 6.8, 6.8 Hz, 1H), 2.66 (qd, J=7.3, 4.6 Hz, 1H), 2.60–2.55 (m, 1H), 2.10–1.80 (m, 10H), 1.69 (ddd, J=14.4, 10.3, 3.1 Hz, 1H), 1.64 (d, J=1.3 Hz, 3H), 1.30 (d, J=7.4 Hz, 3H), 1.06 (d, J=6.9 Hz, 3H), 1.00 (d, J=6.8 Hz, 3H), 0.99 (d, J=6.7 Hz, 3H), 0.97 (d, J=6.8 Hz, 3H), 0.94 (d, J=6.8 Hz, 3H), 0.82 (d, J=6.3 Hz, 3H); $^{13}$C NMR (125 MHZ, CDCl$_3$) d 173.6, 157.0, 134.4, 133.7, 133.4, 132.9, 132.2, 129.9, 129.8, 117.9, 79.1, 78.9, 77.9, 75.7, 73.2, 64.4, 43.1, 41.0, 37.4, 36.1, 36.0, 35.8, 35.3, 34.8, 33.1, 23.3, 18.4, 17.4, 15.6, 15.5, 13.7, 12.5, 9.0; high resolution mass spectrum (FAB, NBA) m/z 616.3840 [(M+Na)$^+$; calcd for $C_{33}H_{55}NO_8Na$: 616.3826].

EXAMPLE 51

Figure 16:
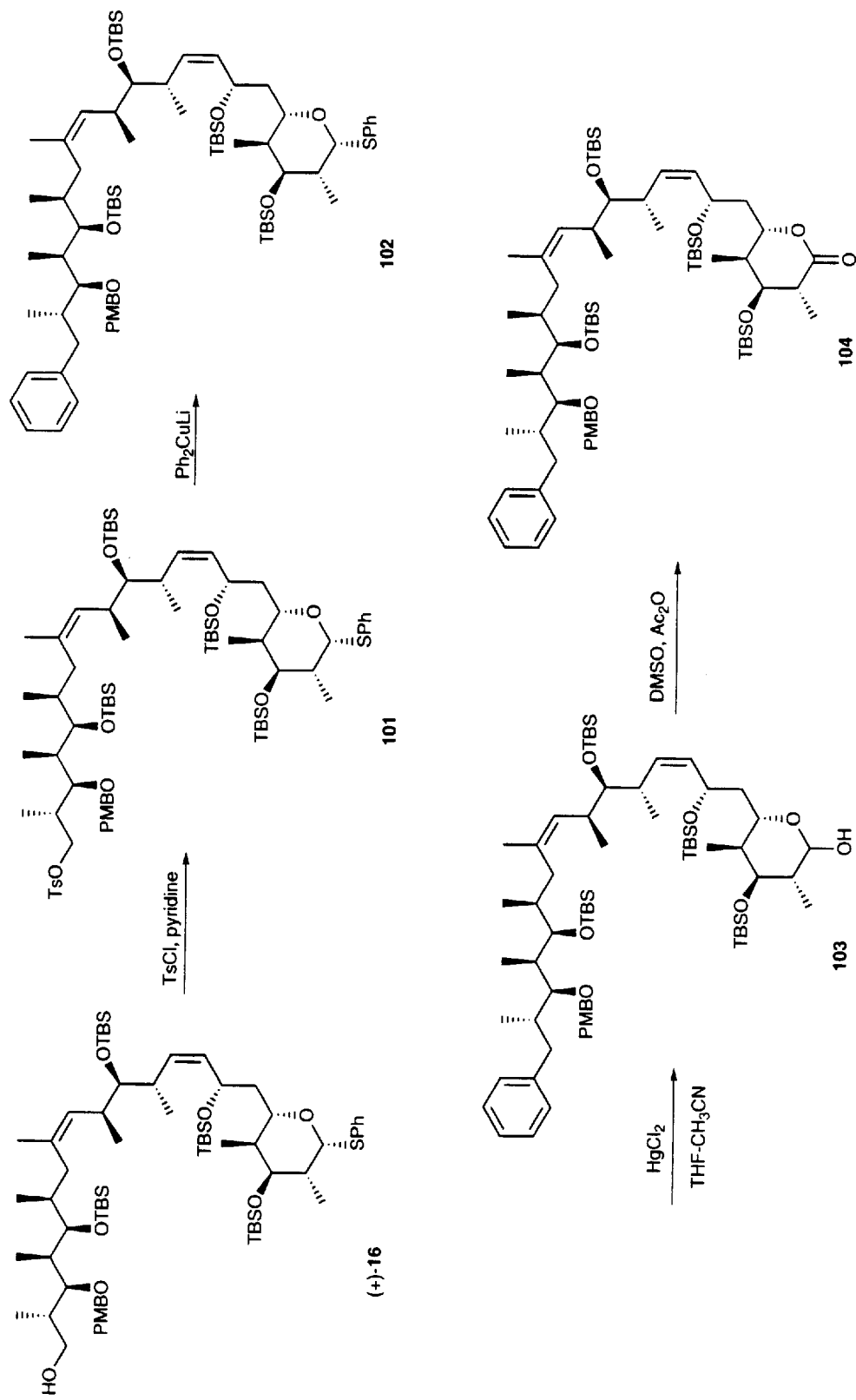
FIG. 16 shows a synthetic scheme for compound 104.
Figure 17:
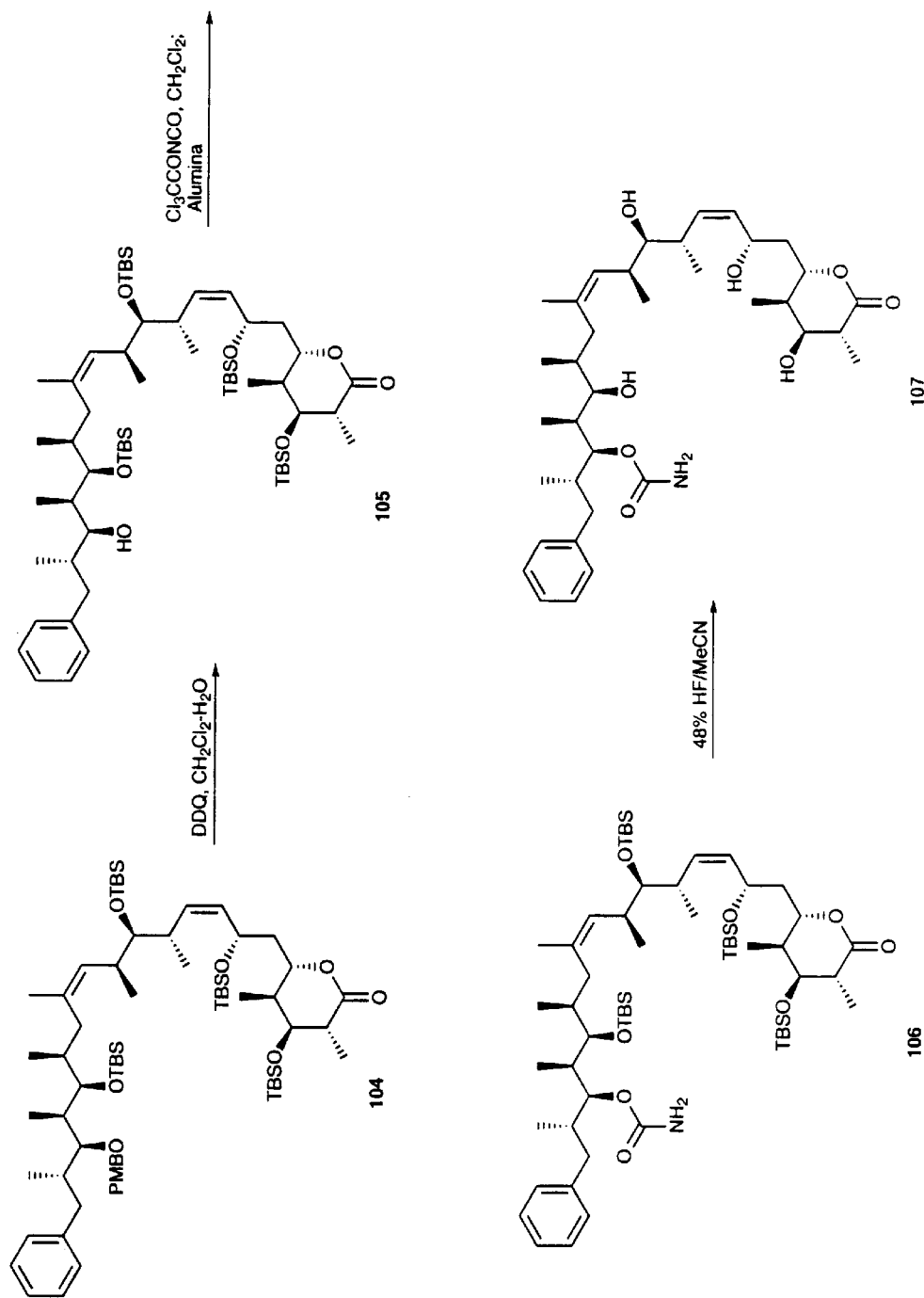
FIG. 17 shows a synthetic scheme for compound 107.
Figure 18:
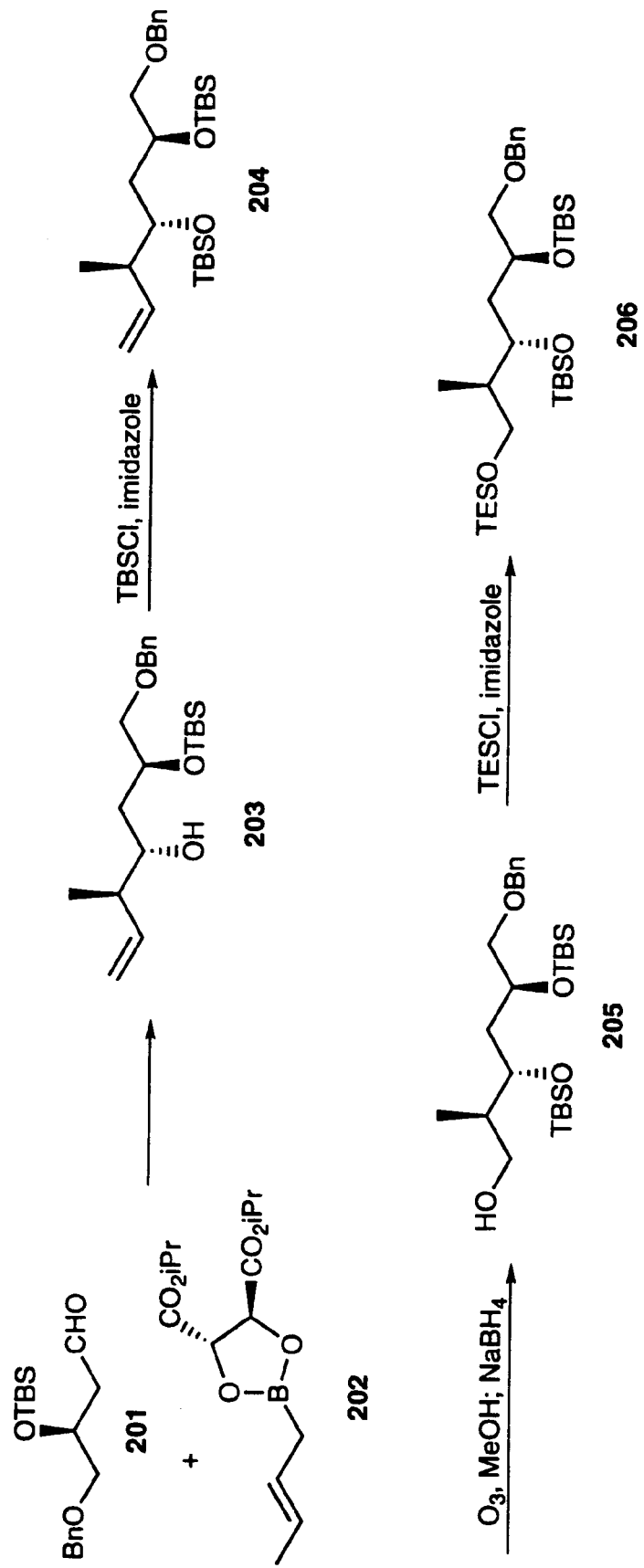
FIG. 18 shows a synthetic scheme for compound 206.
Figure 19:
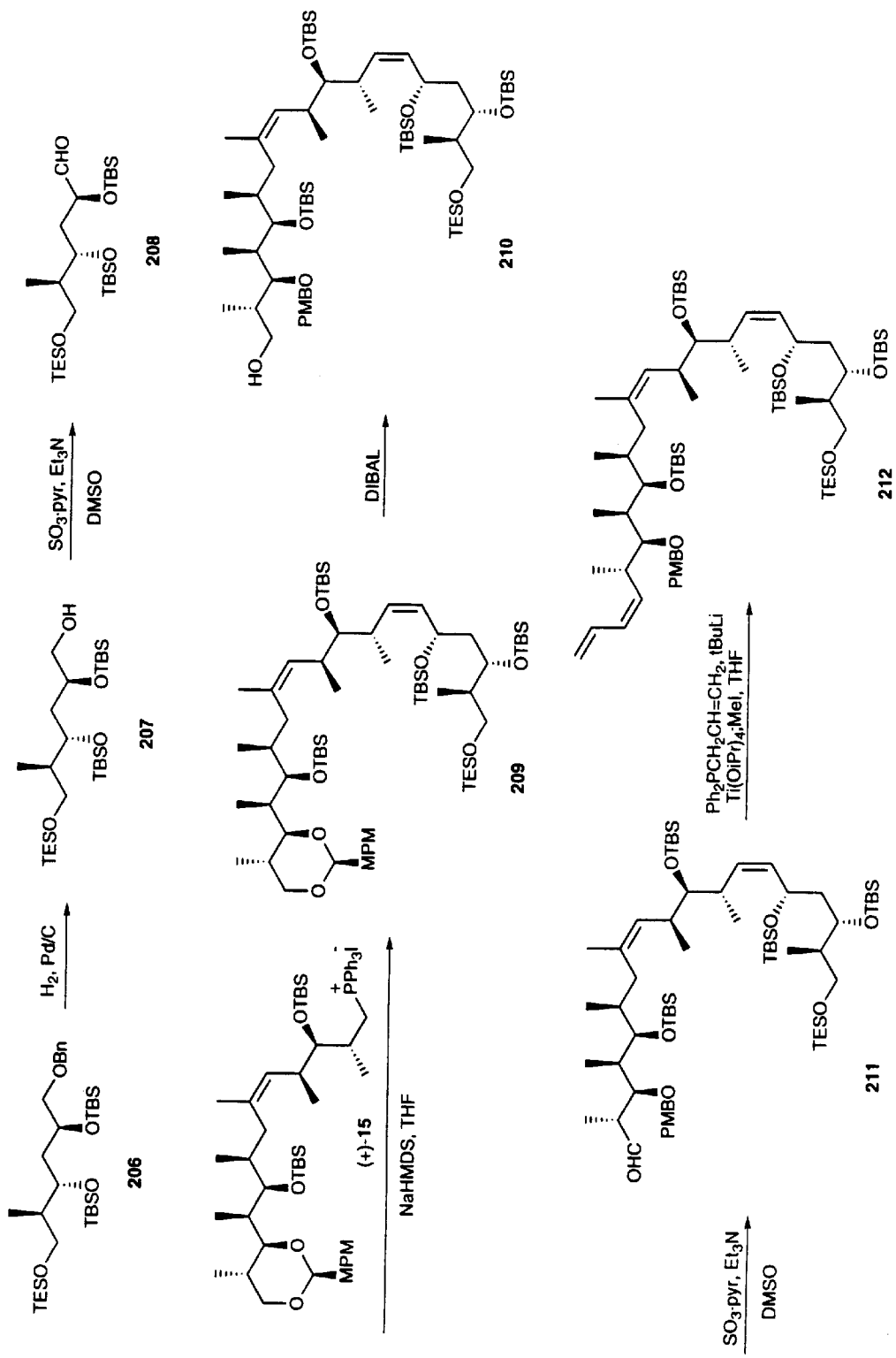
FIG. 19 shows a synthetic scheme for compound 212.
Figure 20:
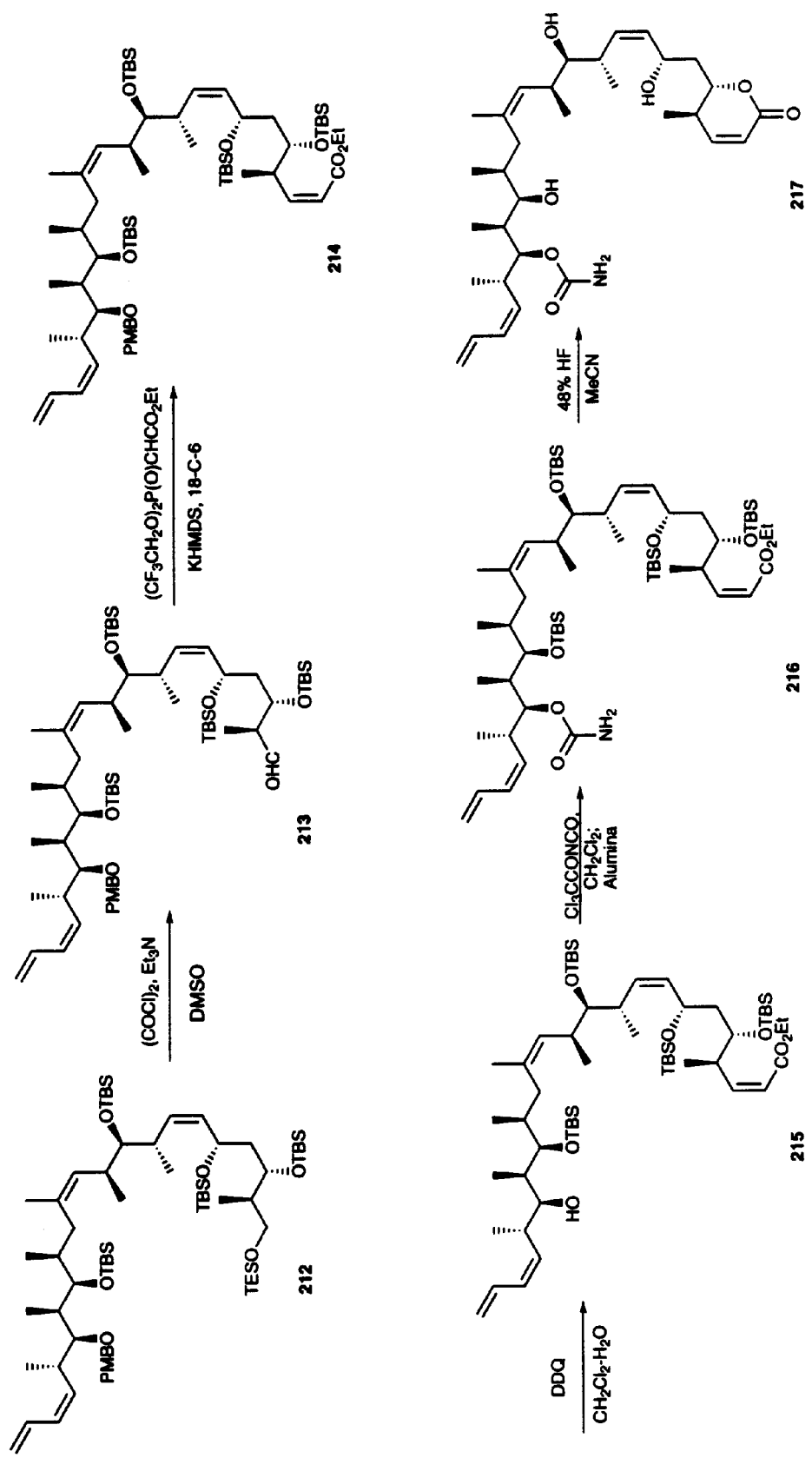
FIG. 20 shows a synthetic scheme for compound 217.

FIGS. 16 and 17

A. Tosylate 101

A solution of diene 16 (see, Smith, et al., *J. Am. Chem. Soc.* 1995, 117, 12011) (1.15 g, 1.0 mmol) in anhydrous pyridine (10 mL) at 0° C. is treated with p-toluenesulfonyl chloride (286 mg, 1.5 mmol). The mixture is allowed to warm to room temperature for 4–6 h. The pyridine is removed in vacuo and the residue is purified by flash chromatography to afford tosylate 101.

B. Arene 102

Phenyllithium (2.7 mL, 1.8 M in cyclohexane-ether (70:30)) is added dropwise to a solution of copper (I) iodide (460 mg, 2.4 mmol) in anhydrous diethyl ether (5 mL) at 0° C. To the resultant mixture is added a solution of tosylate 101 (780 mg, 0.6 mmol) in ether (5 mL) and the resultant mixture is warmed to room temperature with stirring. After 4 h, saturated aqueous ammonium chloride (20 mL) is added. The layers are separated and the aqueous layer is extracted with ethyl acetate. The combined organics are dried over magnesium sulfate and concentrated in vacuo. The residue is purified by flash chromatography to afford 102.

C. Lactol 103

To a solution of 102 (120 mg, 0.1 mmol) in tetrahydrofuran-acetonitrile (15 mL, 2:1) is added phosphate buffer (pH 7, 5 mL) and mercury (II) chloride (272 mg, 1.0 mmol). The resultant mixture is stirred 1 h at room temperature. The reaction mixture is diluted with ether (100 mL) and washed with saturated aqueous brine (2×50 mL), dried over magnesium sulfate and concentrated in vacuo. The residue is purified by flash chromatography to afford 103 as a mixture of α and β anomers.

D. Lactone 104

To a solution of 103 (84 mg, 0.070 mmol) in dimethyl sulfoxide (10 mL) is added acetic anhydride (2 mL). After 2 days at room temperature, the mixture is diluted with ether (100 mL) and washed with saturated aqueous sodium bicarbonate (50 mL), saturated aqueous brine (50 mL), dried over magnesium sulfate and concentrated in vacuo. The residue is purified by flash chromatography to afford 104.

E. Alcohol 105

To a solution of 104 (56 mg, 0.050 mmol) in dichloromethane (3 mL) at 0° C. is added water (50 mL) and 2,3-dichloro-5,6-dicyano-1,4-benzoquinone (52 mg, 0.018 mmol). After 1 h, the reaction mixture is diluted with ethyl acetate (50 mL), washed with saturated aqueous brine (3×25 mL), dried over magnesium sulfate and concentrated in vacuo. The residue is purified by flash chromatography to afford 105.

F. Carbamate 106

To a solution of 105 (10 mg, 0.010 mmol) in dichloromethane (2 mL) is added trichloroacetyl isocyanate (0.12 mL, 1.00 mmol). After 30 min, the reaction mixture is diluted with dichloromethane (4 mL) and neutral alumina (1 g) is added. The resultant suspension is stirred an additional 4 h. The reaction mixture is filtered and the concentrated filtrate is chromatographed on silica gel to afford 106.

G. Tetrol 107

A solution of 106 (10 mg, 0.0096 mmol) in 48% hydrofluoric acid-acetonitrile (1:9, 2 mL) is stirred at ambient temperature. After 12 h, saturated aqueous sodium bicarbonate (25 mL) is added and the mixture is extracted with ethyl acetate (3×20 mL). The combined organics are dried over magnesium sulfate and concentrated in vacuo. The residue is purified by flash chromatography to afford 107.

EXAMPLE 52

FIGS. 18–20

A. Alcohol 203

To a slurry of powdered 4-Å molecular sieves (2.0 g) in 100 mL of anhydrous toluene is added boronate 202 (see, Roush, et al., *J. Am. Chem. Soc.* 1990, 112, 6348) (170 mL, 1.0 M in toluene). The resultant solution is stirred 10 min at room temperature and then cooled to −78° C. A solution of aldehyde 201 (see, Solladie, et al., *Tetrahedron Lett.* 1987, 28, 797) (113 mmol) in toluene (100 mL) is added over a 2 h period, after which the reaction is maintained at −78° C. for 10 h. Excess ethanolic sodium borohydride (ca. 0.75 g/10 mL) is added and the reaction mixture is warmed to 0° C. Aqueous 1 N sodium hydroxide (300 mL) is added and the mixture is stirred vigorously for 2 h. The layers are separated and the aqueous layer is extracted with ether (5×300 mL). The combined organics are dried over potassium carbonate and concentrated in vacuo. The residue is purified by flash chromatography to afford 203.

B. Bis-silyl ether 204

A solution of 203 (75 mmol) in dimethylformamide (150 mL) is cooled to 0° C. and treated with imidazole (150 mmol) and tert-butyldimethylsilyl chloride (100 mmol). The resultant solution is warmed to room temperature. After 12 h, the reaction mixture is poured into 1500 mL of water and extracted with ether (3×200 mL). The ethereal extracts are washed with water (2×50 mL) and saturated aqueous brine (50 mL), dried over magnesium sulfate and concentrated in vacuo. The residue is purified by flash chromatography to afford 204.

C. Alcohol 205

A solution of 204 (20 mmol) in 500 mL of methanol is cooled to −78° C. and treated with a stream of ozone and oxygen until the colorless solution is converted into a steel blue one. The crude reaction mixture is cautiously quenched with sodium borohydride (100 mmol) and the resultant solution is warmed to room temperature. After 3 h, the excess sodium borohydride is destroyed by the cautious addition of water. The methanol is removed in vacuo and the residue is partitioned between saturated aqueous ammonium chloride (200 mL) and ethyl acetate (200 mL). The layers are separated and the aqueous layer is further extracted with ethyl acetate (2×100 mL). The combined organics are dried over anhydrous magnesium sulfate and concentrated in vacuo. The residue is purified by flash chromatography to afford 205.

D. Triethylsilyl ether 206

A solution of 205 (15 mmol) in dimethylformamide (30 mL) is cooled to 0° C. and treated with imidazole (30 mmol) and triethylsilyl chloride (20 mmol). The resultant solution is warmed to room temperature. After 12 h, the reaction mixture is poured into 300 mL of water and extracted with ether (3×40 mL). The ethereal extracts are washed with water (2×25 mL) and saturated aqueous brine (25 mL), dried over magnesium sulfate and concentrated in vacuo. The residue is purified by flash chromatography to afford 206.

E. Alcohol 207

To a solution of 206 (6 mmol) in ethyl acetate-ethanol (8:1, 90 mL) is added palladium on carbon (10% wet, 500 mg). The mixture is stirred under hydrogen atmosphere for 3–6 h, then filtered and concentrated in vacuo. The residue is purified by flash chromatography to afford 207.

F. Aldehyde 208

To a −10° C. solution of 207 (13 mmol) and triethylamine (50 mmol) in dichloromethane (26 mL) is added a solution of sulfur trioxide-pyridine (39 mmol) in dimethyl sulfoxide (50 mL). The mixture is stirred 1 h at room temperature and diluted with ether (150 mL). The organic phase is washed with aqueous sodium bisulfate (1 M, 100 mL), saturated aqueous brine (4×100 mL), dried over magnesium sulfate, and concentrated in vacuo. The residue is purified by flash chromatography to afford 208.

G. Wittig product 209

Phosphonium salt 15 (see, Smith, et al., *J. Am. Chem. Soc.* 1995, 117, 12011) (0.2 mmol) is dissolved in anhydrous tetrahydrofuran (2 mL) and chilled to 0° C. A solution of sodium bis(trimethylsilyl)amide (0.2 mmol, 1.0 M in tetrahydrofuran) is added and the reaction mixture is stirred 30 min at 0° C. After cooling to −78° C., a solution of aldehyde 208 (0.1 mmol) in tetrahydrofuran (2 mL) is added and the mixture is stirred 10 min at −78° C. and 2 h at room temperature. Saturated aqueous ammonium chloride (2 mL) is added and the resultant mixture is extracted with ether (3×20 mL). The ethereal layer is washed with water (2×25 mL) and saturated aqueous brine (25 mL), dried over magnesium sulfate and concentrated in vacuo. The residue is purified by flash chromatography to afford 209.

H. Hydroxy diene 210

A −78° C. solution of 209 (0.05 mmol) in $CH_2Cl_2$ (5 mL) is treated with diisobutylaluminum hydride (0.5 mL, 1.0 M in toluene). The resultant solution is stirred 10 min at −78° C. and 30 min at 0° C. The reaction is quenched with a saturated solution of sodium potassium tartrate (50 mL) and the mixture is diluted with ether (60 mL). The organic layer is separated, dried over magnesium sulfate, and concentrated in vacuo. The residue is purified by flash chromatography to afford 210.

I. Aldehyde 211

To a −10° C. solution of 207 (1.3 mmol) and triethylamine (5.0 mmol) in dichloromethane (3 mL) is added a solution of sulfur trioxide-pyridine (3.9 mmol) in dimethyl sulfoxide (5 mL). The mixture is stirred 1 h at room temperature and diluted with ether (15 mL). The organic phase is washed with aqueous sodium bisulfate (1 M, 10 mL), saturated aqueous brine (4×10 mL), dried over magnesium sulfate, and concentrated in vacuo. The residue is purified by flash chromatography to afford 211.

J. Tetraene 212

A solution of diphenylallylphosphine (0.08 mL, 0.38 mmol) in tetrahydrofuran (2 mL) is cooled to −78° C. and tert-butyllithium (0.14 mL, 1.7 M in pentane) is added. The mixture is warmed to 0° C. for 30 min, then recooled to −78° C. and treated with titanium (IV) isopropoxide (0.30 mmol). After 30 min, aldehyde 211 (0.30 mmol) is introduced as a solution in tetrahydrofuran (2 mL). The resultant solution is stirred at −78° C. for 15 min and at 0° C. for 1 h. Methyl iodide (0.64 mmol) is added, and the reaction is warmed to room temperature for 12 h. The reaction mixture is diluted with ether (60 mL), washed with aqueous sodium bisulfate (30 mL, 1.0 M), saturated aqueous brine (30 mL), and is dried over magnesium sulfate and concentrated in vacuo. The residue is purified by flash chromatography to afford 212.

K. Aldehyde 213

Oxalyl chloride (1.5 mmol) is added dropwise to a −78° C. solution of dimethyl sulfoxide (3 mmol) in dichloromethane (4 mL). After 15 min, a −78° C. solution of 212 (1 mmol) in dichloromethane (2 mL) is added via canula. After an additional 15 min, diisopropylethylamine (4.5 mmol) is added and the reaction is gradually warmed to room temperature over 1 h and quenched with aqueous sodium bisulfate. The mixture is diluted with ether (50 mL) and is washed with water (2×30 mL), saturated aqueous brine (2×30 mL), is dried over magnesium sulfate and concentrated in vacuo. The residue is purified by flash chromatography to afford 213.

L. Ester 214

To a −78° C. solution of $(F_3CCH_2O)_2POCH_2CO_2Et$ (2 mmol) and 18-crown-6 (2.4 mmol) in tetrahydrofuran (5 mL) is added potassium bis(trimethylsilyl)amide (2 mmol) in tetrahydrofuran (2 mL). The resultant solution is stirred 10 min at −78° C. and then treated with aldehyde 213 (1.2 mmol) in 4 mL of tetrahydrofuran. The reaction mixture is warmed to 0° C. for 6–8 h and then quenched with saturated aqueous ammonium chloride (10 mL). The aqueous layer is separated and extracted with hexane (2×25 mL). The combined organics are dried over magnesium sulfate and concentrated in vacuo. The residue is purified by flash chromatography to afford 214.

M. Alcohol 215

To a solution of 214 (0.050 mmol) in dichloromethane (3 mL) at 0° C. is added water (50 mL) and 2,3-dichloro-5,6-dicyano-1,4-benzoquinone (0.018 mmol). After 1 h, the reaction mixture is diluted with ethyl acetate (50 mL), washed with saturated aqueous brine (3×25 mL), dried over magnesium sulfate and concentrated in vacuo. The residue is purified by flash chromatography to afford 215.

N. Carbamate 216

To a solution of 215 (0.010 mmol) in dichloromethane (2 mL) is added trichloroacetyl isocyanate (1.00 mmol). After 30 min, the reaction mixture is diluted with dichloromethane (4 mL) and neutral alumina (1 g) is added. The resultant suspension is stirred an additional 4 h. The reaction mixture is filtered and the concentrated filtrate is chromatographed on silica gel to afford 216.

O. Triol 217

A solution of 216 (0.010 mmol) in 48% hydrofluoric acid-acetonitrile (1:9, 2 mL) is stirred at ambient temperature. After 12 h, saturated aqueous sodium bicarbonate (25 mL) is added and the mixture is extracted with ethyl acetate (3×20 mL). The combined organics are dried over magnesium sulfate and concentrated in vacuo. The residue is purified by flash chromatography to afford 217.

EXAMPLE 53

Figure 21:
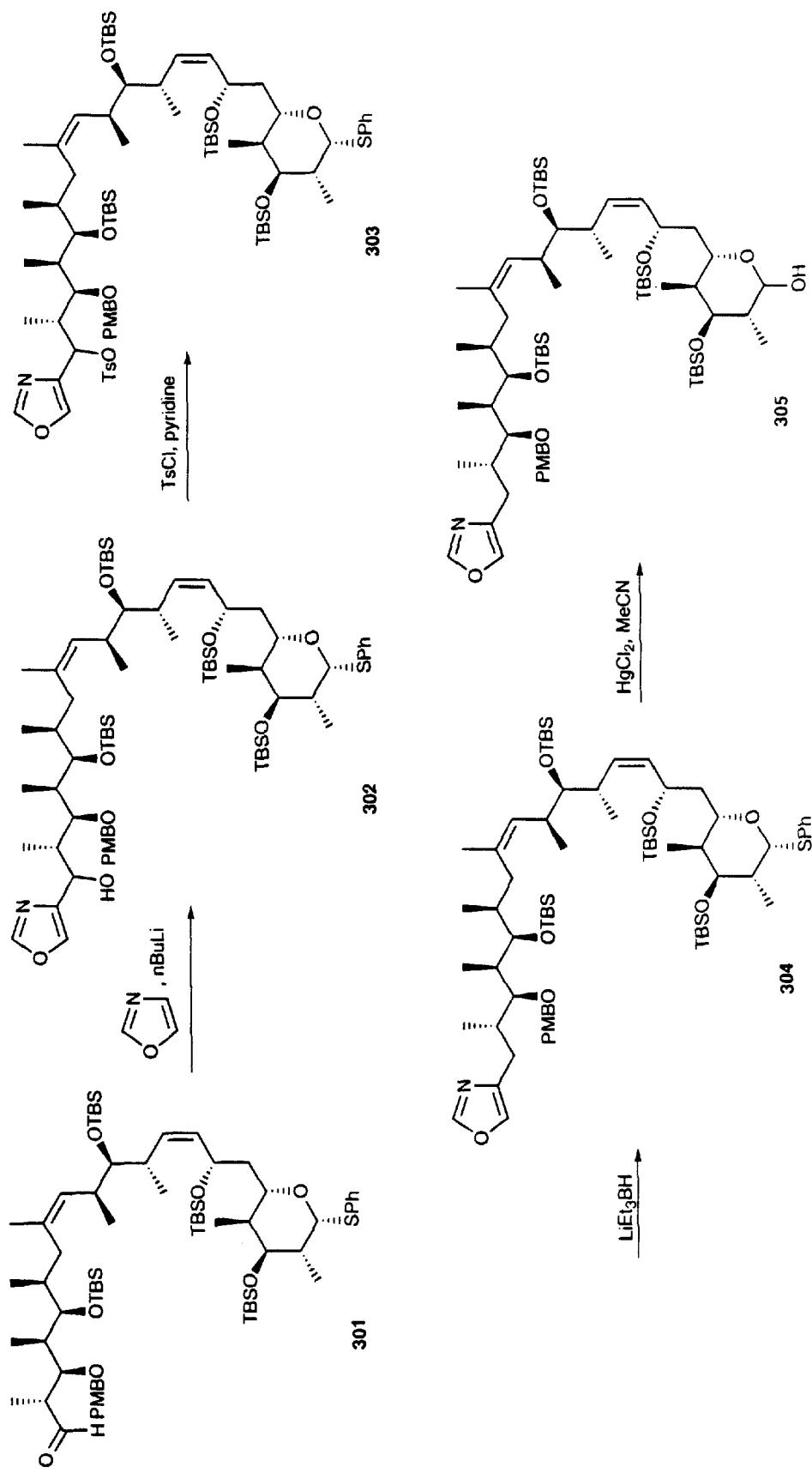
FIG. 21 shows a synthetic scheme for compound 305.
Figure 22:
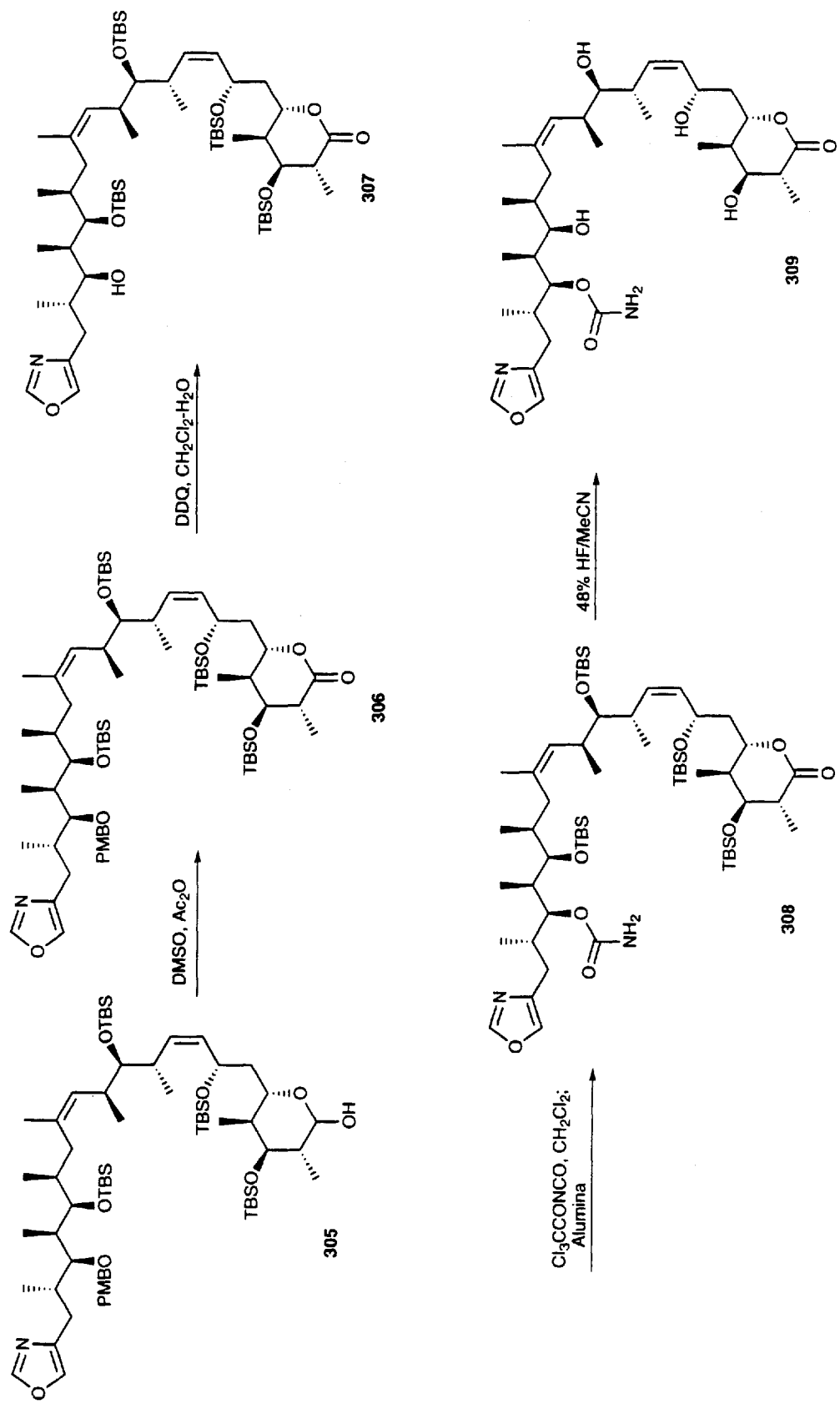
FIG. 22 shows a synthetic scheme for compound 309.

FIGS. 21 and 22

A. Hydroxy-oxazole 302

A solution of oxazole (3 mmol) in tetrahydrofuran (15 mL) is cooled to −78° C. and treated with n-BuLi (3 mmol) in hexane. (see, Hodges, et al., *J. Org. Chem.* 1991, 56, 449). After 30 min at −78° C., previously prepared (see, Smith, et al., *J. Am. Chem. Soc.* 1995, 117, 12011) aldehyde 301 (2 mmol) is added in tetrahydrofuran (10 mL) and the reaction mixture is gradually allowed to warm to room temperature. After 18–24 h, the reaction is quenched by addition of saturated aqueous ammonium chloride (25 mL). The aqueous layer is separated and extracted with ether (3×25 mL). The combined organics are dried over magnesium sulfate and concentrated in vacuo. The residue is purified by flash chromatography to afford 302.

B. Tosylate 303

A solution of 302 (1.0 mmol) in anhydrous pyridine (10 mL) at 0° C. is treated with p-toluenesulfonyl chloride (286 mg, 1.5 mmol). The mixture is allowed to warm to room temperature for 4–6 h. The pyridine is removed in vacuo and the residue is purified by flash chromatography to afford tosylate 303.

C. Reduction product 304

To a 0° C. solution of tosylate 303 (0.5 mmol) in tetrahydrofuran (2 mL) is added lithium triethylborohydride (2 mmol) as a solution in tetrahydrofuran (1.0 M). The resultant solution is warmed to room temperature for 2–4 h and then quenched with water (1 mL) and diluted with ether (25 mL). The ethereal layer is washed with saturated aqueous brine (2×10 mL), dried over magnesium sulfate, and concentrated in vacuo. The residue is purified by flash chromatography to afford 304.

D. Lactol 305

To a solution of 304 (0.1 mmol) in tetrahydrofuran-acetonitrile (15 mL, 2:1) is added phosphate buffer (pH 7, 5 mL) and mercury (II) chloride (1.0 mol). The resultant mixture is stirred 1 h at room temperature. The reaction mixture is diluted with ether (100 mL) and washed with saturated aqueous brine (2×50 mL), dried over magnesium sulfate and concentrated in vacuo. The residue is purified by flash chromatography to afford 305 as a mixture of α and β anomers.

E. Lactone 306

To a solution of 305 (0.070 mmol) in dimethyl sulfoxide (10 mL) is added acetic anhydride (2 mL). After 2 days at room temperature, the mixture is diluted with ether (100 mL) and washed with saturated aqueous sodium bicarbonate (50 mL), saturated aqueous brine (50 mL), dried over magnesium sulfate and concentrated in vacuo. The residue is purified by flash chromatography to afford 306

F. Alcohol 307

To a solution of 306 (0.050 mmol) in dichloromethane (3 mL) at 0° C. is added water (50 mL) and 2,3-dichloro-5,6-dicyano-1,4-benzoquinone (0.018 mmol). After 1 h, the reaction mixture is diluted with ethyl acetate (50 mL), washed with saturated aqueous brine (3×25 mL), dried over magnesium sulfate and concentrated in vacuo. The residue is purified by flash chromatography to afford 307.

G. Carbamate 308

To a solution of 307 (0.010 mmol) in dichloromethane (2 mL) is added trichloroacetyl isocyanate (1.00 mmol). After 30 min, the reaction mixture is diluted with dichloromethane (4 mL) and neutral alumina (1 g) is added. The resultant suspension is stirred an additional 4 h. The reaction mixture is filtered and the concentrated filtrate is chromatographed on silica gel to afford 308.

H. Tetrol 309

A solution of 308 (0.010 mmol) in 48% hydrofluoric acid-acetonitrile (1:9, 2 mL) is stirred at ambient temperature. After 12 h, saturated aqueous sodium bicarbonate (25 mL) is added and the mixture is extracted with ethyl acetate (3×20 mL). The combined organics are dried over magnesium sulfate and concentrated in vacuo. The residue is purified by flash chromatography to afford 309.

EXAMPLE 54

Figure 23:
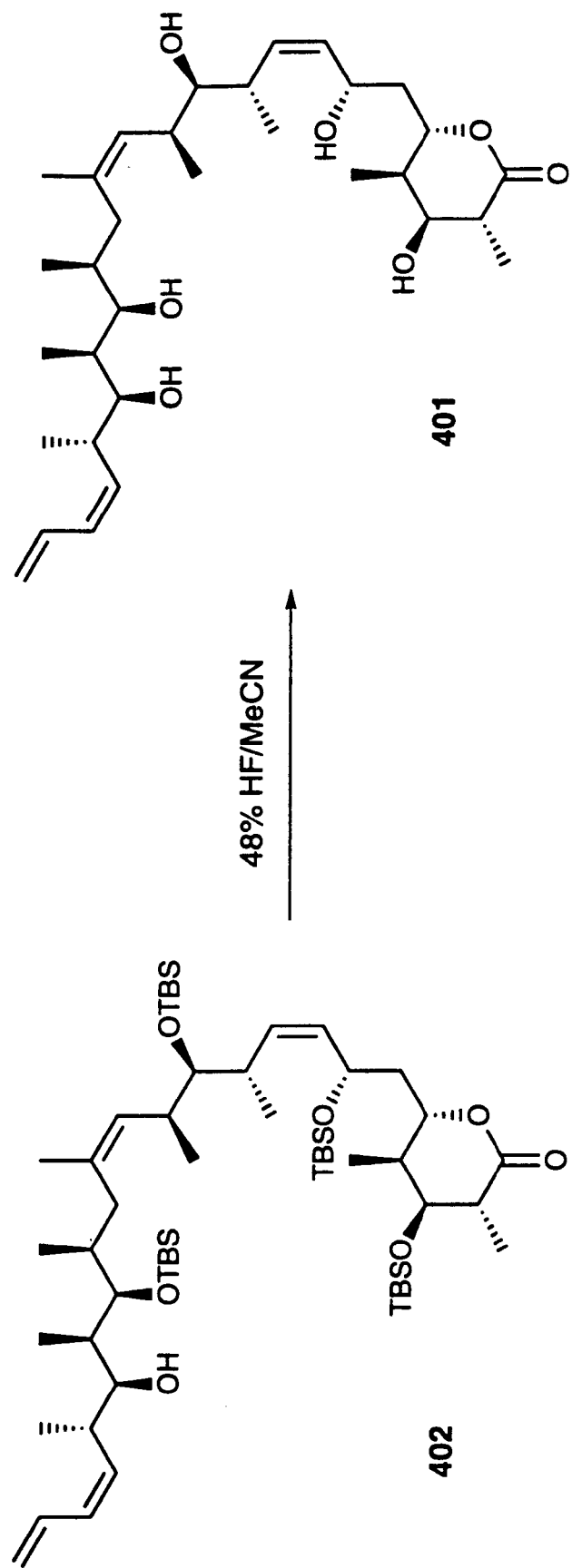
FIG. 23 shows a synthetic scheme for compound 401.
Figure 24:
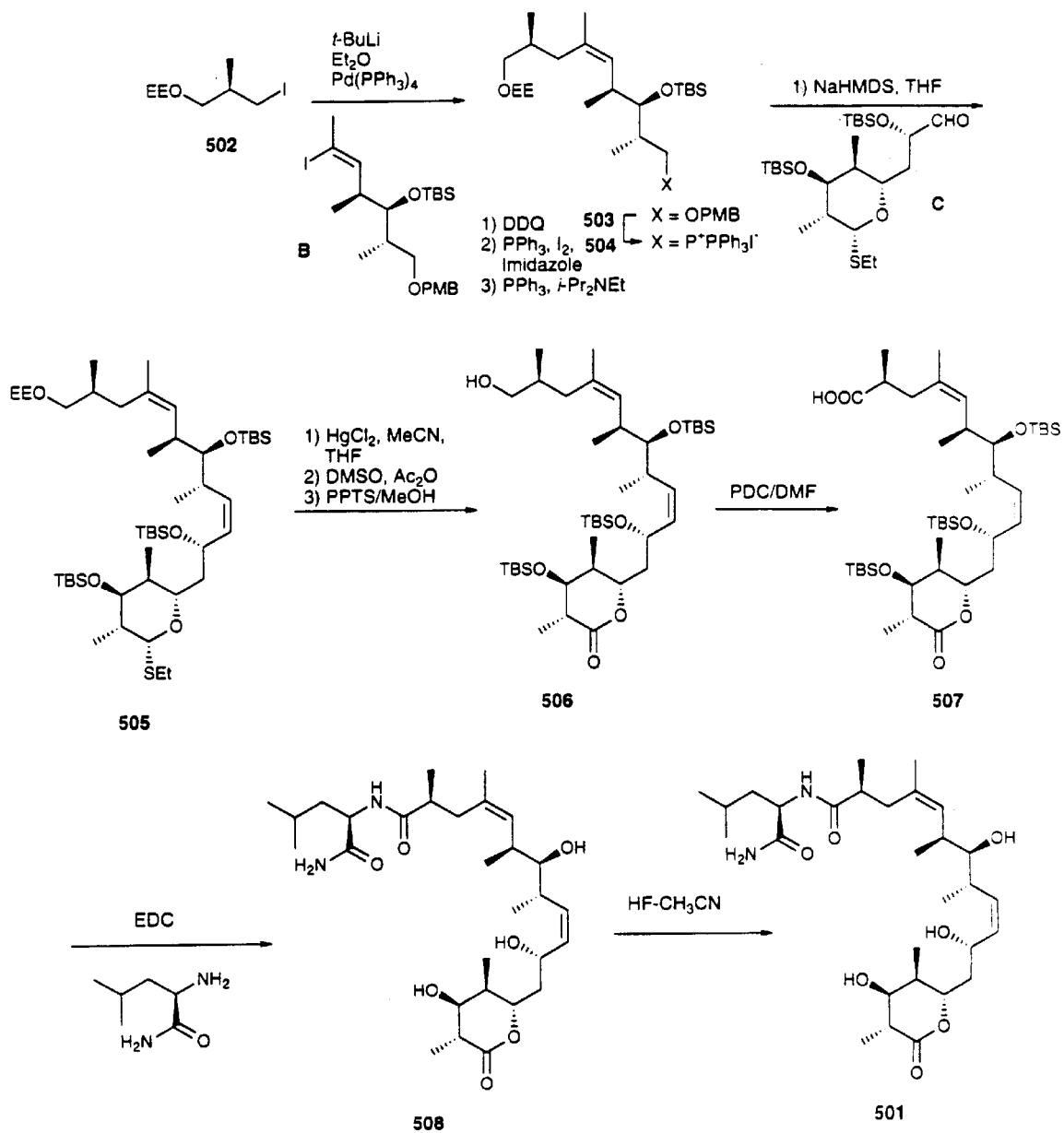
FIG. 24 shows a synthetic scheme for compound 501.
Figure 25:
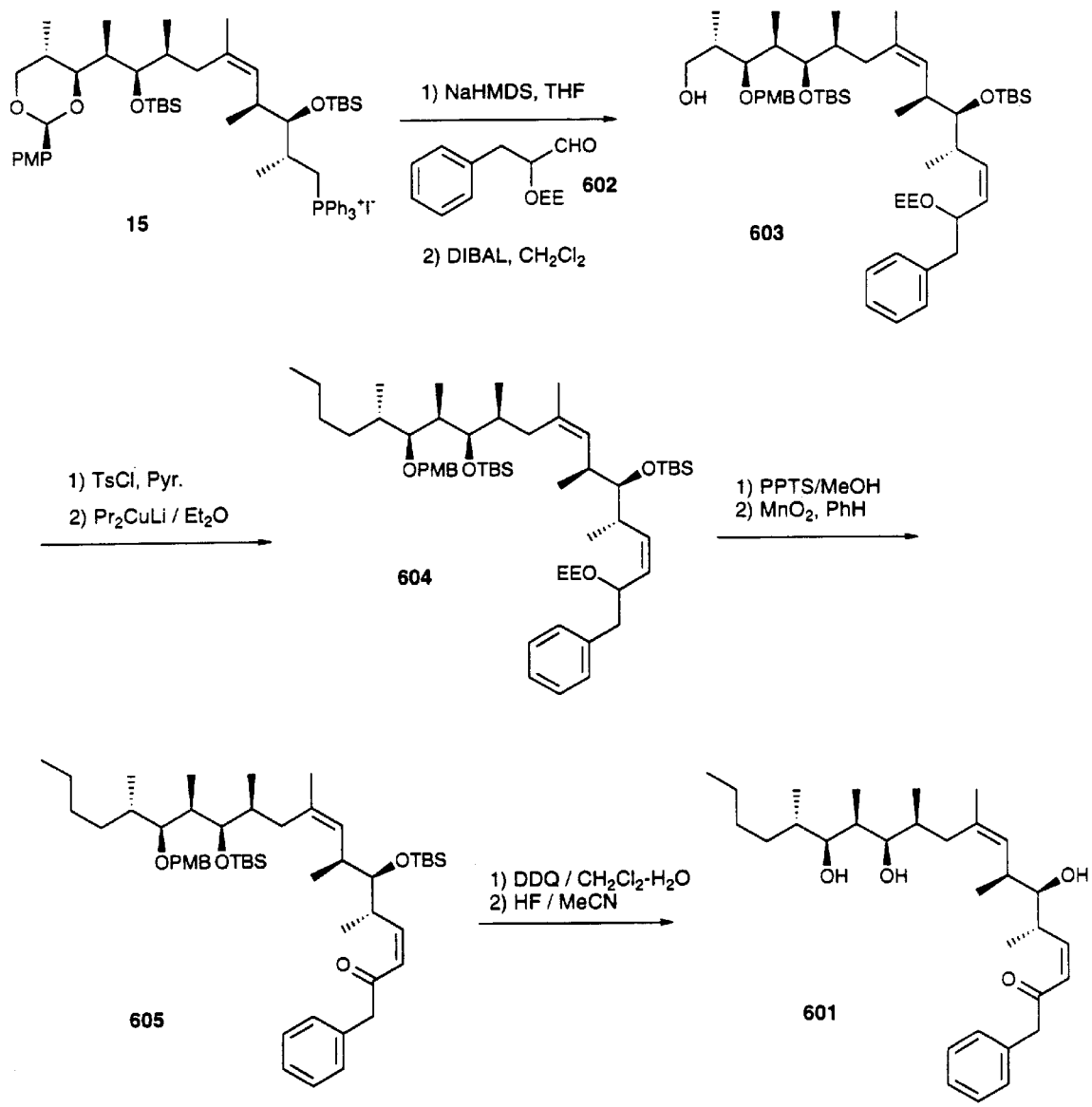
FIG. 25 shows a synthetic scheme for compound 601.
Figure 26:
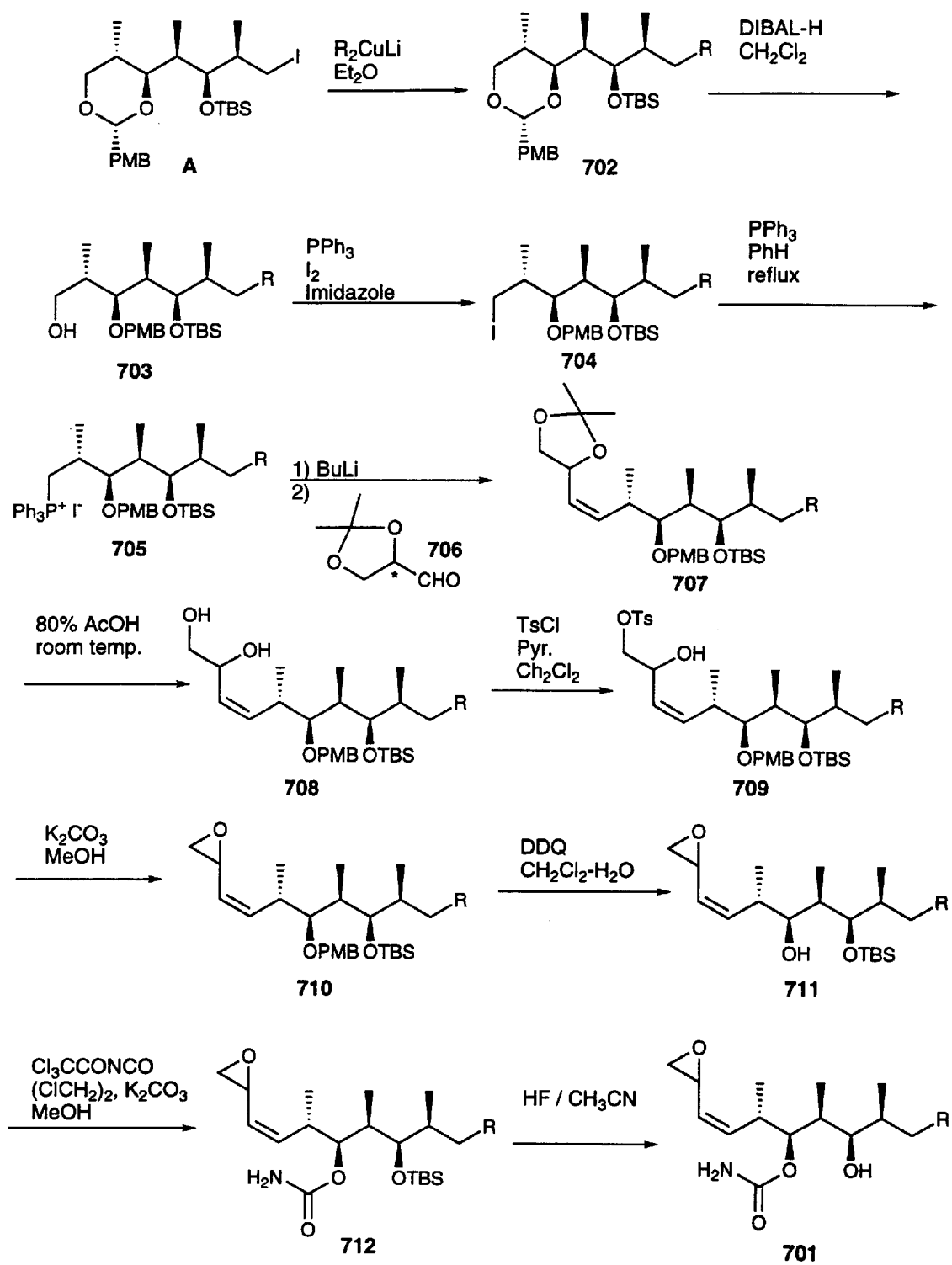
FIG. 26 shows a synthetic scheme for compound 701 (R=alkyl).

As shown in FIG. 23, a solution of 402 (10.5 mg, 10.4 mmol) in 48% HF—$CH_3CN$ (1:9, 1.0 mL) is stirred at room temperature for 12 hr. The reaction is quenched by saturated $NaHCO_3$ (5.0 mL). The mixture is extracted with ethyl acetate (3×10 mL). The combined organic phase is then washed with brine (5.0 mL), dried over $MgSO_4$, concentrated in vacuo. The residue is purified by flash chromatography to afford 401.

EXAMPLE 55

FIG. 24

A. PMB-ether 503

$ZnCl_2$(1.32 g, 9.69 mmol) is dried at 160° C. under vacuum overnight and then treated with a solution of iodide 502 (2.46 g, 9.59 mmol) in dry $Et_2O$ (50 mL). The mixture is stirred at room temperature until most of the $ZnCl_2$ is dissolved and then cooled to −78° C. t-BuLi (1.7M in pentane, 17.0 mL) is added over 30 min, and the resultant solution is stirred an additional 15 min, warmed to room temperature, and stirred for 1 hr. The solution is added by cannula to a mixture of iodoolefin B (see, Smith, et al., *J. Am. Chem. Soc.* 1995, 117, 12011) (3.21 g, 6.19 mmol) and $Pd(PPh_3)_4$ (364.2 mg, 0.315 mmol). The mixture is covered with aluminum foil, stirred overnight, and then diluted with ethyl acetate (100 mL), washed with brine (2×100 mL), dried over $MgSO_4$, filtered and concentrated in vacuo. The residue is purified by flash chromatography to afford 503.

B. Phosphonium salt 504

A solution of alcohol 503 (1.70 g, 3.26 mmol) in $CH_2Cl_2$ (28 mL) is cooled to 0° C. and treated with water (1.3 mL) and 2,3-dichloro-5,6-dicyano-1,4-benzoquinone (774 mg, 3.41 mmol). The mixture is stirred at 0° C. for 5 hr, diluted with $CH_2Cl_2$ (20 mL), dried over $MgSO_4$, and filtered through a column of silica gel. Following concentration in vacuo, the residue is dissolved in ethanol (50 mL) at room temperature, and excess sodium borohydride is added. After 30 min, the reaction is cooled to 0° C., quenched with saturated aqueous $NH_4Cl$ (50 mL), and concentrated. The residue is then dissolved in $CH_2Cl_2$(90 mL), and the solution is washed with water, dried over $MgSO_4$, filtered and concentrated in vacuo. The residue is purified by flash chromatography to afford an alcohol.

A solution of this alcohol (400 mg, 1.0 mmol) in dry benzene/ether (1:2, 50 mL) is treated with triphenylphosphine (923 mg, 3.6 mmol) and imidazole (273 mg, 4.0 mmol). After all of the imidazole dissolved, iodine (761 mg, 3.0 mmol) is added with vigorous stirring of the reaction mixture. The mixture is stirred 2 h further and then treated with triethylamine (4 mL). The resultant solution is diluted with $CH_2Cl_2$ (50 mL) and washed with saturated aqueous $Na_2S_2O_3$(100 mL), saturated aqueous $NaHCO_3$ (100 mL), and brine (2×100 mL). The organic phase is dried over $MgSO_4$, filtered and concentrated in vacuo. Filtration though silica gel to remove triphenylphosphine oxide, affords an iodide. The iodide was mixed with diisopropylethylamine (0.6 mL, 3.44 mmol) and triphenylphosphine (4.94 g, 18.8 mmol). The mixture is heated at 80° C. for 24 hr, cooled to room temperature, and washed with hexane (2×50 mL). The product is isolated by flash chromatography to afford 504.

C. Coupled product 505

Phosphonium salt 504 (386 mg, 0.5 mmol) is dried azeotropically with dry benzene and heated at 50° C. under vacuum for 3 hr before use. It is then dissolved in tetrahydrofuran (3.0 mL). Sodium bis(trimethylsilyl)amide (1.0 M in tetrahydrofuran, 0.48 mL, 0.48 mmol) is added at −78° C., and the mixture is stirred for 25 min and then recooled to −78° C. A solution of aldehyde C (see, Smith, et al., *J. Am. Chem. Soc.* 1995, 117, 12011) (147 mg, 0.30 mmol) in tetrahydrofuran (1.5 mL) is added, and the mixture is stirred for 10 min at −78° C., and 2 hr at room temperature. The reaction is quenched with saturated aqueous $NH_4Cl$ (4.0 mL), the resultant mixture is extracted with ether (120 mL), and the ether layer is washed with water (100 mL) and brine (100 mL), dried over $MgSO_4$, filtered and concentrated in vacuo. Flash chromatography provides olefin 505.

D. Lactone 506

To a solution of 505 (200 mg, 0.23 mmol) in tetrahydrofuran-acetonitrile (10 mL, 2:1) is added a phosphate buffer solution (pH=7.0, 3.3 mL), and $HgCl_2$(1.3 g). The suspension is stirred at room temperature for 40 min, then diluted with ether (150 mL), washed with brine (2×70 mL), dried over $MgSO_4$, and concentrated in vacuo. Flash chromatography provides a mixture of lactols as α/β anomers. This material is used directly in the next oxidation: Under argon, to a solution of lactols in dimethylsulfoxide (5.0 mL) is added acetic anhydride (1.0 mL)). After 2 days at room temperature, the mixture is diluted with ether (150 mL), washed with saturated $NaHCO_3$ (150 mL), brine (150 mL), dried over $MgSO_4$, and concentrated in vacuo. Flash chromatography affords a lactone. A solution of the lactone (160 mg, 0.20 mmol) in methanol (4 mL) is treated with pyridinium p-toluenesulfonate (10 mg) and stirred at 40° C. for 30 min. The mixture is diluted with ether (80 mL) and washed successively with saturated aqueous $NaHCO_3$ solution (90 mL) and brine (40 mL), and then dried over $MgSO_4$. The organic solution is concentrated in vacuo, and the residue is passed through a column of silica gel to provide alcohol 506.

E. Acid 507

To a solution of alcohol 506 (140 mg, 0.19 mmol) in dimethylformamide (5.0 mL), is added pyridinium dichromate (210 mg, 0.55 mmol). The reaction mixture is stirred at room temperature for 5 hr, and diluted with water (120 mL). The mixture is extracted with ether (3×15 mL). The organic solutions are combined and washed with brine (40 mL), and dried over $MgSO_4$. Then it is concentrated in vacuo to give a residue, which is purified by flash chromatography to afford carboxylic acid 507.

F. Amino-amide 508

To a solution of 507 (60.0 mg, 78.1 mmol) and D-leucine hydrochloride (26.0 mg, 0.16 mmol) in $CH_2Cl_2$ (3 mL) is added 1-(3-dimethylaminopropyl)-3-ethylcarbodiimide hydrochloride (EDC, 23 mg, 0.12 mmol) and 1-hydroxybenzotriazole (21.0 mg, 0.14 mmol), followed by diisopropylamine (40 mL, 0.23 mmol). The mixture is stirred at room temperature overnight before addition of 5% $KHSO_4$ solution. The resulting mixture is extracted with ethyl acetate (30 mL). The organic layer is washed with brine (20 mL) and dried over $MgSO_4$, and then concentrated in vacuo. The residue is purified by column chromatography to afford 508.

G. Analog 501

A solution of 508 (52 mg, 59 mmol) in 48% HF-acetonitrile (1:9, 1.0 mL) is stirred at room temperature for 12 hr. The reaction is quenched by saturated $NaHCO_3$ (5.0 mL). The mixture is extracted with ethyl acetate (3×10 mL). The combined organic phase is then washed with brine (5.0 mL), dried over $MgSO_4$, and concentrated in vacuo. Flash chromatography provides 501.

EXAMPLE 56

FIG. 25

A. Diene 603

Phosphonium salt 15 (98.0 mg, 0.092 mmol) is dried azeotropically with dry benzene and heated at 50° C. under vacuum for 3 hr before use. It is then dissolved in tetrahydrofuran (0.7 mL). Sodium bis(trimethylsilyl)amide (1.0 M in tetrahydrofuran, 86 mL, 0.0855 mmol) is added at −78° C., and the mixture is stirred for 20 min and then recooled to −78° C. A solution of aldehyde 602 (13 mg, 60 mmol) in tetrahydrofuran (300 mL) is added, and the mixture is stirred for 10 min at −78° C., and 2 hr at room temperature. The reaction is quenched with saturated aqueous $NH_4Cl$ (1.0 mL). The resultant mixture is extracted with ether (30 mL), and the ether layer is washed with water (30 mL) and brine (30 mL), dried over $MgSO_4$, filtered and concentrated in vacuo. Flash chromatography provides the coupled product.

A solution of the olefin (39 mg, 44 mmol) in $CH_2Cl_2$ is cooled to −78° C., diisobutylaluminum hydride (1.0 M in toluene, 440 mL, 0.40 mmol) is added dropwise over 5 min, and the resultant solution is stirred for 10 min at −78° C. and 30 min at 0° C. The reaction is quenched with a saturated solution of Rochelle's salt, and the mixture is diluted with ether (60 mL), washed with Rochelle solution, and brine(30 mL each), dried over $MgSO_4$, filtered and concentrated in vacuo. Flash chromatography provides alcohol 603.

B. Alkane 604

To a solution of alcohol 603 (82 mg, 0.93 mmol) in pyridine (1.5 mL) at 0° C. is added p-toluenesulfonyl chloride (26.6 mg, 0.14 mmol) with stirring. After 3 hr, the reaction mixture is concentrated in vacuo. The residue is purified by column chromatography to give a tosylate. To a solution of this tosylate (94 mg, 0.91 mmol) in ether (5 mL) is added lithium diisopropylcuprate ($Pr_2CuLi$) (ca. 0.5 M in ether, 10 mL, excess. The resultant solution is stirred for 8 hr and then quenched with saturated aqueous solution of $NH_4Cl$ (50 mL). Stirring is continued for an additional 2 h. The organic phase is separated and washed with $NH_4Cl$ solution (20 mL), dried over $MgSO_4$, and concentrated in vacuo. Flash chromatography provides 604.

C. Enone 605

A solution of 604 (75 mg, 83 mmol) in methanol (2 mL) is treated with pyridinium p-toluenesulfonate (ca.4 mg) and stirred at 40° C. for 30 min. The mixture is diluted with ether (20 mL) and washed successively with saturated aqueous $NaHCO_3$ solution (25 mL) and brine (10 mL), and then dried over MgSO$_4$. The organic solution is concentrated in vacuo, and the residue is passed through a column of silica gel to provide an alcohol. To a solution of the alcohol (62.0 mg, 68.2 mmol) in benzene (2.0 mL) is added manganese(IV) oxide (100 mg, 1.15 mmol) After stirring for 8 h at room temperature, the reaction mixture is filtered through a pad of celite. The filtrate is concentrated in vacuo. Flash chromatography of the residue affords α,β-unsaturated ketone 605.

D. Triol 606

A solution of the α,β-unsaturated ketone 605 (45 mg, 56 mmol) in CH$_2$Cl$_2$ (2 mL) is cooled to 0° C. and treated with water (0.1 mL) and 2,3-dichloro-5,6-dicyano-1,4-benzoquinone (15 mg, 66 mmol). The mixture is stirred at 0° C. for 5 hr, diluted with CH$_2$Cl$_2$ (15 mL), dried over MgSO$_4$, and filtered through a column of silica gel. Following concentration in vacuo, the residue is used for next step without further purification. A solution of the crude alcohol in 48% HF-acetonitrile (1:9, 1.0 mL) is stirred at room temperature for 12 hr. The reaction is quenched by saturated NaHCO$_3$ (5.0 mL). The mixture is extracted with ethyl acetate (3×10 mL). The combined organic phase is then washed with brine (5.0 mL), dried over MgSO$_4$, concentrated in vacuo. The residue is purified by flash chromatography to afford 601.

EXAMPLE 57

FIG. 26

A. Alkane 702

To a solution of iodide A (300 mg, 0.54 mmol) in ether (5 mL) is added lithium dibutylcuprate (Bu$_2$CuLi) (ca. 0.5 M in ether, 5.4 mL, excess) at -25° C. The resultant solution is stirred for 8 hr and then quenched with saturated aqueous NH$_4$Cl (50 mL). Stirring is continued for another 2 hr and the organic phase is separated. The organic solution is washed with NH$_4$Cl solution (20 mL) and dried over MgSO$_4$, and concentrated in vacuo. Flash chromatography provides 702.

B. Alcohol 703

A solution of 702 (240 mg, 0.50 mmol) in CH$_2$Cl$_2$ (6.0 mL) is cooled to -78° C. Diisobutylaluminum hydride (1.0 M in toluene, 1.50 mL, 1.50 mmol) is added dropwise over 5 min, and the resultant solution is stirred for 10 min at -78° C. and 30 min at 0° C. The reaction is quenched with a saturated solution of Rochelle's salt, and the mixture is diluted with ether (60 mL), washed with Rochelle solution, and brine (30 mL each), dried over MgSO$_4$, filtered and concentrated in vacuo. Flash chromatography provides alcohol 703.

C. Iodide 704

A solution of alcohol 703 (210 mg, 0.44 mmol) in dry benzene/ether (1:2, 5 mL) is treated with triphenylphosphine (420 mg, 1.6 mmol) and imidazole (123 mg, 1.8 mmol). After all of the imidazole dissolved, iodine (335 mg, 1.32 mmol) is added with vigorous stirring. The mixture is stirred for 2 h and then treated with triethylamine (1.8 mL). The resultant solution is diluted with CH$_2$Cl$_2$ (22 mL) and washed with saturated aqueous Na$_2$S$_2$O$_3$ (40 mL), saturated aqueous NaHCO$_3$ (40 mL), and brine (2×40 mL). The organic phase is dried over MgSO$_4$, filtered and concentrated in vacuo. The residue is purified by flash chromatography to afford iodide 704.

D. Phosphonium salt 705

The iodide 704 is mixed with triphenylphosphine (2.17 g, 8.27 mmol) and the mixture is heated at 80° C. for 24 hr, cooled to room temperature, and washed with hexane (2×20 mL). Flash chromatography provides phosphonium salt 705.

E. Alkene 707

A solution of 705 (260 mg, 0.30 mmol) in tetrahydrofuran (6.0 mL) is cooled to -10° C. and a solution of n-butyl lithium (1.0 M in hexane, 0.29 mL, 0.29 mmol) is introduced dropwise over 5 min. The resultant solution is stirred for 50 min at room temperature and then the mixture is recooled to -78° C. and aldehyde 706 (39 mg, 0.3 mmol) is added a solution in tetrahydrofuran (1.5 mL). The mixture is stirred for 10 min at -78° C., and 1 hr at 0° C. The reaction is quenched with saturated aqueous NH$_4$Cl (1.0 mL) and the resultant mixture is extracted with ether (30 mL). The ether layer is washed with water (30 mL) and brine (30 mL), dried over MgSO$_4$, filtered and concentrated in vacuo. The residue is purified by flash chromatography to afford olefin 707 (149 mg, 85% yield).

F. Diol 708

Acetonide 707 (147 mg, 0.25 mmol) is dissolved in 80% aqueous acetic acid (2.5 mL) at room temperature. The reaction mixture is stirred for 4 hr at room temperature and then diluted with water (20 mL). The mixture is extracted with ethyl acetate (2×5 mL). The combined organic layers are washed with saturated NaHCO$_3$ solution, and brine (10 mL each), and then dried over MgSO$_4$. The organic solution is concentrated in vacuo, and the residue is flash chromatogaraphed over silica gel to afford diol 708.

G. Tosylate 709

To a solution of diol 708 (134 mg, 0.25 mmol) in pyridine (2 mL) is added p-toluenesulfonyl chloride (52 mg, 0.27 mmol). After 3 hr, the reaction mixture is diluted with ether (30 mL), and washed with ice cold 1 M hydrochloric acid (60 mL), saturated NaHCO$_3$ solution (20 mL), and brine (20 mL) and then concentrated in vacuo. The residue is purified by column chromatography to give a monotosylate 709.

H. Epoxide 710

A solution of tosylate 709 (145 mg, 0.21 mmol) in methanol (3.0 mL) is added potassium carbonate (10 mg) at room temperature. The mixture is stirred for 20 min, and then diluted with water (60 mL) and extracted with ethyl acetate (2×20 mL). The combined organic layers are washed with brine and concentrated in vacuo. Flash chromatography provides epoxide 710.

I. Alcohol 711

To a solution of 710 (41 mg, 79 mmol) in CH$_2$Cl$_2$ (3.0 mL) at 0° C. is added water (0.15 mL) and 2,3-dichloro-5,6-dicyano-1,4-benzoquinone (60 mg, 0.26 mmol). The mixture is stirred at 0° C. for 5 hr, diluted with CH$_2$Cl$_2$ (15 mL), dried over MgSO$_4$, and filtered through a column of silica gel. Following concentration in vacuo, the crude 711 is used without further purification.

J. Carbamate 712

To a solution of 711 (8.7 mg, 22 mmol) in CH$_2$Cl$_2$ (1.0 mL) is added trichloroacetyl isocyanate (0.20 mL, 1.7 mmol) at room temperature. After 30 min, the mixture is diluted with CH$_2$Cl$_2$ (20 mL), and some neutral Al$_2$O$_3$ (500 mg) is added. The mixture is then stirred at room temperature for 2 hr, then filtered though a short column of silica gel, and concentrated in vacuo. The residue is purified by flash chromatography to afford 712.

K. Hydroxy-urethane 701

A solution of 712 (6.0 mg, 14 mmol) in 48% HF-acetonitrile (1:9, 1.0 mL) is stirred at room temperature for 12 hr. The reaction is quenched by saturated NaHCO$_3$ (5.0 mL). The mixture is extracted with ethyl acetate (3×10 mL). The combined organic phase is then washed with brine (5.0 mL), dried over MgSO$_4$, and concentrated in vacuo. The residue is purified by flash chromatography afford 701.

EXAMPLE 58

Figure 27:
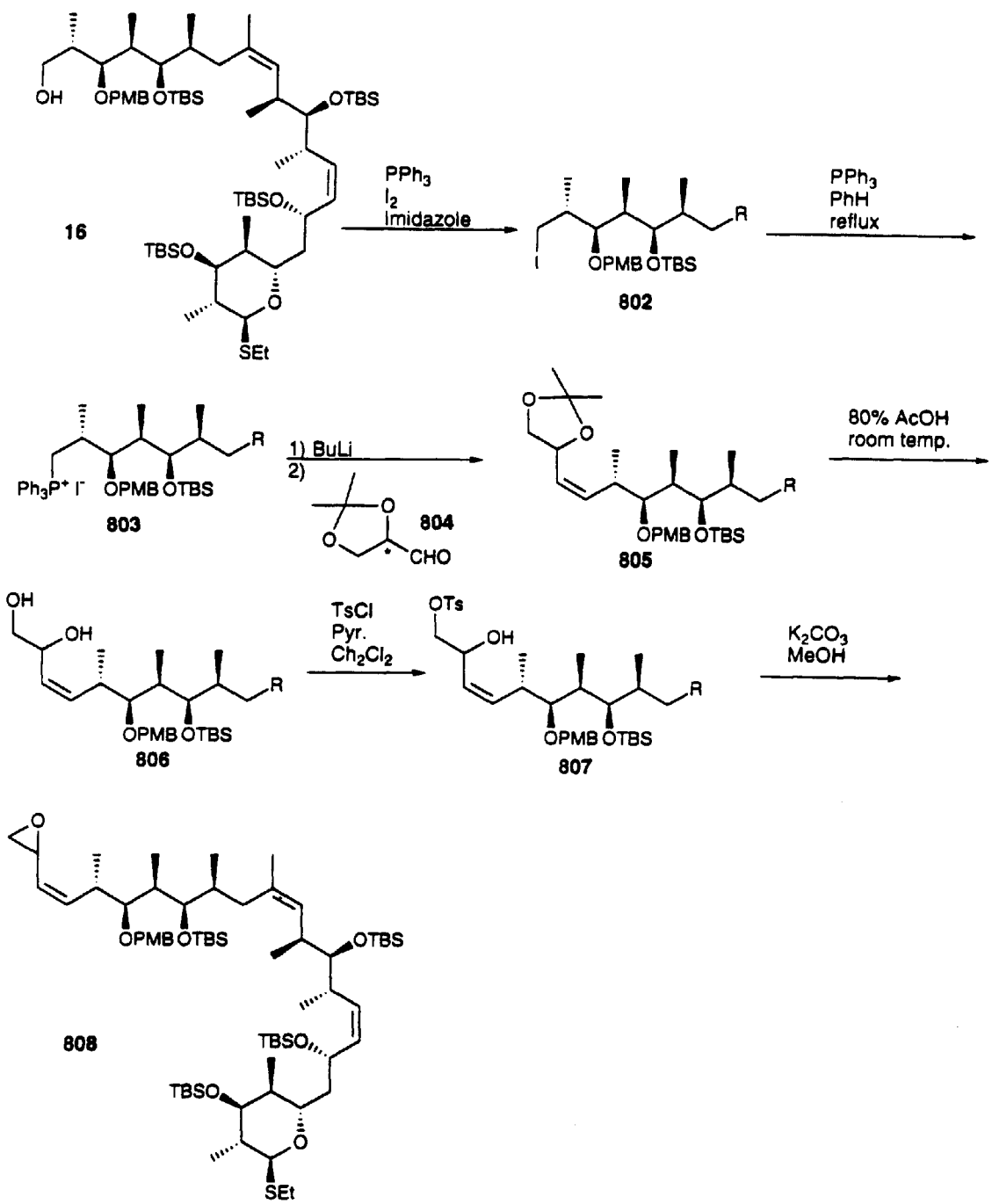
FIG. 27 shows a synthetic scheme for compound 808.
Figure 28:
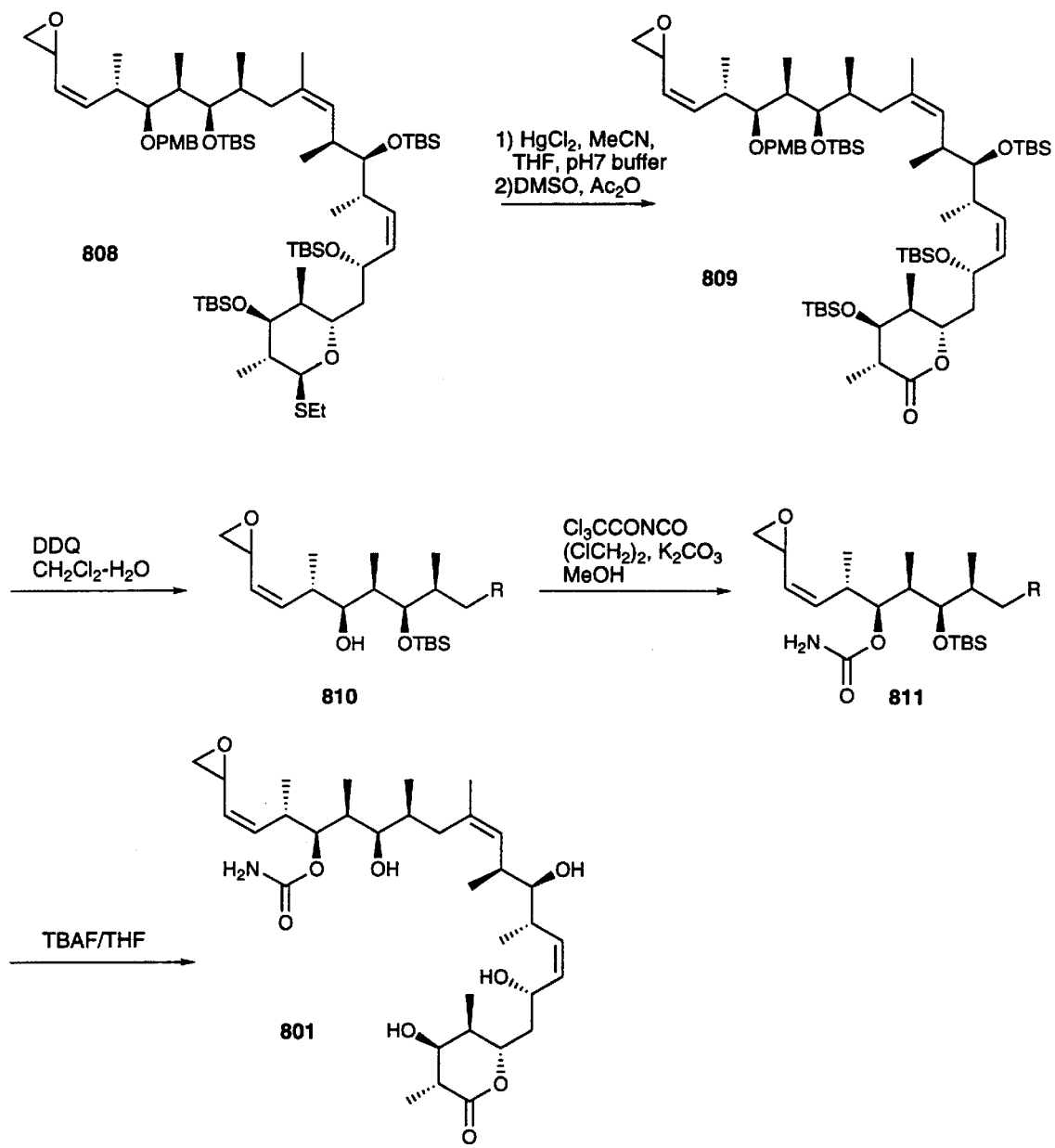
FIG. 28 shows a synthetic scheme for compound 801.
Figure 29:
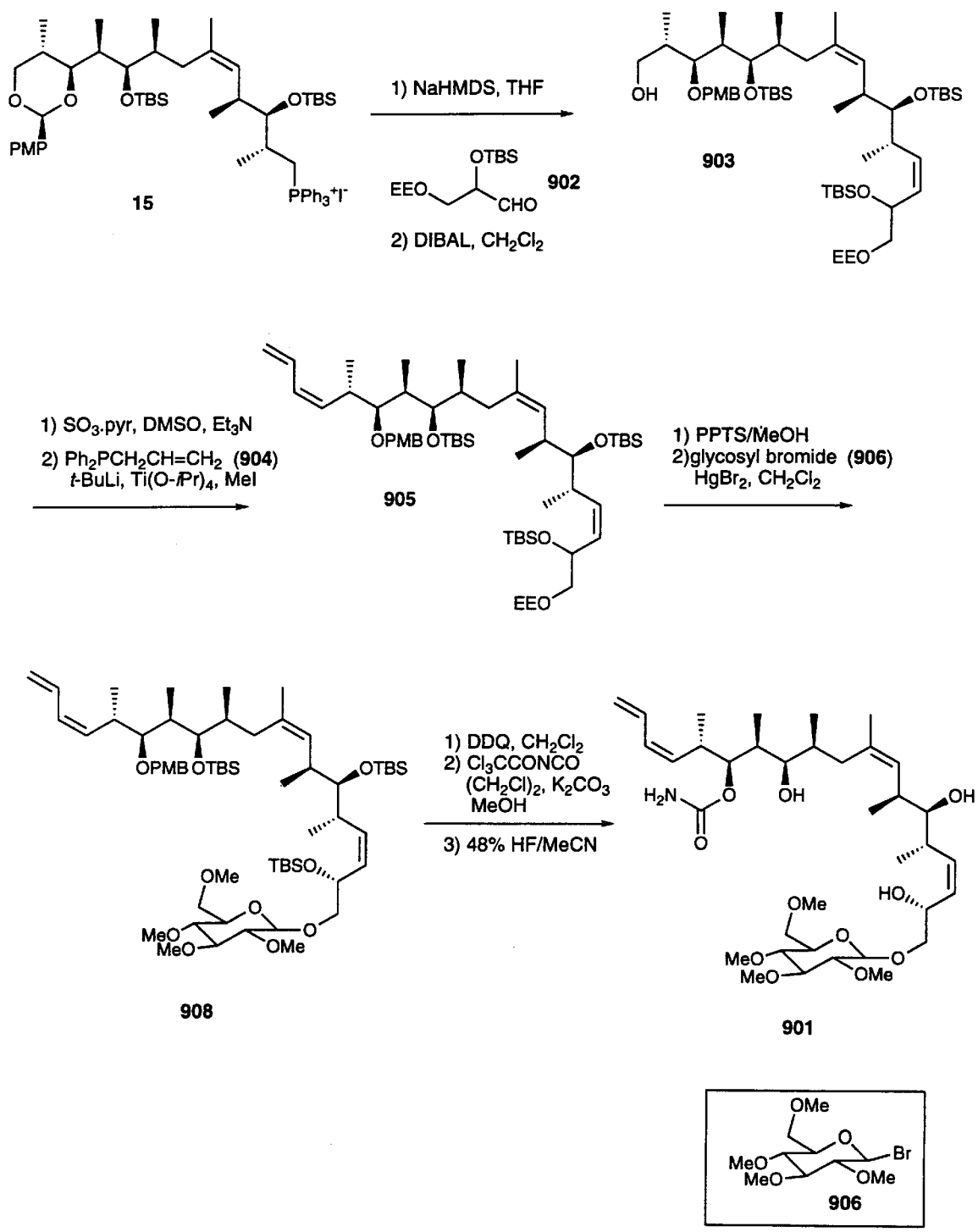
FIG. 29 shows a synthetic scheme for compound 901.
Figure 30:
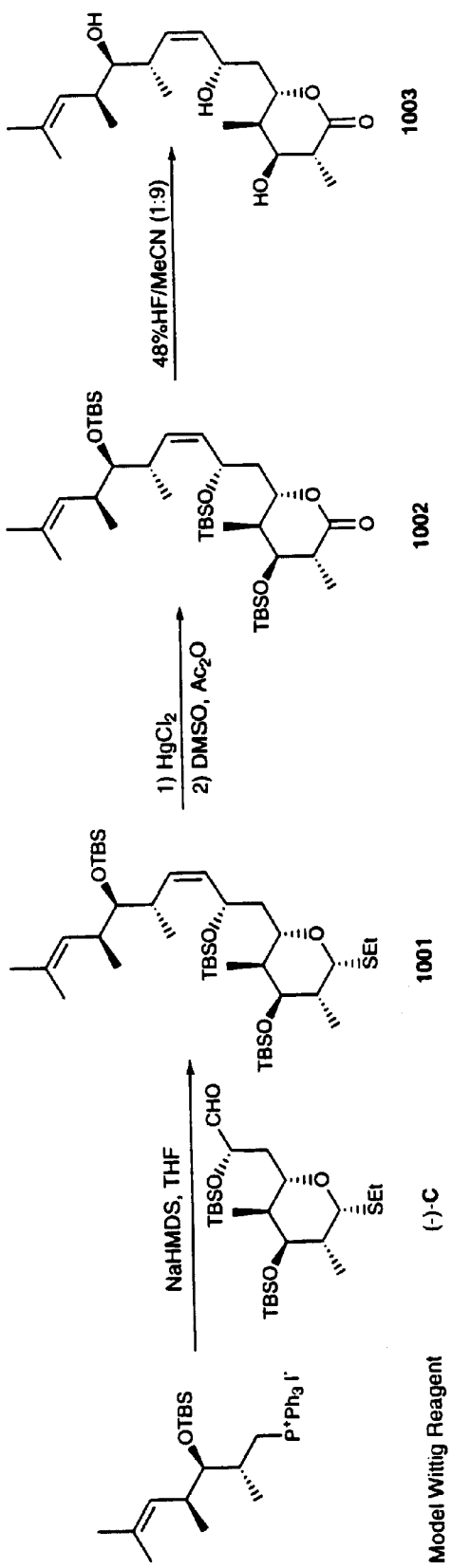
FIG. 30 shows a synthetic scheme for compound 1003.

FIGS. 27 and 28

A. Iodide 802

A solution of alcohol 16 (see, Smith, et al., *J. Am. Chem. Soc.* 1995, 117, 12011) (410 mg, 0.360 mmol) in dry benzene/ether (1:2, 10 mL) is treated with triphenylphosphine (378 mg, 1.44 mmol) and imidazole (111 mg, 1.62 mmol). After complete dissolution of the imidazole, iodine (301 mg, 1.19 mmol) is added with vigorous stirring. The reaction mixture is stirred 2 h and then treated with triethylamine (1.7 mL). The resultant solution is diluted with $CH_2Cl_2$ (30 mL) and washed with saturated aqueous $Na_2S_2O_3$ (40 mL), saturated aqueous $NaHCO_3$ (40 mL), and brine (2×40 mL). The organic phase is dried over $MgSO_4$, filtered and concentrated in vacuo. Purification of the residue by flash chromatography affords iodide 802.

B. Phosphonium salt 803

To a solution of iodide 802 (410 mg, 0.325 mmol) in benzene (20 mL) is added triphenylphosphine (1.00 g, 3.81 mmol). The mixture is heated at 80° C. for 24 hr, cooled to room temperature, and concentrated in vacuo. The residue is washed with hexane (2×20 mL). Flash chromatography affords phosphonium salt 803.

C. Alkene 805

A solution of 803 (460 mg, 0.30 mmol) in tetrahydrofuran (9.0 mL) is cooled to −10° C. A solution of n-butyl lithium (1.0 M in hexane, 0.29 mL, 0.29 mmol) is added dropwise over 5 min, and the resultant solution is stirred for 50 min at room temperature. Then the mixture is recooled to −78° C. and a solution of aldehyde 804 (39 mg, 0.3 mmol) in tetrahydrofuran (1.5 mL) is added. The mixture is stirred for 10 min at −78° C., and 1 hr at 0° C. The reaction is quenched with saturated aqueous $NH_4Cl$ (20 mL), the resultant mixture is extracted with ether (40 mL), and the ether layer is washed with water (30 mL) and brine (30 mL), dried over $MgSO_4$, filtered and concentrated in vacuo. Flash chromatography of the residue affords 805.

D. Diol 806

Acetonide 805 (280 mg, 0.22 mmol) is dissolved in 80% aqueous acetic acid (3.5 mL) at room temperature. The reaction mixture is stirred for 4 hr at room temperature and then diluted with water (40 mL). The mixture is extracted with ethyl acetate (2×10 mL). The combined organic layers are washed with saturated $NaHCO_3$ solution, and brine (10 mL each), and then dried over $MgSO_4$. The organic solution is concentrated in vacuo, and the residue is flash chromatogaraphed over silica gel to afford diol 806.

E. Tosylate 807

To a solution of diol 806 (235 mg, 0.19 mmol) in pyridine (2 mL) at 0° C. is added p-toluenesulfonyl chloride (45 mg, 0.23 mmol). After 3 hr, the reaction mixture is diluted with ether (30 mL), and washed with ice cold 1 M hydrochloric acid (30 mL), saturated $NaHCO_3$ solution (20 mL), and brine (20 mL) and then concentrated in vacuo. The residue is purified by column chromatography to give a monotosylate 807.

F. Epoxide 808

To a solution of tosylate 807 (187 mg, 0.21 mmol) in methanol (3.0 mL) is added potassium carbonate (10 mg) at room temperature. The mixture is stirred for 20 min, and then diluted with water (60 mL) and extracted with ethyl acetate (2× 20 mL). The combined organic layers were washed with brine and concentrated in vacuo. Flash chromatography provides epoxide 808.

G. Lactone 809

To a solution of 808 (110 mg, 93 mmol) in tetrahydrofuran-acetonitrile (10 mL, 2:1) is added a phosphate buffer solution (pH=7.0, 3.5 mL), and $HgCl_2$ (2.3 g). The suspension is stirred at room temperature for 40 min, then diluted with ether (30 mL), washed with brine (2×30 mL), dried over $MgSO_4$, and concentrated in vacuo. Flash chromatography affords the lactol as an α/β anomeric mixture. This material is used directly in the next oxidation: Under argon atmosphere, a solution of the lactols in dimethylsulfoxide (3.0 mL) is treated with acetic anhydride (0.60 mL). After 2 days at room temperature, the mixture is diluted with ether (50 mL), washed with saturated $NaHCO_3$ (30 mL), brine (30 mL), dried over $MgSO_4$, and concentrated in vacuo. Flash chromatography provides 809.

H. Alcohol 810

To a solution of 809 (90 mg, 79 mmol) in $CH_2Cl_2$ (3.0 mL) at 0° C. is added water (0.15 mL) and 2,3-dichloro-5,6-dicyano-1,4-benzoquinone (60 mg, 0.26 mmol). The mixture is stirred at 0° C. for 5 hr, diluted with $CH_2Cl_2$ (15 mL), dried over $MgSO_4$, and filtered through a column of silica gel. Following concentration in vacuo, the crude 810 is used in the next reaction without further purification.

I. Carbamate 811

To a solution of 810 (22 mg, 22 mmol) in $CH_2Cl_2$ (1.0 mL) is added trichloroacetyl isocyanate (0.20 mL, 1.7 mmol) at room temperature. After 30 min, the mixture is diluted with $CH_2Cl_2$(20 mL), and some neutral $Al_2O_3$ (500 mg) is added. The mixture is then stirred at room temperature for 2 hr, then filtered though a short column of silica gel, and concentrated in vacuo. Flash chromatography affords 811.

J. Epoxide analog 812

A solution of 811 (15 mg, 14 mmol) in tetrahydrofuran (1.0 mL) is cooled to 0° C., and treated with a 1.0 M solution of tetrabutylammonium fluoride in tetrahydrofuran (0.14 mL, 0.14 mmol). The reaction mixture is stirred for 2 hr, and diluted with water (20 mL). The mixture is extracted with ethyl acetate (3×10 mL). The combined organic phase is then washed with brine (10 mL), dried over $MgSO_4$, concentrated in vacuo. Flash chromatography affords 801.

EXAMPLE 59

FIG. 29

A. Alcohol 903

Phosphonium salt 15 (98.0 mg, 0.092 mmol) is dried azeotropically with dry benzene and heated at 50° C. under vacuum for 3 hr before use. It is then dissolved in tetrahydrofuran (0.7 mL). Sodium bis(trimethylsilyl)amide (1.0 M in tetrahydrofuran, 86 mL, 0.0855 mmol) is added at −78° C., and the mixture is stirred for 20 min and then recooled to −78° C. A solution of aldehyde 902 (60 mmol) in tetrahydrofuran (300 mL) is added, and the mixture is stirred for 10 min at −78° C., and 2 hr at room temperature. The reaction is quenched with saturated aqueous $NH_4Cl$ (1.0 mL). The resultant mixture is extracted with ether (30 mL), and the ether layer is washed with water (30 mL) and brine (30 mL), dried over $MgSO_4$, filtered and concentrated in vacuo. Flash chromatography provides an olefin. A solution of the olefin (44 mmol) in $CH_2Cl_2$ is cooled to −78° C. Diisobutylaluminum hydride (1.0 M in toluene, 440 mL, 0.40 mmol) is added dropwise over 5 min, and the resultant solution is stirred for 10 min at −78° C. and 30 min at 0° C. The reaction is quenched with a saturated solution of Rochelle's salt, and the mixture is diluted with ether (60 mL), washed with Rochelle solution, and brine (30 mL each), dried over $MgSO_4$, filtered and concentrated in vacuo. Flash chromatography provides alcohol 903.

B. Diene 905

A solution of 903 (0.012 mmol) and $Et_3N$ (42 mL, 0.30 mmol) in $CH_2Cl_2$ (2.0 mL) is cooled to 0° C. and a solution of $SO_3$-pyridine complex (40 mg, 0.251 mmol) in dimethylsulfoxide (0.6 mL) is added. The mixture is stirred at 0° C. for 45 min and then diluted with ethyl acetate (30 mL), washed with aqueous $NaHSO_4$ (1.0 M, 30 mL) and brine (2×30 mL), dried over $MgSO_4$, and concentrated in vacuo.

Flash chromatography affords an aldehyde. A solution of allyldiphenylphosphine 904 (0.19 mmol) in tetrahydrofuran (1.0 mL) is cooled to −78° C. and t-butyl lithium (1.7 M in pentane, 0.122 mmol) is added. The mixture is stirred at 0° C. for 30 min, recooled to −78° C. and treated titanium tetra-i-propoxide (0.15 mmol). After 30 min, a cold (−78° C.) solution of the aldehyde (0.26 mmol) in tetrahydrofuran (1.0 mL) is introduced via cannula, and the mixture is stirred 10 min further at −78° C. and at 0° C. for 1 hr. Iodomethane (0.32 mmol) is added, and the reaction is maintained at 0° C. for 30 min, warmed to room temperature, protected from light, and stirred overnight. The reaction mixture is diluted with ether (30 mL), washed with 1.0 M aqueous $NaHSO_4$ and brine (30 mL each), dried over $MgSO_4$, concentrated in vacuo. Flash chromatography affords diene 905.

C. Glycoside 908

A solution of 905 (83 mmol) in methanol (2 mL) is treated with pyridinium p-toluenesulfonate (ca.4 mg) and stirred at 40° C. for 30 min. The mixture is diluted with ether (20 mL) and washed successively with saturated aqueous $NaHCO_3$ solution (25 mL) and brine (10 mL), and then dried over $MgSO_4$. The organic solution is concentrated in vacuo, and the residue is passed through a column of silica gel to give an alcohol.

To a solution of glycosyl bromide 906 (75 mmol) in $CH_2Cl_2$ (2.0 mL) is added $HgBr_2$ (7 mmol) and powdered molecular sieves (4 Å, 50 mg) and stirred for 60 min at room temperature. The mixture is then cooled to 0° C., and the alcohol (74 mmol) prepared above is added in $CH_2Cl_2$ (0.7 mL). The resultant mixture is stirred 6 hr at 0° C. and then warmed to room temperature and diluted with $CH_2Cl_2$ (10 mL), and filtered through a pad of celite. The filtrate is washed with aqueous KI solution, and dried over $MgSO_4$. The organic solution is concentrated in vacuo, and the residue is passed through a column of silica gel to give an anomeric mixture of glycosides 908.

D. Triol 901

To a solution of 908 (79 mmol) in $CH_2Cl_2$ (3.0 mL) at 0° C. is added water (0.15 mL) and 2,3-dichloro-5,6-dicyano-1,4-benzoquinone (60 mg, 0.26 mmol). The mixture is stirred at 0° C. for 5 hr, diluted with $CH_2Cl_2$ (15 mL), dried over $MgSO_4$, and filtered through a column of silica gel. Following concentration in vacuo, the crude alcohol is used for next step without further purification. To a solution of the alcohol (22 mmol) in $CH_2Cl_2$ (1.0 mL) is added trichloroacetyl isocyanate (0.20 mL, 1.7 mmol) at room temperature. After 30 min, the mixture is diluted with $CH_2Cl_2$ (20 mL), and some neutral $Al_2O_3$ (500 mg) is added. The mixture is then stirred at room temperature for 2 hr, then filtered though a short column of silica gel, and concentrated in vacuo. Flash chromatography affords a carbamate. A solution of the carbamate (14 mmol) in 48% HF-acetonitrile (1:9, 1.0 mL) is stirred at room temperature for 12 hr. The reaction is quenched by saturated $NaHCO_3$ (5.0 mL). The mixture is extracted with ethyl acetate (3×10 mL). The combined organic phase. is then washed with brine (5.0 mL), dried over $MgSO_4$, concentrated in vacuo. Flash chromatography affords 901.

EXAMPLE 60

FIG. 30

A. Olefin 1001

A solution of model phosphonium salt (0.0917 mmol) in THF (700 mL) is cooled to −78° C. and treated with NaHMDS (1.0 M in THF, 85.5 mL, 0.0855 mmol). The mixture is stirred for 20 min at 0° C., recooled to −78° C. and aldehyde C (0.0570 mmol) in THF (300 mL) is added. After 10 min at −78° C. and 2 h at room temperature, the mixture is quenched with saturated aqueous $NH_4Cl$ (1.0 mL) and extracted with ether (30 mL). The ether solution is washed with water, brine (30 mL each), dried over $MgSO_4$, filtered and concentrated. Flash chromatography provides olefin 1001.

B. Lactone 1002

A solution of olefin 1001 (0.00597 mmol) in $THF/CH_3CN$ (2:1, 1.50 mL) is treated with pH 7.0 phosphate buffer (500 mL) and $HgCl_2$ (215 mg). The suspension is stirred at room temperature for 40 min, diluted with ether (30 mL), washed with brine (2×30 mL), dried over $MgSO_4$, filtered and concentrated. Pipette flash chromatography (5% ethyl acetate/hexane) provides a mixture of lactols as a colorless oil which is further treated with DMSO (1.0 mL) and $Ac_2O$ (200 mL) at room temperature for 2 days. The mixture is diluted with ether (30 mL), washed with saturated $NaHCO_3$ (30 mL), brine (30 mL), dried over $MgSO_4$, filtered and concentrated. Flash chromatography provides lactone 1002.

C. Model Compound 1003

A solution of olefin 1002 (5.5 mmol) in 48% $HF$—$CH_3CN$ (1:9, 1.0 mL) is stirred at room temperature for 12 h, then quenched with saturated aqueous $NaHCO_3$ (5.0 mL). The mixture is extracted with ethyl acetate (3×10 mL). The combined organic extracts are washed with brine (5.0 mL), dried over $MgSO_4$, filtered and concentrated. Pipette flash chromatography (gradient elution, 1:30 to 1:6 $MeOH/CHCl_3$) provides 1003.

EXAMPLE 61

Figure 31:
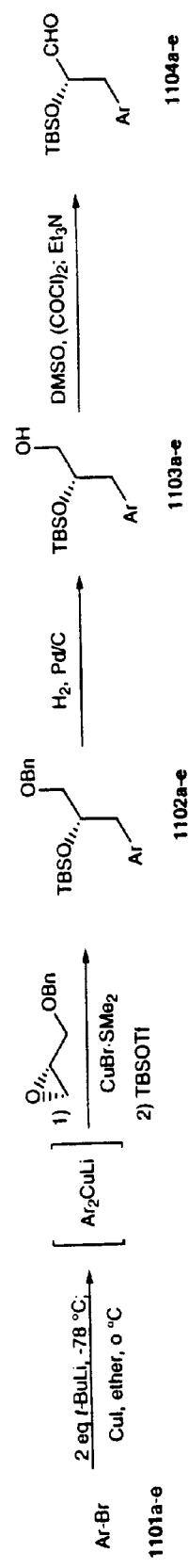
FIG. 31 shows a synthetic scheme for compound 1104 (Ar=2,4-dimethyl-3-methoxyphenyl (a), 2-methyl-5-methoxyphenyl (b), 2,4-dimethyl-5-methoxyphenyl (c), 2,4-dimethylphenyl (d), and 4-methylphenyl (e)).
Figure 32:
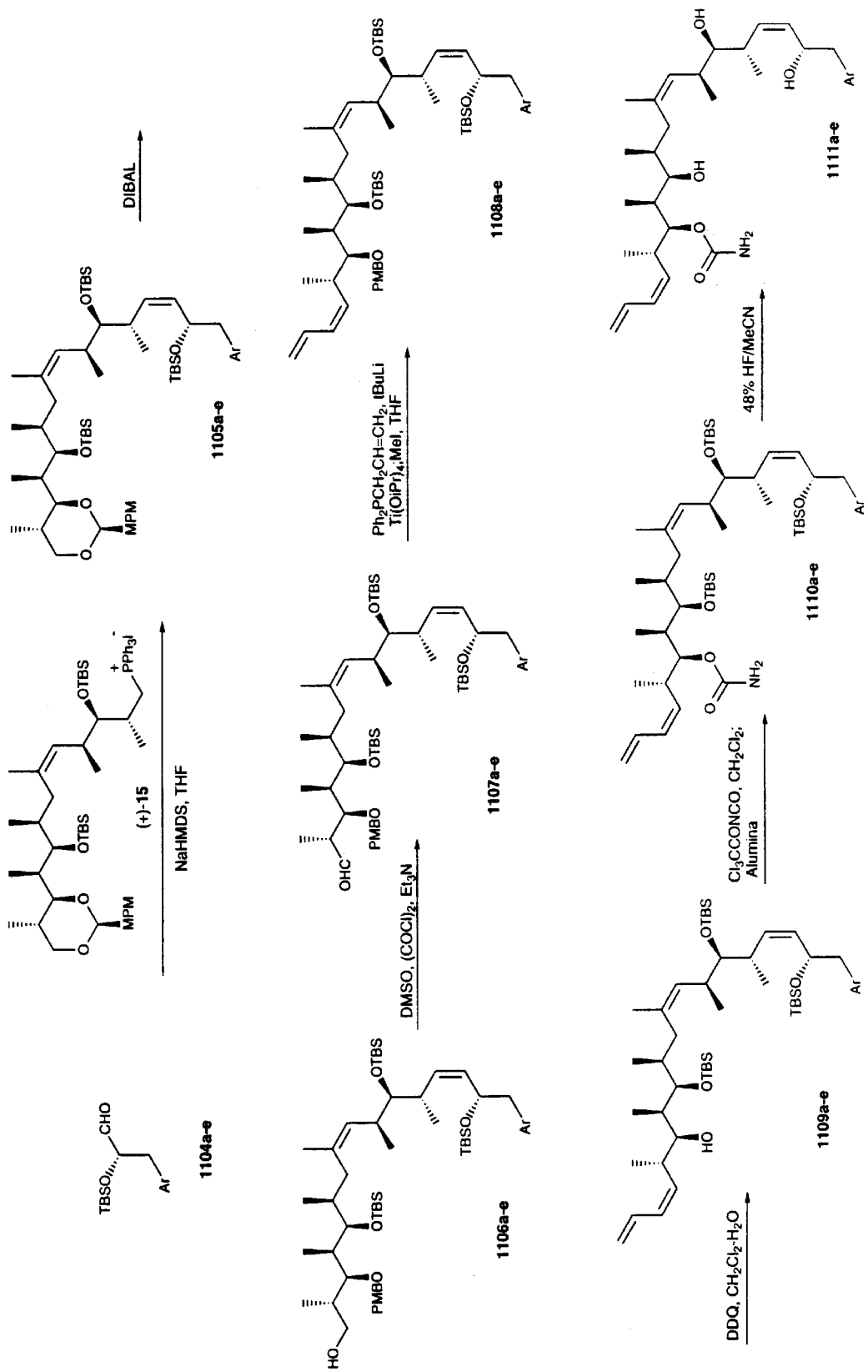
FIG. 32 shows a synthetic scheme for compound 1111.
Figure 33:
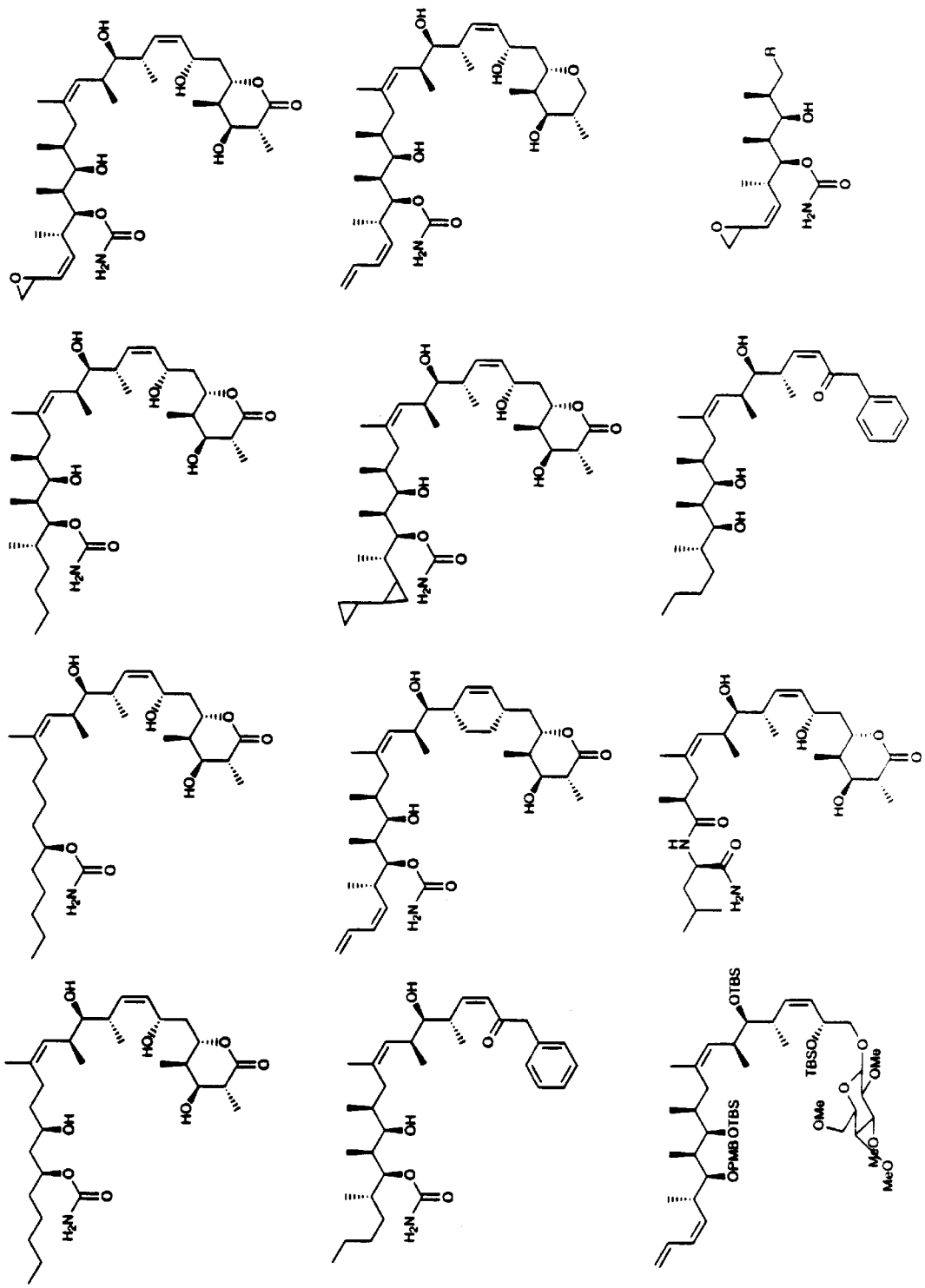
FIGS. 33–36 show representative compounds of the invention.
Figure 34:
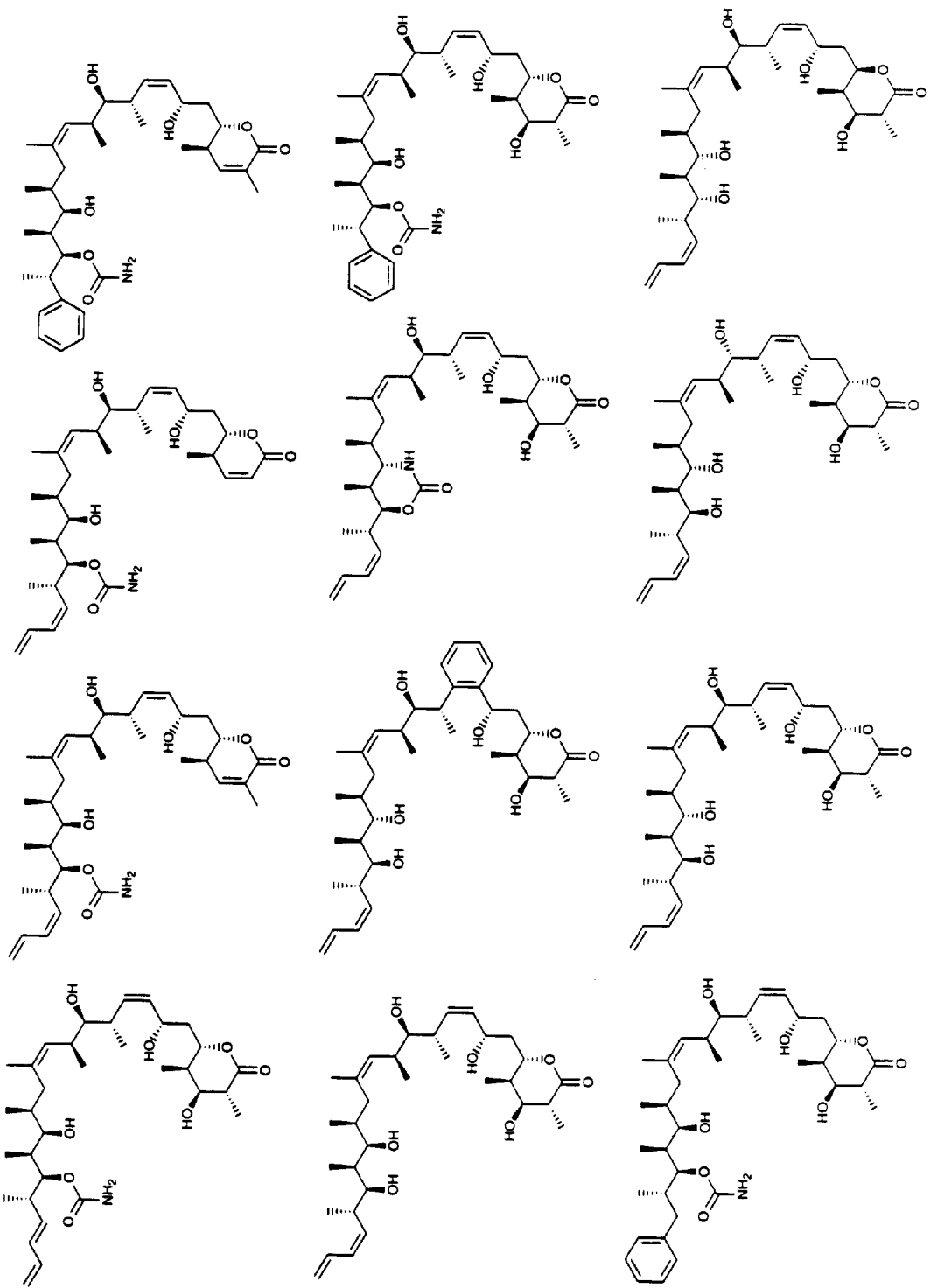
Figure 35:
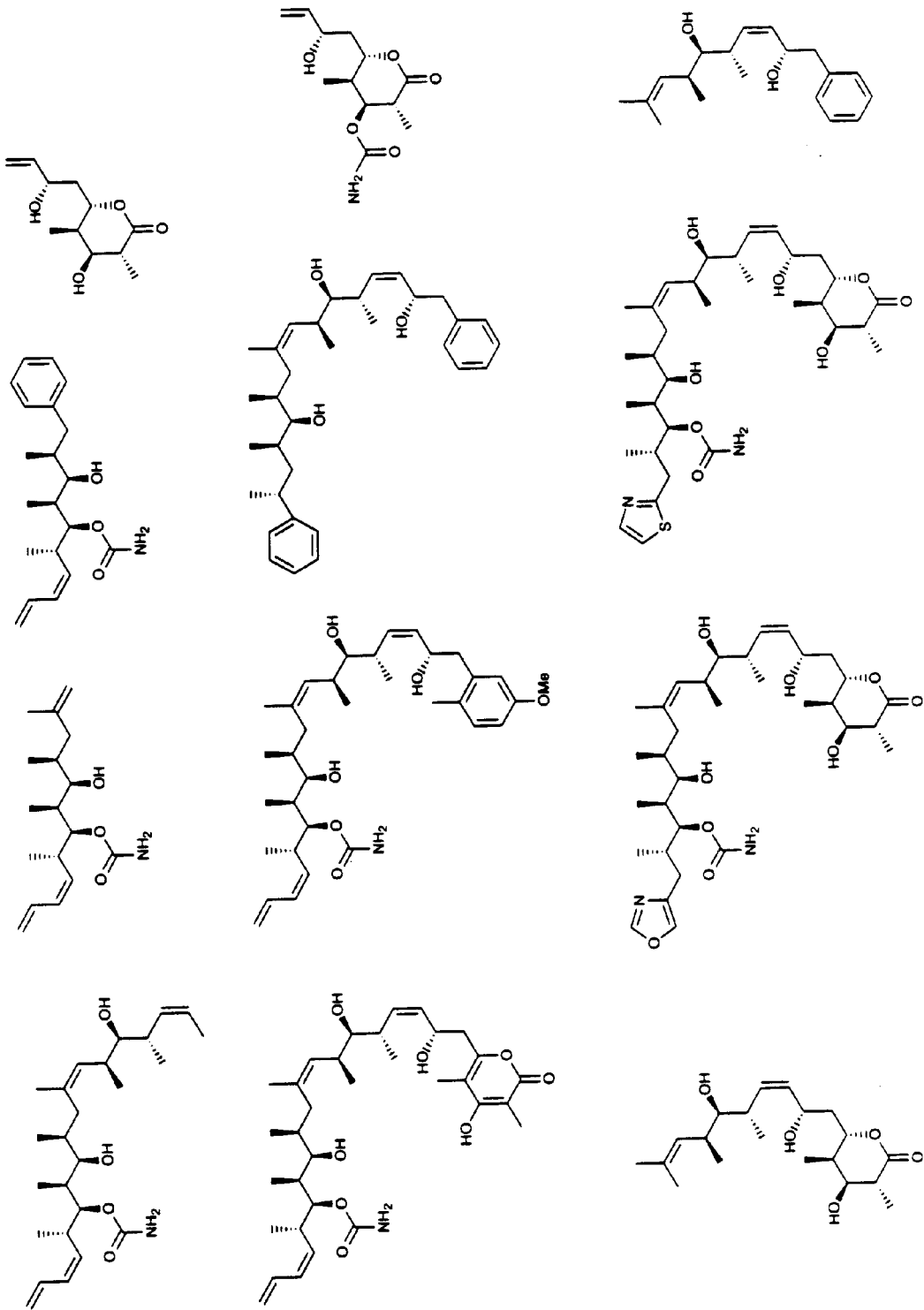
Figure 36:
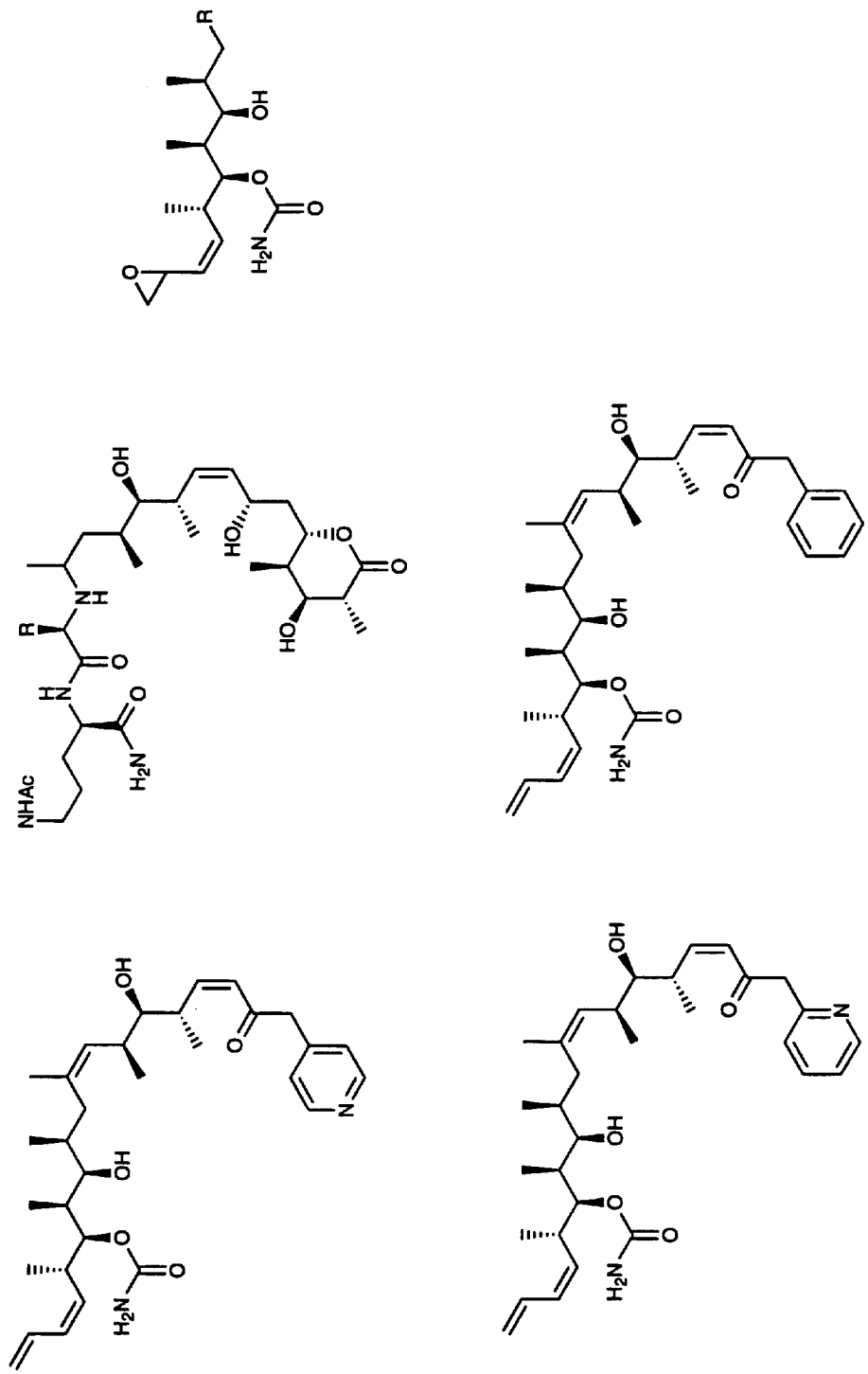

FIGS. 31 and 32

I. General Procedure for Synthesis of Hydroxy Aldehydes 1104

A. TBS ether 1102a

A solution of bromide 1101a (see, Jacquesy, et al., *Tetrahedron* 1981, 37, 747) (20 mmol) in ether (40 mL) is added slowly to a −78° C. solution of tert-butyllitium (40 mmol, 1.7 M in pentane). After 1 h at −78° C., the cold solution is transferred to a suspension of copper (I) iodide (10 mmol) in ether at 0° C. After an additional 30 min at 0° C., a solution of benzyl (S)-(+)-glycidyl ether (9 mmol) in ether (20 mL) is added and the reaction is allowed to warm to room temperature. After 18–24 h, the reaction is quenched by the addition of tert-butyldimethylsilyl triflate (10 mmol). The reaction mixture is poured into saturated aqueous sodium bicarbonate (100 mL). The aqueous layer is separated and extracted with ether (2×50 mL). The combined organics are washed with saturated aqueous brine (50 mL), dried over magnesium sulfate and concentrated in vacuo. The residue is purified by flash chromatography to afford 1102a.

B. Alcohol 1103a.

To a solution of 1102a (6 mmol) in ethyl acetate-ethanol (8:1, 90 mL) is added palladium on carbon (10% wet, 500 mg). The mixture is stirred under hydrogen atmosphere for 3–6 h, then filtered and concentrated in vacuo. The residue is purified by flash chromatography to afford 1103a.

C. Aldehyde 1104a.

Oxalyl chloride (1.5 mmol) is added dropwise to a −78° C. solution of dimethyl sulfoxide (3 mmol) in dichloromethane (4 mL). After 15 min, a −78° C. solution of 1103a (1 mmol) in dichloromethane (2 mL) is added via canula. After an additional 15 min, diisopropylethylamine (4.5 mmol) is added and the reaction is gradually warmed to room temperature over 1 h and quenched with aqueous sodium bisulfate. The mixture is diluted with ether (50 mL) and is washed with water (2×30 mL), saturated aqueous brine (2×30 mL), is dried over magnesium sulfate and concentrated in vacuo. The residue is purified by flash chromatography to afford 1104a.

II. General Procedure for the Conversion of 1104 to Arene Analog 1111

A. Diene 1105

Phosphonium salt 15 (see, Smith, et al., *J. Am. Chem. Soc.* 1995, 117, 12011) (0.2 mmol) is dissolved in anhydrous tetrahydrofuran (2 mL) and chilled to 0° C. A solution of sodium bis(trimethylsilyl)amide (0.2 mmol, 1.0 M in tetrahydrofuran) is added and the reaction mixture is stirred 30 min at 0° C. After cooling to −78° C., a solution of aldehyde 1104 (0.1 mmol) in tetrahydrofuran (2 mL) is added and the mixture is stirred 10 min at −78° C. and 2 h at room temperature. Saturated aqueous ammonium chloride (2 mL) is added and the resultant mixture is extracted with ether (3×20 mL). The ethereal layer is washed with water (2×25 mL) and saturated aqueous brine (25 mL), dried over magnesium sulfate and concentrated in vacuo. The residue is purified by flash chromatography to afford 1105.

B. Hydroxy diene 1106

A −78° C. solution of 1105 (0.05 mmol) in $CH_2Cl_2$ (5 mL) is treated with diisobutylaluminum hydride (0.5 mL, 1.0 M in toluene). The resultant solution is stirred 10 min at −78° C. and 30 min at 0° C. The reaction is quenched with a saturated solution of sodium potassium tartrate (50 mL) and the mixture is diluted with ether (60 mL). The organic layer is separated, dried over magnesium sulfate, and concentrated in vacuo. The residue is purified by flash chromatography to afford 1106.

C. Aldehyde 1107

Oxalyl chloride (1.5 mmol) is added dropwise to a −78° C. solution of dimethyl sulfoxide (3 mmol) in dichloromethane (4 mL). After 15 min, a −78° C. solution of 1106 (1 mmol) in dichloromethane (2 mL) is added via canula. After an additional 15 min, diisopropylethylamine (4.5 mmol) is added and the reaction is gradually warmed to room temperature over 1 h and quenched with aqueous sodium bisulfate. The mixture is diluted with ether (50 mL) and is washed with water (2×30 mL), saturated aqueous brine (2×30 mL), is dried over magnesium sulfate and concentrated in vacuo. The residue is purified by flash chromatography to afford 1107.

D. Tetraene 1108

A solution of diphenylallylphosphine (0.08 mL, 0.38 mmol) in tetrahydrofuran (2 mL) is cooled to −78° C. and tert-butyllithium (0.14 mL, 1.7 M in pentane) is added. The mixture is warmed to 0° C. for 30 min, then recooled to −78° C. and treated with titanium (IV) isopropoxide (0.30 mmol). After 30 min, aldehyde 1107 (0.30 mmol) is introduced as a solution in tetrahydrofuran (2 mL). The resultant solution is stirred at −78° C. for 15 min and at 0° C. for 1 h. Methyl iodide (0.64 mmol) is added, and the reaction is warmed to room temperature for 12 h. The reaction mixture is diluted with ether (60 mL), washed with aqueous sodium bisulfate (30 mL, 1.0 M), saturated aqueous brine (30 mL), and is dried over magnesium sulfate and concentrated in vacuo. The residue is purified by flash chromatography to afford 1108.

E. Alcohol 1109

To a solution of 1108 (0.050 mmol) in dichloromethane (3 mL) at 0° C. is added water (50 mL) and 2,3-dichloro-5,6-dicyano-1,4-benzoquinone (0.018 mmol). After 1 h, the reaction mixture is diluted with ethyl acetate (50 mL), washed with saturated aqueous brine (3×25 mL), dried over magnesium sulfate and concentrated in vacuo. The residue is purified by flash chromatography to afford 1109.

F. Carbamate 1110

To a solution of 1109 (0.010 mmol) in dichloromethane (2 mL) is added trichloroacetyl isocyanate (1.00 mmol). After 30 min, the reaction mixture is diluted with dichloromethane (4 mL) and neutral alumina (1 g) is added. The resultant suspension is stirred an additional 4 h. The reaction mixture is filtered and the concentrated filtrate is chromatographed on silica gel to afford 1110.

G. Arene analog 1111

A solution of 1110 (0.010 mmol) in 48% hydrofluoric acid-acetonitrile (1:9, 2 mL) is stirred at ambient temperature. After 12 h, saturated aqueous sodium bicarbonate (25 mL) is added and the mixture is extracted with ethyl acetate (3×20 mL). The combined organics are dried over magnesium sulfate and concentrated in vacuo. The residue is purified by flash chromatography to afford 1111.

Those skilled in the art will appreciate that numerous changes and modifications may be made to the preferred embodiments of the invention and that such changes and modifications may be made without departing from the spirit of the invention. It is therefore intended that the appended claims cover all equivalent variations as fall within the true spirit and scope of the invention.

What is claimed is:

1. A compound of the formula:

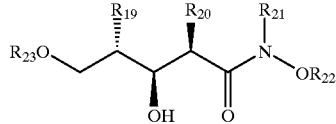

wherein $R_{19}$, $R_{20}$, $R_{21}$ and $R_{22}$ are, independently, $C_1$–$C_{10}$ alkyl; and $R_{23}$ is $C_7$–$C_{15}$ aralkyl.

2. The compound of claim 1 wherein $R_{19}$, $R_{20}$, $R_{21}$ and $R_{22}$ are, independently, $C_1$–$C_4$ alkyl.

3. The compound of claim 2 wherein $R_{19}$, $R_{20}$, $R_{21}$ and $R_{22}$ are methyl.

4. The compound of claim 1 wherein $R_{23}$ is p-methoxybenzyl.

5. The compound of claim 1 wherein:

$R_{19}$, $R_{20}$, $R_{21}$ and $R_{22}$ are methyl; and $R_5$ is p-methoxybenzyl.

* * * * *

UNITED STATES PATENT AND TRADEMARK OFFICE
CERTIFICATE OF CORRECTION

PATENT NO. : 6,031,133
DATED : February 29, 2000
INVENTOR(S) : Amos B. Smith, III et al.

It is certified that error appears in the above-identified patent and that said Letters Patent is hereby corrected as shown below:

Column 9,
Line 27, after "its" delete "a" and insert -- α --

Column 19,
Line 65, "740%" should be -- 74% --

Column 47,
Line 10, "4806" should be -- 48% --

Signed and Sealed this

Twenty-third Day of April, 2002

Attest:

JAMES E. ROGAN
Attesting Officer *Director of the United States Patent and Trademark Office*